(12) United States Patent
Walen et al.

(10) Patent No.: US 11,660,101 B2
(45) Date of Patent: May 30, 2023

(54) SURGICAL INSTRUMENT WITH ARTICULATING REGION

(71) Applicant: Stryker Corporation, Kalamazoo, MI (US)

(72) Inventors: James G. Walen, Portage, MI (US); Bryan G. Deeny, Belleek (IE); Gerard Nunan, Ballincolig (IE)

(73) Assignee: Stryker Corporation, Kalamazoo, MI (US)

( * ) Notice: Subject to any disclaimer, the term of this patent is extended or adjusted under 35 U.S.C. 154(b) by 183 days.

(21) Appl. No.: 17/101,402

(22) Filed: Nov. 23, 2020

(65) Prior Publication Data

US 2021/0068620 A1 Mar. 11, 2021

Related U.S. Application Data

(63) Continuation of application No. 15/553,825, filed as application No. PCT/US2016/019880 on Feb. 26, 2016, now Pat. No. 10,874,290.

(Continued)

(51) Int. Cl.
*A61B 17/32* (2006.01)
*A61B 17/3207* (2006.01)
(Continued)

(52) U.S. Cl.
CPC ............ *A61B 1/0056* (2013.01); *A61B 1/005* (2013.01); *A61B 1/0051* (2013.01);
(Continued)

(58) Field of Classification Search
CPC combination set(s) only.
See application file for complete search history.

(56) References Cited

U.S. PATENT DOCUMENTS

| 4,811,736 A | 3/1989 | Griggs et al. |
| 5,454,787 A | 10/1995 | Lundquist |

(Continued)

FOREIGN PATENT DOCUMENTS

| DE | 102006000399 A1 | 2/2008 |
| EP | 0987988 A1 | 3/2000 |

(Continued)

OTHER PUBLICATIONS

English language abstract for EP 1 834 595 extracted from espacenet.com database on Nov. 16, 2017, 1 page.

(Continued)

*Primary Examiner* — Scott Luan
(74) *Attorney, Agent, or Firm* — Howard & Howard Attorneys PLLC

(57) ABSTRACT

A surgical instrument including an articulating region. An outer tube and an inner tube are axially fixed to one another distal to the articulating region and axially movable relative to one another proximal to the articulating region. Relative movement of the inner and outer tubes provides for articulation of the articulating tube assembly to a curved configuration. A working tool may be removably directed through a central cannula defined by the inner tube. The working tool may include a shaft having a flexible region configured to be arranged within the articulating region. The shaft may rotate within the inner tube with the articulating tube assembly in the curved configuration. The working tool may include a housing hub configured to be coupled with a handle to removably position the flexible region within the articulating region. Multiple working tools may be interchangeably directed through the central cannula.

20 Claims, 26 Drawing Sheets

Related U.S. Application Data

(60) Provisional application No. 62/121,080, filed on Feb. 26, 2015, provisional application No. 62/121,265, filed on Feb. 26, 2015.

(51) Int. Cl.
| | |
|---|---|
| *A61B 1/005* | (2006.01) |
| *A61B 17/16* | (2006.01) |
| *A61B 17/34* | (2006.01) |
| *A61B 17/00* | (2006.01) |
| *A61B 17/29* | (2006.01) |
| *A61M 25/01* | (2006.01) |
| *A61B 1/317* | (2006.01) |
| *A61B 18/00* | (2006.01) |

(52) U.S. Cl.
CPC ........ *A61B 1/0055* (2013.01); *A61B 17/1622* (2013.01); *A61B 17/1631* (2013.01); *A61B 17/1659* (2013.01); *A61B 17/32002* (2013.01); *A61B 17/320758* (2013.01); *A61B 1/317* (2013.01); *A61B 17/3421* (2013.01); *A61B 2017/00309* (2013.01); *A61B 2017/00314* (2013.01); *A61B 2017/00367* (2013.01); *A61B 2017/00477* (2013.01); *A61B 2017/2905* (2013.01); *A61B 2017/2908* (2013.01); *A61B 2017/2927* (2013.01); *A61B 2017/320032* (2013.01); *A61B 2018/00982* (2013.01); *A61B 2217/005* (2013.01); *A61M 25/0138* (2013.01); *A61M 25/0147* (2013.01)

(56) References Cited

U.S. PATENT DOCUMENTS

| | | | |
|---|---|---|---|
| 5,685,868 | A | 11/1997 | Lundquist |
| 5,851,212 | A | 12/1998 | Zirps et al. |
| 6,048,339 | A | 4/2000 | Zirps et al. |
| 6,423,059 | B1 | 7/2002 | Hanson et al. |
| 6,428,539 | B1 | 8/2002 | Baxter et al. |
| 6,503,263 | B2 | 1/2003 | Adams |
| 6,837,887 | B2 | 1/2005 | Woloszko et al. |
| 7,033,357 | B2 | 4/2006 | Baxter et al. |
| 8,088,081 | B2 | 1/2012 | Field et al. |
| 8,105,346 | B2 | 1/2012 | Nakanishi |
| 8,221,424 | B2 | 7/2012 | Cha |
| 8,251,977 | B2 | 8/2012 | Partlett |
| 8,323,241 | B2 | 12/2012 | Salahieh et al. |
| 8,672,921 | B2 | 3/2014 | Efinger et al. |
| 8,708,953 | B2 | 4/2014 | Salahieh et al. |
| RE44,883 | E | 5/2014 | Cha |
| RE44,896 | E | 5/2014 | Cha |
| 8,920,369 | B2 | 12/2014 | Salahieh et al. |
| 8,939,899 | B2 | 1/2015 | Kitagawa et al. |
| 2002/0082585 | A1 | 6/2002 | Carroll et al. |
| 2008/0051802 | A1 | 2/2008 | Schostek et al. |
| 2008/0140053 | A1 | 6/2008 | Partlett |
| 2008/0172037 | A1 | 7/2008 | Huang et al. |
| 2008/0249364 | A1 | 10/2008 | Korner |
| 2009/0023988 | A1 | 1/2009 | Korner et al. |
| 2010/0318067 | A1 | 12/2010 | Klima |
| 2011/0313251 | A1 | 12/2011 | Kitagawa et al. |
| 2012/0078377 | A1 | 3/2012 | Gonzales et al. |
| 2012/0130381 | A1 | 5/2012 | Germain |
| 2012/0221034 | A1 | 8/2012 | Dinger, III et al. |
| 2014/0135736 | A1 | 5/2014 | Hebert |
| 2014/0276966 | A1 | 9/2014 | Ranucci et al. |
| 2015/0073341 | A1 | 3/2015 | Salahieh et al. |
| 2015/0151080 | A1 | 6/2015 | Verbeek |
| 2018/0242962 | A1 | 8/2018 | Walen et al. |

FOREIGN PATENT DOCUMENTS

| | | |
|---|---|---|
| EP | 1834595 A2 | 9/2007 |
| EP | 1854417 A1 | 11/2007 |
| EP | 1886620 A2 | 2/2008 |
| EP | 1927375 A2 | 6/2008 |
| EP | 1977677 A1 | 10/2008 |
| EP | 2437845 A1 | 4/2012 |
| JP | 2002503132 A | 1/2002 |
| JP | 2008068070 A | 3/2008 |
| JP | 2008132332 A | 6/2008 |
| JP | 5404154 B2 | 1/2014 |
| WO | 9300119 A1 | 1/1993 |
| WO | 9856299 A1 | 12/1998 |
| WO | 2007142873 A2 | 12/2007 |
| WO | 2009114908 A1 | 9/2009 |
| WO | 2010141850 A1 | 12/2010 |
| WO | 2012151396 A2 | 11/2012 |
| WO | 2013056262 A1 | 4/2013 |

OTHER PUBLICATIONS

English language abstract for EP 1 886 620 extracted from espacenet.com database on Nov. 9, 2017, 1 page.
English language abstract for EP 1 977 677 extracted from espacenet.com database on Nov. 9, 2017, 1 page.
English language abstract for JP 2002-503132 extracted from espacenet.com database on Nov. 9, 2017, 1 page.
English language abstract for JP 2008-068070 extracted from espacenet.com database on Nov. 9, 2017, 1 page.
English language abstract for JP 2008-132332 extracted from espacenet.com database on Nov. 9, 2017, 1 page.
English language abstract for JP 5404154 extracted from espacenet.com database on Nov. 9, 2017, 1 page.
English language abstract not found for DE 10 2006 000 399; however, see English language equivalent U.S. 2008/0051802. Original document extracted from espacenet.com database on Nov. 9, 2017, 83 pages.
International Search Report for Application No. PCT/US2016/019880 dated Oct. 18, 2016, 7 pages.
York, Peter A. et al., "A Wrist for Needle-Sized Surgical Robots", IEEE Int Conf Robot Autom., May 2015, pp. 1776-1781.

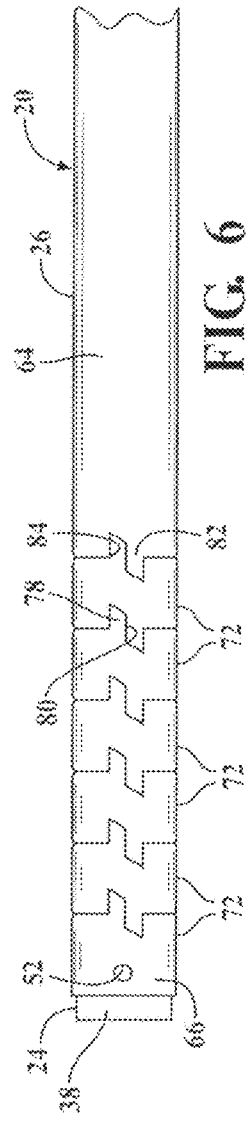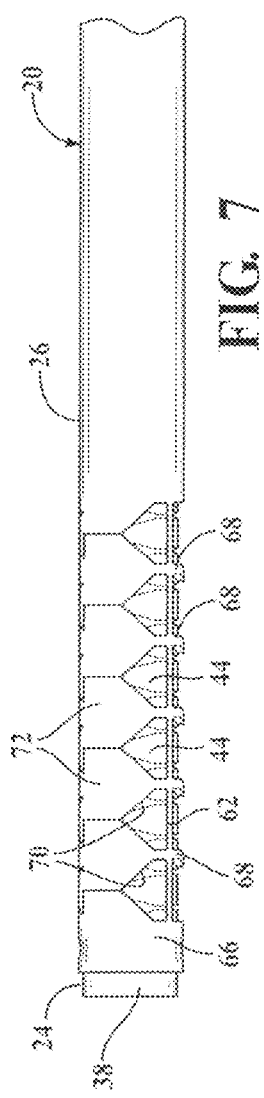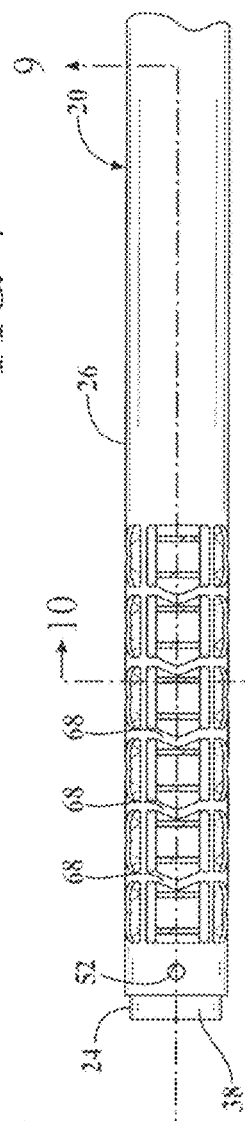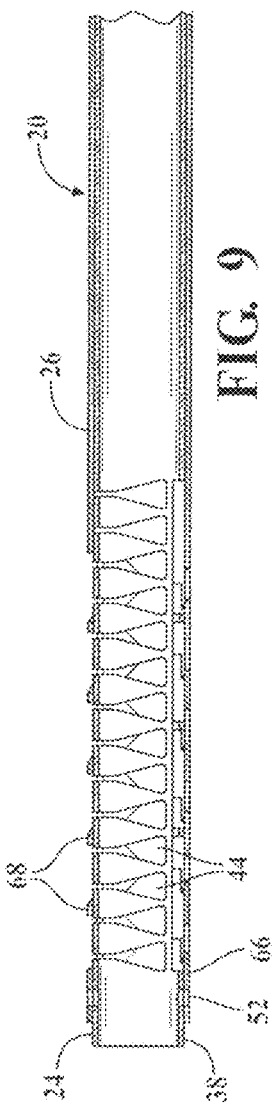

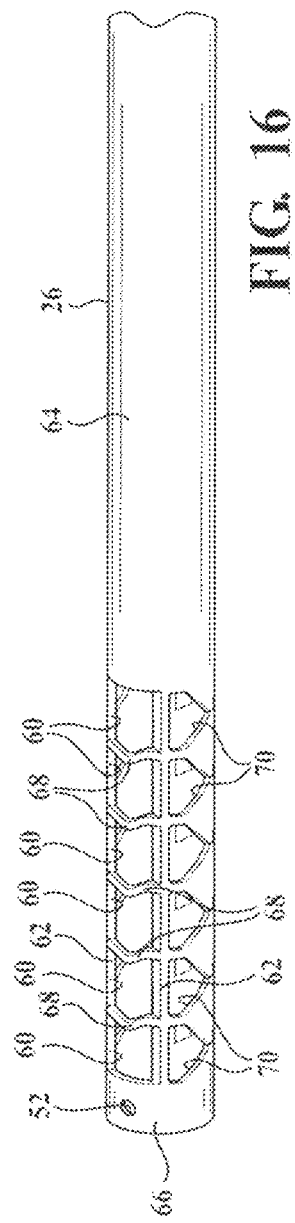

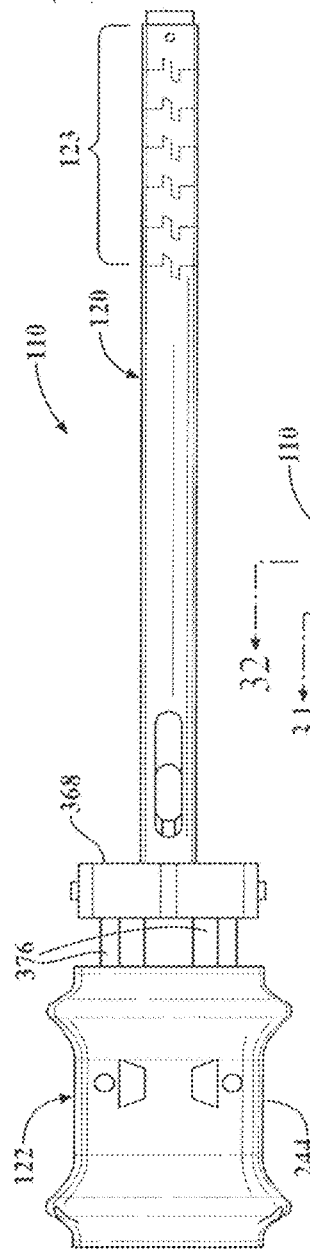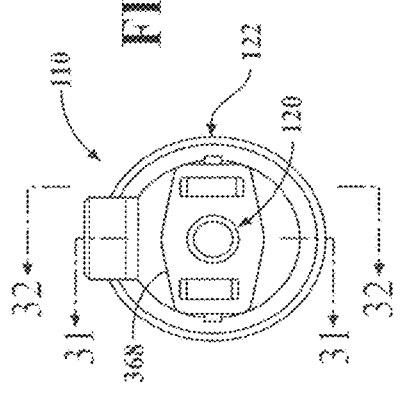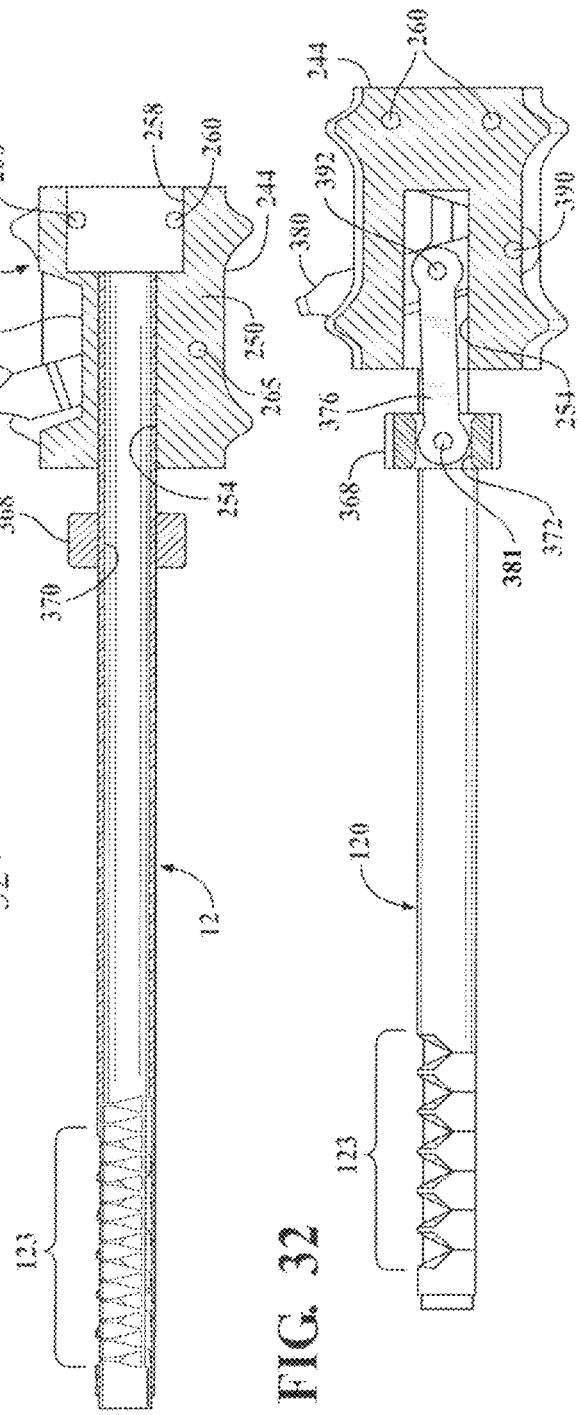

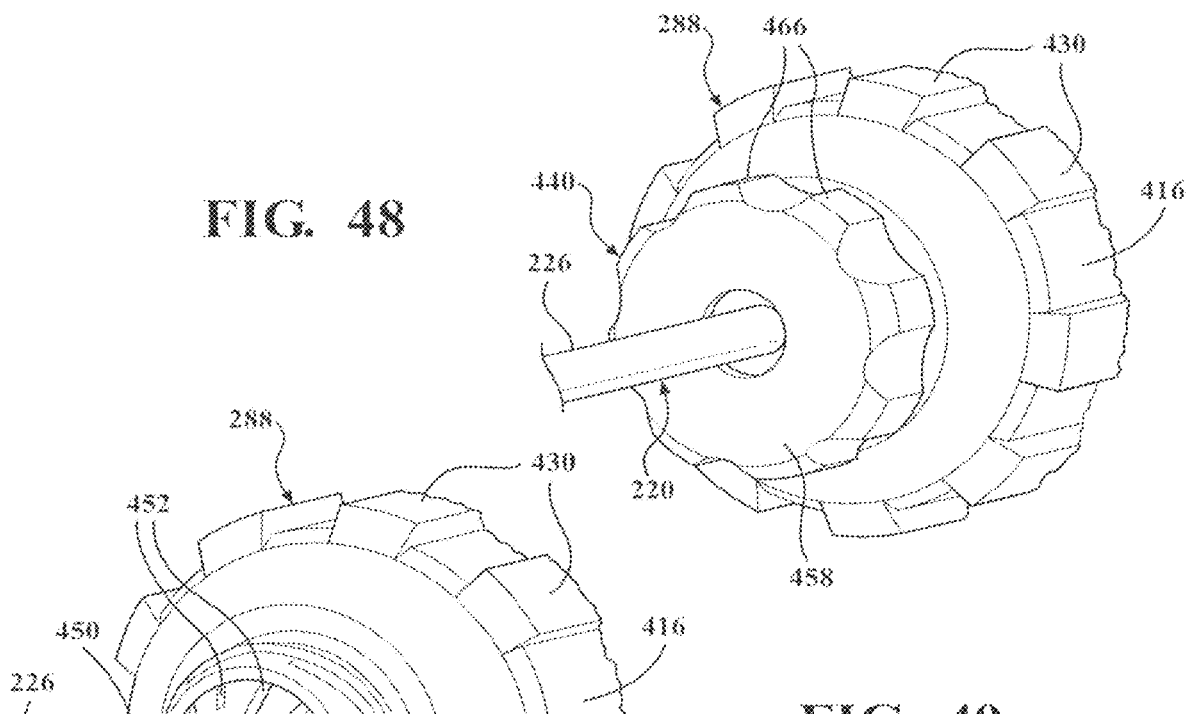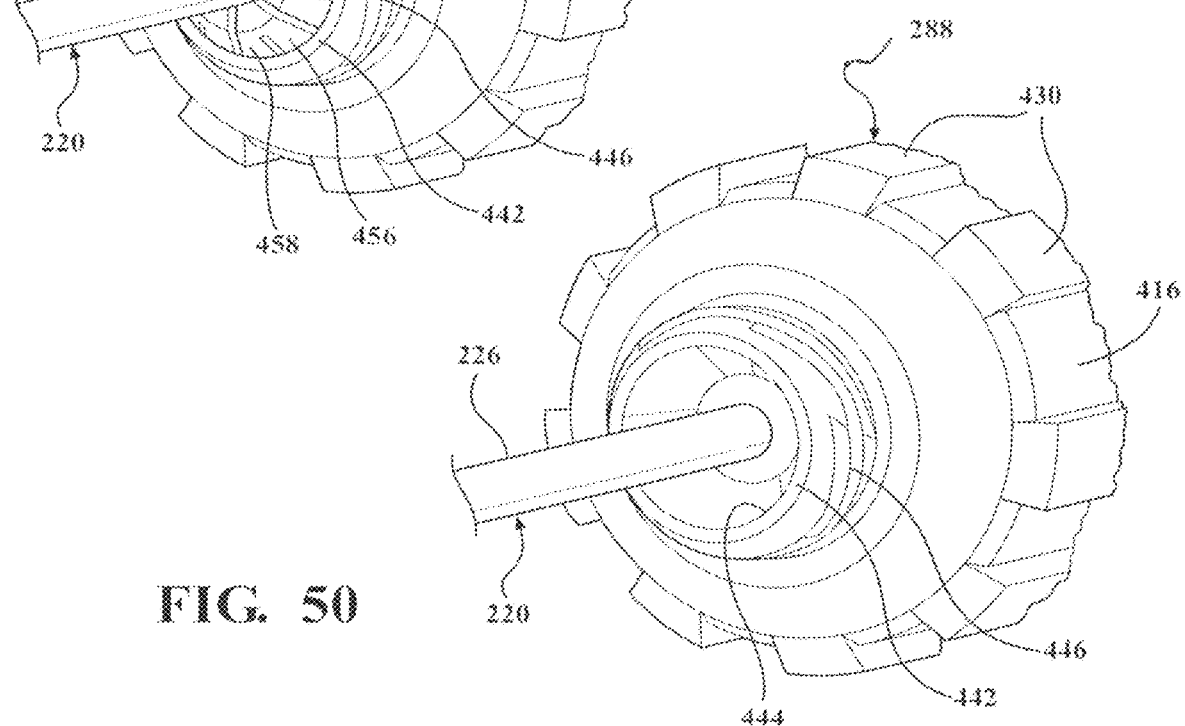

SURGICAL INSTRUMENT WITH ARTICULATING REGION

PRIORITY CLAIM

This a continuation of co-pending U.S. application Ser. No. 15/553,825, filed Feb. 26, 2016, which is a national stage entry of International Patent Application No. PCT/US2016/019880, filed Feb. 26, 2016, which claims priority to and all the benefits of U.S. Provisional Patent Application No. 62/121,265, filed Feb. 26, 2015, and U.S. Provisional Patent Application No. 62/121,080, filed Feb. 26, 2015, the entire contents of each are hereby incorporated by reference.

TECHNICAL FIELD

The present invention relates generally to surgical instruments and, more particularly to, a surgical instrument with tube articulation and illumination for use on patients.

BACKGROUND

It is known that medical practitioners have found it useful to use surgical instruments to assist in the performance of surgical procedures. A surgical instrument is designed to be applied to a surgical site on the patient. The practitioner is able to position the surgical instrument at the site on the patient at which the instrument is to perform a medical or surgical procedure. Today many procedures such a lateral and central foramenal decompression must be performed by removing considerable healthy tissue, specifically the lamina and the facet joints, just to access the portion of the foramen that is impinging the neural elements. This added morbidity is because the surgeons do not have tools that enable them to visualize or remove the impingement any other way.

Many articulating devices have been developed for use in surgical procedures. They are valuable because they facilitate reduced incision size, improved access and visibility, while enhancing surgical outcome and quicker recovery. Some articulate at a single hinge joint creating an abrupt angle at that location. While suitable for some applications, a hinge joint is not suitable for many applications such as those which require tissue extraction or rotary or reciprocating power transmission through a region of articulation. These and other applications require a more gradual curve to their articulation. Devices with such a gradual curve are generally constructed of multiple segments which shift or flex with respect to each other to accomplish the gradual curve. Many of these devices available today are extremely complicated assemblies with dozens of tiny moving parts, requiring painstaking assembly and considerable expense to maintain. One limitation to such multi-segment articulation devices is their lack of stiffness. A force applied off axes from the device can cause the device to shift slightly as the segments shift with respect to one another. This type of "snaking" movement is acceptable in certain application such as steerable endoscopes or steering catheters, but in others such as power-tool applications such as shavers or burs, such movement would result in highly undesirable poor control and stability.

Further, during arthroscopic surgery, there are occasions where bone needs to be removed from an area of anatomy of the patient that is difficult to access using a straight tool. For example, during an Anterior Interior Illicac Spine (AIIS) pincer removal in the hip, it can be difficult to access the AIIS region using traditional hip arthroscopy portal placements and straight tools. Additionally, the Psoas canal region of the hip is difficult to access using a straight tool.

For both of the above cases, an angled bur is potentially more useful than a straight bur. However, angled burs are difficult to almost impossible to insert down a standard hip arthroscopy cannula depending on the degree of angle of the tool. In this case, it would be desirable to have an articulating bur which can be toggled from straight to angled by the surgeon. However, this would require the bur to be rigid enough to allow the bur head to be pressed against the bone to enable fast debridement.

In addition, line of sight is a common limitation in the surgical field. The surgical site is often enlarged in order to improve the surgeon's line of sight. This enlarging of the surgical site results in significant collateral damage, pain, and longer recovery times for the patient. An endoscope goes a long way to address these issues and has moved the surgeon's point of view from outside the surgical site to inside the patient. Angled tipped endoscopes and articulating endoscopes have further changed the surgeon's point of view by enabling off axis viewing, or a view that is no longer along a central axis of a rigid scope shaft.

In many situations, as a surgical instrument is introduced to the surgical site, the distal end of the instrument, and the tissue it contacts, is not visible to the surgeon because the instrument itself obstructs the surgeon's view. Curved instruments and articulating instruments are capable of reaching and working around corners, but because the surgeon's line of sight is limited to a straight line, the safety and effectiveness of these tools is limited.

While the traditional or open endoscopic techniques used today by surgeons provide a "global view" of the surgical site, there is a need to provide a secondary "local view" that is otherwise not available to the surgeon. Further, in some cases, the surgical site can be difficult to illuminate sufficiently. Therefore, there is a need in the art to provide a surgical instrument having tube articulation and illumination for use on a patient.

SUMMARY

Accordingly, the present invention provides a surgical instrument including an articulating tube assembly having a proximal end and a distal end, an articulating region disposed between the proximal end and the distal end, and a proximal axis axially extending from the proximal end to the articulating region. The articulating tube assembly includes an inner tube and an outer tube each having the articulating region. The inner tube and the outer tube are movable relative to each other proximal to the articulating region and fixed axially relative one another distal to the articulating region. The surgical instrument also includes an actuation assembly coupled to the articulating tube assembly for moving the inner tube and the outer tube axially relative to each other for articulating the articulating region of the articulating tube assembly between a first configuration and a second configuration. The articulating region is rigid in the first configuration and the second configuration.

The present invention also provides a surgical instrument including an articulating tube assembly having a proximal end and a distal end, an articulating region disposed between the proximal end and the distal end, and a proximal axis axially extending from the proximal end to the articulating region. The articulating tube assembly includes an inner tube and an outer tube each having the articulating region. The inner tube and the outer tube are movable relative to each other proximal to the articulating region and fixed axially relative one another distal to the articulating region. The surgical instrument also includes an actuation assembly coupled to the articulating tube assembly for moving the inner tube and the outer tube axially relative to each other for articulating the articulating region of the articulating tube assembly between a first configuration and a second configuration in only a single plane. The surgical instrument further includes a viewing assembly coupled to the articulating tube assembly for allowing an operator to view the distal end of the articulating tube assembly and an illumination assembly coupled to the articulating tube assembly for providing illumination to the distal end of the articulating tube assembly.

The present invention further provides a surgical instrument including an articulating tube assembly having a proximal end and a distal end, an articulating region disposed between the proximal end and the distal end, and a proximal axis axially extending from the proximal end to the articulating region. The articulating tube assembly includes an inner tube and an outer tube each having the articulating region. The inner tube and the outer tube are movable relative to each other proximal to the articulating region and fixed axially relative one another distal to the articulating region. The surgical instrument also includes an actuation assembly coupled to the articulating tube assembly for moving the inner tube and the outer tube axially relative to each other for articulating the articulating region of the articulating tube assembly between a first configuration and a second configuration in only a single plane. The surgical instrument further includes a torque member disposed within the inner tube, a rotatable end effector disposed distal of the articulating region and coupled to the torque member, and a driveshaft coupled to the torque member and adapted to be coupled to a drive assembly to drive the torque member and the rotatable end effector.

In addition, the present invention provides a method of operating a surgical instrument including the steps of providing an articulating tube assembly having a proximal end and a distal end, an articulating region disposed between the proximal end and the distal end, and a proximal axis axially extending from the proximal end to the articulating region. The articulating tube assembly includes an inner tube and an outer tube each having the articulating region. The inner tube and the outer tube are movable relative to each other proximal to the articulating region and fixed axially relative one another distal to the articulating region. The method also includes the steps of providing an actuation assembly coupled to the articulating tube assembly, rotating a rotation assembly of the actuation assembly with one hand of a user and, moving with one hand of the user the inner tube and the outer tube axially relative to each other for articulating the articulating region of the articulating tube assembly between a first configuration and a second configuration in only a single plane.

Other features and advantages of the present invention will be readily appreciated, as the same becomes better understood, after reading the subsequent description

BRIEF DESCRIPTION OF THE DRAWINGS

FIG. 6 is a top view of an articulating region of a tube assembly of the surgical instrument of FIG. 1.

FIG. 7 is a side view of an articulating region of the tube assembly of the surgical instrument of FIG. 1.

FIG. 8 is a bottom view of an articulating region of the tube assembly of the surgical instrument of FIG. 1.

FIG. 9 is a sectional view taken along line 9-9 of FIG. 8.

FIG. 16 is a perspective view of an articulating region of an outer tube of the tube assembly of FIG. 11.

FIG. 17 is a top view of an articulating region of an outer tube of the tube assembly of FIG. 11.

FIG. 18 is a side view of an articulating region of an outer tube of the tube assembly of FIG. 11.

FIG. 19 is a bottom view of an articulating region of an outer tube of the tube assembly of FIG. 11.

FIG. 29 is a top view of another embodiment, according to the present invention, of the surgical instrument of FIGS. 1 and 2.

FIG. 30 is an end view of the surgical instrument of FIG. 29.

FIG. 31 is a sectional view taken along line 31-31 of FIG. 30.

FIG. 32 is a sectional view taken along line 32-32 of FIG. 30.

FIG. 48 is a perspective view of the surgical instrument of FIG. 46 with the locking assembly assembled.

FIG. 49 is a perspective view of the surgical instrument of FIG. 46 with a locking wheel of the locking assembly removed.

FIG. 50 is a perspective view of the surgical instrument of FIG. 46 with the floating collet and the locking wheel of the locking assembly removed.

DETAILED DESCRIPTION

Figure 1:
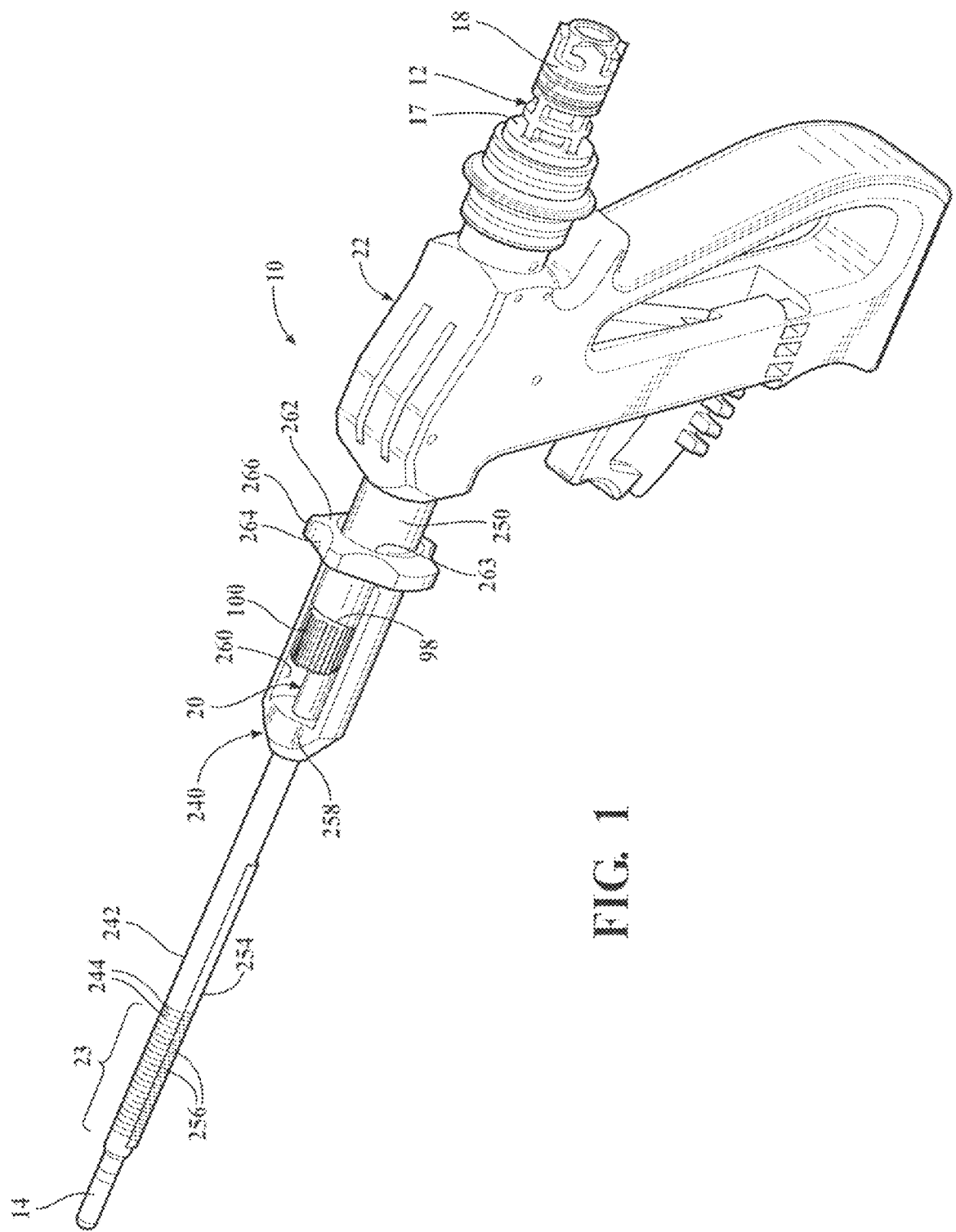
FIG. 1 is a perspective view of one embodiment of a surgical instrument, according to the present invention, illustrated in operational relationship with a surgical tool.
Figure 2:
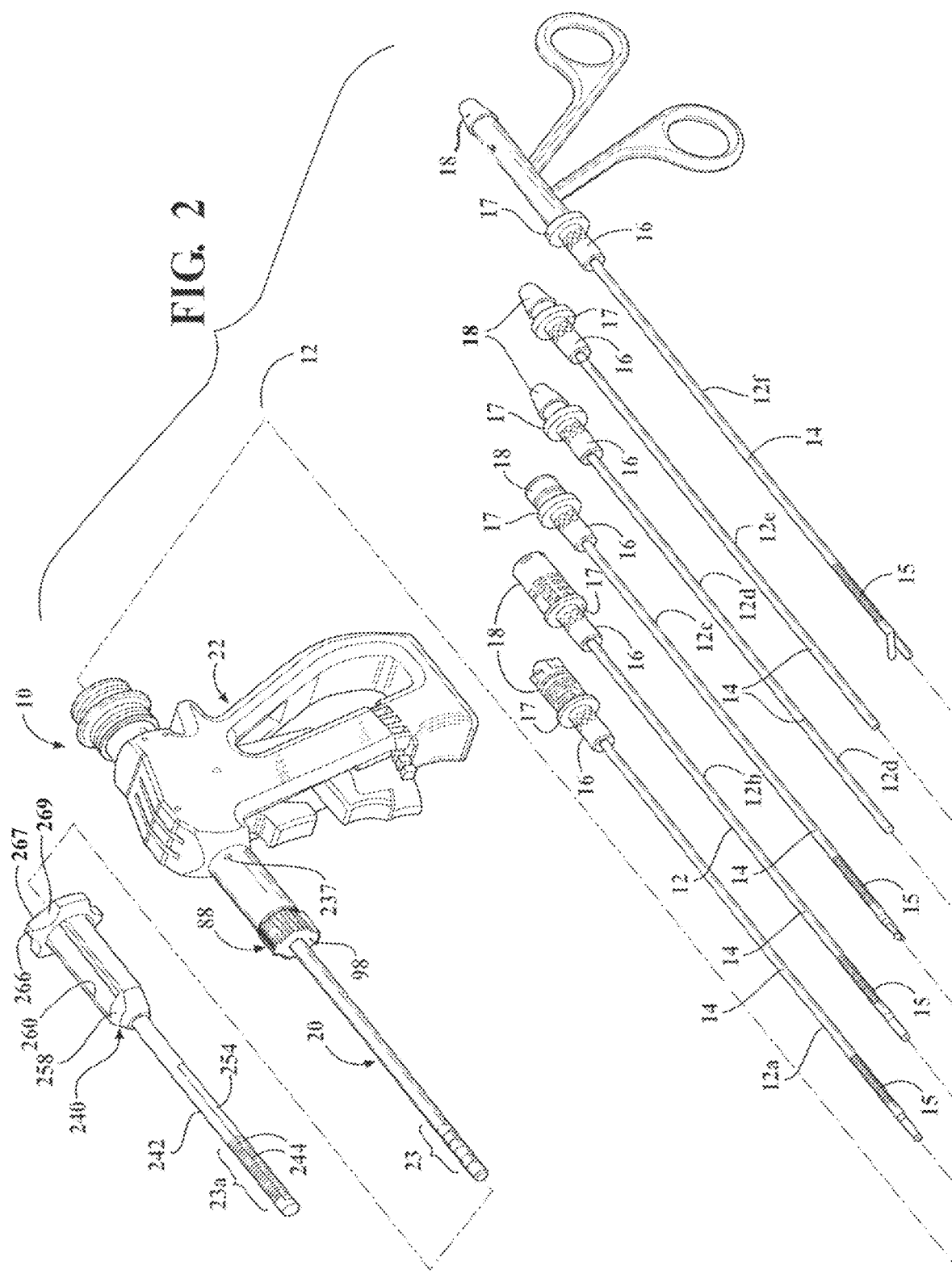
FIG. 2 is an exploded view of the surgical instrument, a tool view assembly, and one or more surgical tools for the surgical instrument of FIG. 1.

Referring to FIGS. 1 and 2, a surgical instrument 10, according to the present invention, is shown for use in a medical procedure for a patient (not shown). As illustrated in FIG. 2, the surgical instrument 10 is used with one or more working tools 12. The surgical instrument 10 is capable of receiving and releaseably securing one of the working tools 12.

Exemplary working tools 12 may be a flexible bur 12a, a flexible bur 12b, a flexible high speed bur 12c, a flexible suction device 12d, a flexible internal imaging and suction device 12e, and/or a flexible manual instrument 12f such as graspers, bipolar forceps, etc. Powered tissue devices 12a, 12b, and 12c and manual instrument 12f comprise a shaft portion 14 and a flexible region 15 along the shaft portion 14 near a distal end. The flexible suction device 12d and flexible internal imaging and section device 12e of the working tools 12 are devices that are configured to flex along at least a portion, of the entire length of the shaft portion 14.

In the illustrated embodiment, each of these working tools 12 also have a generally cylindrical enlarged insertion portion 16 along the shaft portion 14 near a proximal end and a flange portion 17 extending radially outwardly at the end of the insertion portion 16. Each of these working tools 12a, 12b, 12c further comprise a connecting portion 18 extending axially away from the flange portion 17. The connecting portion 18 is configured to couple the working tool 12 to a power source, a suction source, and/or irrigation source (not shown). Alternatively, it is further contemplated that each of these working tools 12d, 12e, 12f have a connecting portion 18 for connection to a suction source only. It should be appreciated that the working tools 12 illustrated herein are mere examples of the various working tools 12 that are configured to be inserted into the surgical instrument 10. Thus, it should also be appreciated that other working tools 12 may be introduced through and controlled by the surgical instrument 10 such as reciprocating devices like rasps, rotating devices, electrosurgical devices, laser devices, screwdriver devices, obturators, and trocars are further contemplated for use with the surgical instrument 10. It should further be appreciated that the working tool 12 is configured to be inserted into the surgical instrument 10 and extend outwardly from the surgical instrument 10. It should still be further appreciated that the surgical instrument 10 may be operated by a user (not shown) such as a surgeon.

Figure 3:
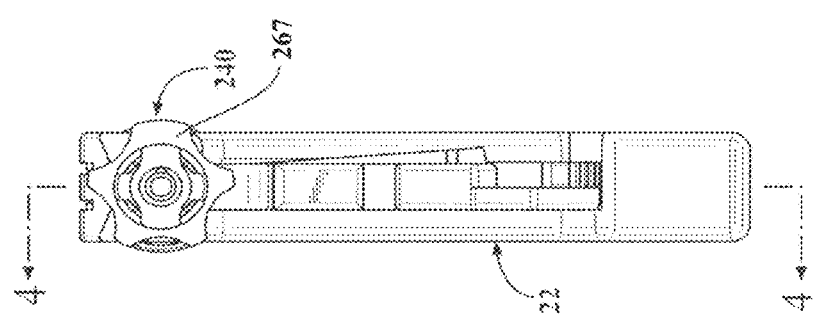
FIG. 3 is an end view of the surgical instrument of FIG. 1.
Figure 5:
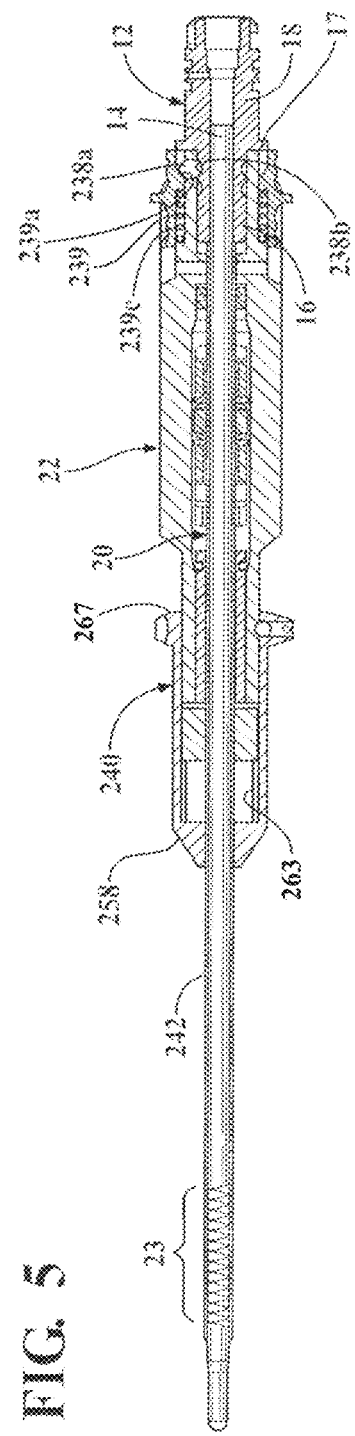
FIG. 5 is a sectional view taken along line 5-5 of FIG. 4.
Figure 4:
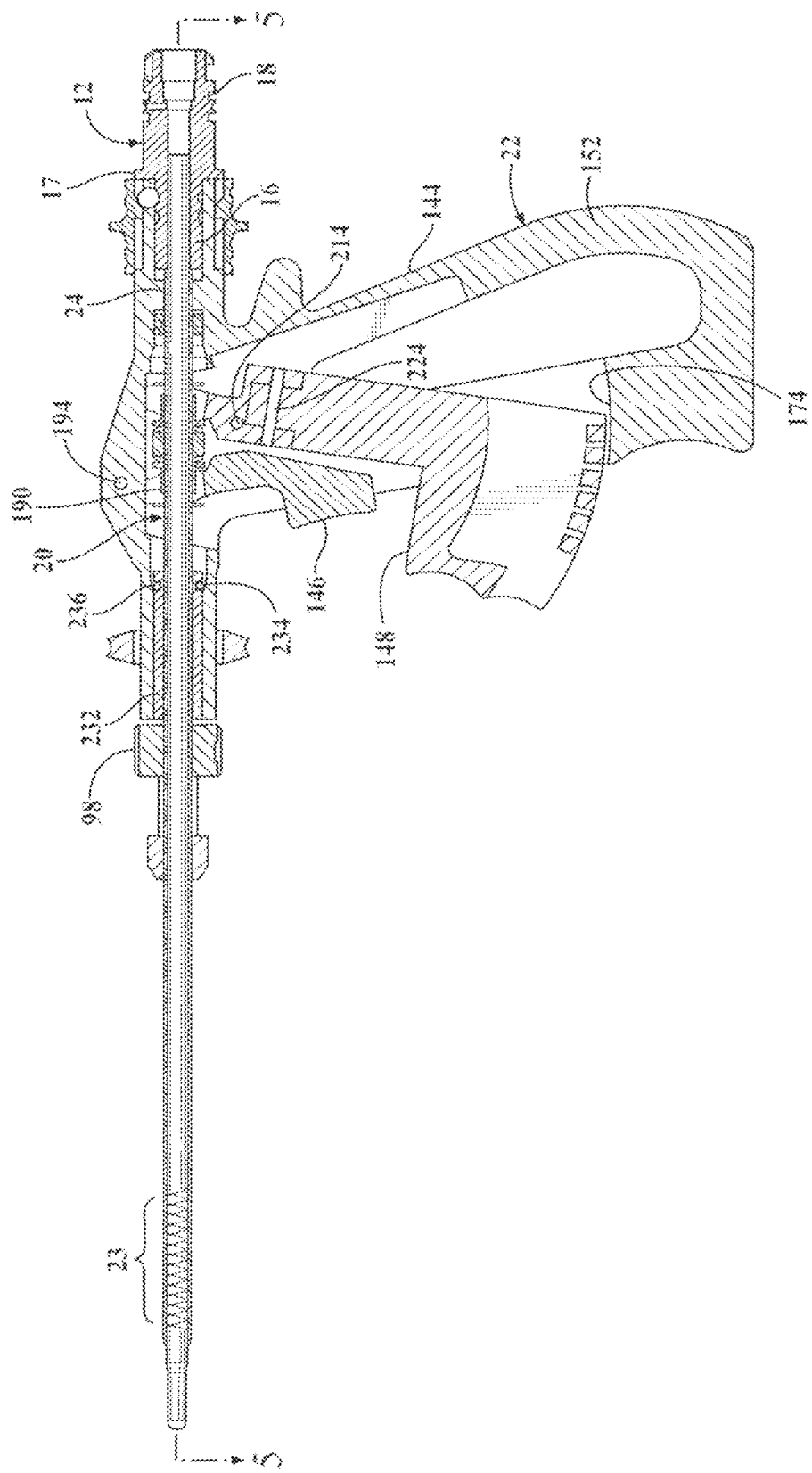
FIG. 4 is a sectional view taken along line 4-4 of FIG. 3.

Referring to FIGS. 3 through 5, the surgical instrument 10 includes an articulating tube assembly, generally indicated at 20, and an actuation assembly, generally indicated at 22, coupled to the articulating tube assembly 20 and which controls the articulating tube assembly 20. The articulating tube assembly 20 includes an articulating region 23 along a length of the articulating tube assembly 20. The articulating region 23 is disposed proximal the distal end and may be axially spaced from the distal end of the articulating tube assembly 20 or may be axially abutting the distal end of the articulating tube assembly 20.

It should be appreciated that one or more of the working tools 12 have a shaft portion 14 capable of fitting within the articulating tube assembly 20 such that the flexible region 15 of the working tool 12 tends to align or at least partially align with the articulating region 23 when the working tool 12 is disposed in the surgical instrument 10. The flexible region 15 of the working tool 12, when aligned with the articulating region 23 of the articulating tube assembly 20, allows these regions to bend or curve together.

It should also be appreciated that the distal end of many of these working tools 12 might protrude slightly beyond the distal end of the articulating tube assembly 20 in order to perform their function, while other working tools may be operable without their distal ends extending through the distal end of the surgical instrument 10. Furthermore, some working tools 12 may be operable even if their distal ends are proximal to the distal end of the surgical instrument 10. It should further be appreciated that other working tools 12 have the ability to be extended beyond to varying degrees, brought even with, or withdrawn into the distal end of the articulating tube assembly 20.

Referring to FIGS. 4 through 19, in the illustrated embodiment, the articulating tube assembly 20 includes a first or inner tube 24 and a second or outer tube 26. Each of the inner tube 24 and outer tube 26 are generally hollow cylinders and has a generally circular cross-sectional shape. The outer tube 26 has a diameter greater than a diameter of the inner tube 24 such that the inner tube 24 is disposed within the outer tube 26. The inner tube 24 and outer tube 26 extend axially between a proximal end and a distal end. In this embodiment, the inner tube 24 has an axial length longer than an axial length of the outer tube 26 such that the inner tube 24 extends past a distal end of the outer tube 26 when the inner tube 24 is disposed within the outer tube 26 and the proximal end of the inner tube 24 extends axially past a proximal end of the outer tube 26 when the inner tube 24 is disposed within the outer tube 26.

The inner tube 24 and outer tube 26 each independently comprise a metal material such as stainless steel or a non-metallic material such as a plastic composite depending on the application of the surgical instrument 10. It should be appreciated that the wall thickness of the inner tube 24 and outer tube 26 may be relatively thin such as approximately 0.1 to approximately 0.5 millimeters (mm) to allow the articulating tube assembly 20 to have a relatively small diameter and also to be light-weight. It should also be appreciated that, in certain embodiments, the diameters of the inner tube 24 and outer tube 26 have a diameter of from approximately 1.0 mm to approximately 3.0 mm so as to work in a small opening of the patient and to prevent the user's view from being obstructed. It should further be appreciated that, in some applications, the inner tube 24 and outer tube 26 may have larger diameters such as approximately 10 mm or larger sufficient to accommodate the working tools 12 such as a screwdriver. It should still further be appreciated that, in certain embodiments, the diameter of the inner tube 24 and outer tube 26 may be scaled larger or smaller depending on the application and the size of the working tool 12.

Referring to FIGS. 12 through 15, the inner tube 24 and outer tube 26 each include the articulating region 23 are fixed together distal of the articulating regions 23 to allow the inner tube 24 and outer tube 26 to be pushed and pulled relative to each other. The inner tube 24 includes apertures 32, beams 34, tie straps 40, apertures 42, and bottom segments 44 to form the articulating region 23 in the inner tube 24. The outer tube 26 includes apertures 60, beams 62, tie straps 68, apertures 70, and bottom segments 72 to form the articulating region 23 in the outer tube 26.

The inner tube 24 includes an aperture 28 extending diametrically therethrough near the distal end thereof to allow the inner tube 24 to be fixed to the outer tube 26. The aperture 28 is generally circular in shape, but may be any suitable shape. The inner tube 24 includes an aperture 30 extending through a wall thereof and disposed between the articulating region 23 and the proximal end for a connection to be described. In one embodiment, the aperture 30 is generally elongated, but may be any suitable shape.

Figure 10:
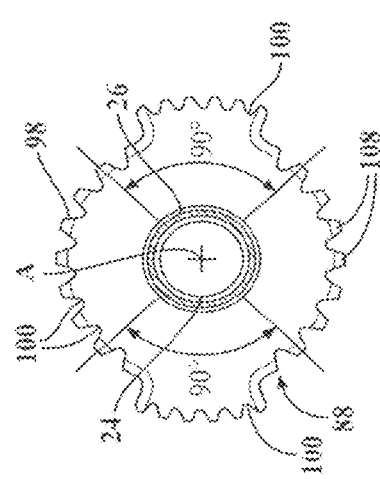
FIG. 10 is a sectional view taken along line 10-10 of FIG. 8.

The articulating region 23 of the inner tube 24 includes one or more apertures 32 extending through a wall thereof. In the illustrated embodiment, the apertures 32 are generally rectangular in shape. However, other shapes of the apertures 32 are contemplated. As illustrated, the apertures 32 have an axial length greater than a circumferential width, but need not be so. The inner tube 24 includes a plurality of beams 34 formed by cutting the apertures 32 and 42. The beams 34 extend axially to form generally linear beams 34. These beams 34 are parallel and extend from a long proximal portion 36 of the inner tube 24 to a shorter distal portion 38 of the inner tube 24. The beams 34 are located approximately ninety degrees (90°) from each other as illustrated in FIG. 10.

The inner tube 24 also includes one or more of tie straps 40 formed by cutting the apertures 32. The tie straps 40 extend circumferentially between and spaced axially along the beams 34. It should be appreciated that each of the beams 34 may be instead one continuous axially extending beam or a plurality or series of axially extending beams 34. It should also be appreciated that the tie straps 40 collectively maintain a cylindrical profile of the articulating region 23 of the inner tube 24 and prevent the beams 34 from buckling during compression of the inner tube 24. It should further be appreciated that the beams 34 are the main tension or compression members, deliver loads, and have to bend. It should also be appreciated that the apertures 32 are formed by cutting the inner tube 24.

The inner tube 24 includes one or more apertures 42 extending radially therethrough below the beams 34. The apertures 42 have an inverted generally pentagonal shape. The apertures 42 are formed by cutting the inner tube 24. The inner tube 24 also includes one or more bottoming segments 44 formed by cutting the apertures 42 disposed below and extending from the beams 34. The bottoming segments 44 are generally triangular or pentagonal in shape, but may be any suitable shape. The bottoming segments 44 extend circumferentially between and spaced axially along the beams 34. Each of the bottoming segments 44 have a lower side 46 that is inclined by a predetermined angle, for example such as approximately two and one half degrees) (2.5°) in one embodiment. The bottoming segments 44 have a bottom 48 that extends axially a distance greater than a top 50 thereof. It should be appreciated that the bottoming segments 44 bottom out and provide surface to surface contact against each other in an articulated or curved configuration. It should also be appreciated that an axial gap or space is formed between the bottoming segments 44. It should further be appreciated that the apertures 42, beams 34, and bottoming segments 44 allow the articulating region 23 of the inner tube 24 to articulate. It should further be appreciated that each of the bottoming segments 44 has, when articulated, a small angular displacement such as approximately three and one-half degrees (3.5°) or approximately four degrees (4°).

Referring to FIGS. 11 and 16 through 19, the outer tube 26 also includes an aperture 52 extending diametrically therethrough near the distal end thereof for a function to be described. The outer tube 26 includes a slot aperture 54 extending through a wall thereof and disposed between the articulating region 23 and the proximal end for a function to be described. The slot aperture 54 extends axially and is elongated. The outer tube 26 includes a pad 56 disposed in the slot aperture 54 and a tab 58 extending axially between the outer tube 26 and the pad 56 to temporarily connect the pad 56 to the outer tube 26. The pad 56 is generally elongated axially.

The articulating region 23 of the outer tube 26 includes one or more apertures 60 extending through a wall thereof. In the illustrated embodiment, the apertures 60 are generally rectangular in shape. The apertures 60 are formed by cutting the outer tube 26. The outer tube 26 also includes a plurality of beams 62 formed by cutting the apertures 60. The beams 62 extend axially to form generally linear beams 62. These beams 62 are parallel to each other and extend from a long proximal portion 64 of the outer tube 26 to a shorter distal portion 66 of the outer tube 26 as illustrated in FIGS. 6 and 7. The beams 62 are located approximately ninety degrees (90°) circumferentially from each other. It should be appreciated that the beams 62 are the main tension or compression members, deliver loads, and have to bend.

The outer tube 26 includes a plurality of tie straps 68 formed by cutting the apertures 60 extending circumferentially between and axially spaced along the beams 62. The tie straps 68 prevent the beams 62 from buckling during axial compression of the outer tube 26. The tie straps 68 are generally "V" shaped axially toward the distal portion 66 to prevent snagging on the bottoming segments 44 of the inner tube 24 when the tube assembly 20 is articulated. It should be appreciated that each of the beams 62 may instead be one continuous axially extending beam or a plurality or series of axially extending beams 62. It should be appreciated that the tie straps 68 maintain a cylindrical profile of the articulating region 23 of the outer tube 26 and prevent the beams 62 from buckling during compression of the outer tube 26. It should also be appreciated that the tie straps 68 have a slight "V" form so to facilitate the passage of the segments 44 of the inner tube 24 past the tie straps 68 of the outer tube 26.

The outer tube 26 includes one or more apertures 70 extending radially therethrough below the beams 62. The apertures 70 have an inverted generally pentagonal shape. The apertures 70 are formed by cutting the outer tube 26. The outer tube 26 includes one or more bottoming segments 72 formed by cutting the apertures 70 disposed below and extending from the beams 62. The bottoming segments 72 are generally pentagonal in shape, but may be any suitable shape. The bottoming segments 72 extend circumferentially between and are spaced axially along the beams 62. The bottoming segments 72 have a bottom 74 that extends axially a distance greater than a top 76 thereof. It should be appreciated that the bottoming segments 72 provide rigidity in an axial extending or straight configuration. It should also be appreciated that a narrow axial gap or space is formed between the bottoming segments 72.

Each bottom 74 of the bottoming segments 72 has a first protrusion 78 extending axially from a proximal end toward the proximal end of the outer tube 26 and a first recess 80 extending axially from the proximal end toward the distal end of the outer tube 26. Each bottom 74 of the bottoming segments 72 has a second protrusion 82 extending axially from a distal end toward the distal end of the outer tube 26 and a second recess 84 extending axially from the distal end toward the proximal end of the outer tube 26 in one embodiment.

For the articulating region 23 in the inner tube 24, the inner tube 24 has a greater number of apertures 42 forming the bottoming segments 44. In one embodiment, the inner tube 24 has fourteen apertures 42 and thirteen bottoming segments 44. For the articulating region 23 in the outer tube 26, the outer tube 26 has a greater number of apertures 70 forming the bottoming segments 72. In one embodiment, the outer tube 26 has six apertures 70 and five bottoming segments 72. It should be appreciated that, in other embodiment, the number of apertures 42, 70 and segments 44, 72 may be greater or less.

Adjacent the articulating region 23, the distal portion 66 of the outer tube 26 has a first protrusion 78 extending axially from a proximal end toward the proximal end of the outer tube 26 and a first recess 80 extending axially from the proximal end toward the distal end of the outer tube 26. The proximal portion 64 of the outer tube 26 has a second protrusion 82 extending axially from a distal end toward the distal end of the outer tube 26 and a second recess 84 extending axially from a distal end toward the proximal end of the outer tube 26. The protrusions 78, 82 and recesses 80, 84 are generally rectangular in shape. The first protrusion 78 is disposed in the second recess 84 and the second protrusion 82 is disposed in the first recess 80 when the articulating region 23 is in an axially straight configuration. It should be appreciated that the protrusions 78, 82 and recesses 80, 84 are formed by cutting the outer tube 26 in a narrow cut to form a general "zig zag" or "Z" shape pattern such that each segment 72 has protrusions 78, 82 that extend into the neighboring segments 72. It should also be appreciated that the protrusions 78, 82 and recesses 80, 84 facilitate the smooth passage of the tie straps 40 of the inner tube 24 past the edges of the bottoming segments 72 on the outer tube 26 and increase torsional and rotational stiffness of the outer tube 26. It should further be appreciated that the apertures 70, beams 62, and segments 72 allow the articulating region 23 of the outer tube 26 to articulate.

In one example, when the inner tube 24 and outer tube 26 are fixed together axially distal of the articulating region 23, the outer tube 26 is pushed/pulled proximally with respect to the inner tube 24, causing the articulating tube assembly 20 to articulate until the bottoming segments 44 of the inner tube 24 bottom on each other and moves the outer tube 26 proximally with respect to the inner tube 24, causing the articulating tube assembly 20 to articulate until the bottoming segments 72 of the outer tube 26 bottom on each other. When the proximal end of the outer tube 26 is pulled distally relative to the inner tube 24, the beams 62 of the outer tube 26 are put in compression and the beams 34 of the inner tube 24 are put in tension. This loading causes a curve in the articulating region 23 of the articulating tube assembly 20 toward the beams 34 of the inner tube 24, which are in tension. The articulating region 23 of the articulating tube assembly 20 curves until the bottoming segments 72 of the outer tube 26 bottom on each other, closing the small gap between these bottoming segments 72. With a significant load applied in this bottomed condition, the articulating region 23 of the articulating tube assembly 20 is rigid as there is considerable loading about the circumference holding the bottoming segments 72 in place. Because there are relatively few and narrow gaps between bottoming segments 72 of the outer tube 26, it should be appreciated that relatively minimal tube curvature occurs. As this force is increased, the articulating tube assembly 20 becomes increasingly rigid in a nearly straight condition. It should be appreciated that the inner tube 24 and outer tube 26, when assembled, may lock in two directions such that the curves are in opposite directions or one curve in one direction is greater than the other curve in the other direction. It should also be appreciated that the outer tube 26 limits flexion for a straight configuration and the inner tube 24 limits flexion in a curved configuration.

Referring to FIGS. 5 through 10, the pair of beams 34 of the inner tube 24 and the pair of beams 62 of the outer tube 26 are oriented opposite at approximately one hundred eighty degrees (180°) from each other to provide lateral stiffness and rigidity of the articulating tube assembly 20. In other embodiments, the pair of beams 34 of the inner tube 24 and the pair of beams 62 of the outer tube 26 are oriented opposite at approximately one hundred seventy degrees (170°) to one hundred ninety degrees (190°) from each other. From these beams 34 and 62, the bottoming segments 44 and 72 and tie straps 40 and 68, respectively, are hung. The bottoming segments 44 and 72 project toward and around a central axis or centerline A extending axially along the articulating tube assembly 20 and connect the two beams 34 and 62 together. The tie straps 40 and 68 project away from, but around the centerline A and connect the two beams 34 and 62 together, respectively. The bottoming segments 44 and 72 have distal and proximal surfaces and a small gap separating the distal surface of one bottoming segment 72 from the proximal surface of the next or adjacent bottoming segment 72. In the embodiment illustrated, the bottoming segments 72 of the outer tube 26 are considerably axially wider than the bottoming segments 44 of the inner tube 24 and the gap between the bottoming segments 72 of the outer tube 26 is considerably smaller than the gap between the bottoming segments 44 of the inner tube 24. It should be appreciated that while in the embodiment illustrated, each tube 24 and 26 has two beams 34 and 62, respectively, at 90 degrees and each pair diametrically opposed from each other, other embodiments might have only one beam per tube. It should further be appreciated that, in still other embodiments, there may be more than two beams per tube.

It should still further be appreciated that, at the proximal end of the surgical instrument 10, there are components that enable the surgeon to control the articulation and allow the surgical instrument 10 to attach to and be driven by a drive assembly (not shown).

Referring to FIGS. 1, 10, 11, and 20 through 22, the articulating tube assembly 20 includes a rotation assembly, generally indicated at 88, for angularly rotating a distal end of the articulating tube assembly 20. In the embodiment illustrated, the rotation assembly 88 includes an angular rotation tube 90 configured for rotating the inner tube 24 and outer tube 26. The angular rotation tube 90 is a generally hollow cylinder having a generally circular cross-sectional shape. The angular rotation tube 90 has a diameter greater than a diameter of the outer tube 26 such that the angular rotation tube 90 is disposed about the outer tube 26. The angular rotation tube 90 extends axially a predetermined distance and has an axial length substantially less than an axial length of the outer tube 26. The angular rotation tube 90 includes a slot aperture 92 extending through a wall thereof for a function to be described. The slot aperture 92 is elongated axially. The angular rotation tube 90 includes a pad 94 disposed in the slot aperture 92 and a tab 96 extending axially between the pad 94 and the angular rotation tube 90. The angular rotation tube 90 is made of a metal material or non-metallic material depending on the application. It should be appreciated that the angular rotation tube 90 is fixed to the outer tube 26 and the outer tube 26 is fixed to the inner tube 24 in a manner to be described.

The rotation assembly 88 also includes an angular rotation collar 98 to be rotated by the user of the surgical instrument 10. The angular rotation collar 98 may be generally circular in shape and include a pair of opposed protrusions 100 extending radially for a function to be described. The angular rotation collar 98 also includes an aperture 102 extending axially therethrough to allow the angular rotation collar 98 to be disposed over and about the angular rotation tube 90. The angular rotation collar 98 may include a knurled area 104 disposed in the aperture 102 for connection to the angular rotation tube 90. The angular rotation collar 98 has an outer surface with a plurality of grooves 106 and a plurality of gripping members 108 extending axially and spaced circumferentially. The grooves 106 and gripping members 108 are generally "V" shaped, but may be any suitable shape. One of the protrusions 100 may include a recess 111 extending radially therein and axially therealong to allow the user to feel which way the articulating tube assembly 20 will articulate. It should be appreciated that the grooves 106 and 108 are formed on the protrusions 100. It should also be appreciated that the angular rotation collar 98 is coupled to the angular rotation tube 90 through a suitable mechanism such as the knurled area 104 to form a friction fit, adhesive bonding, or induction bonding.

Figure 11:
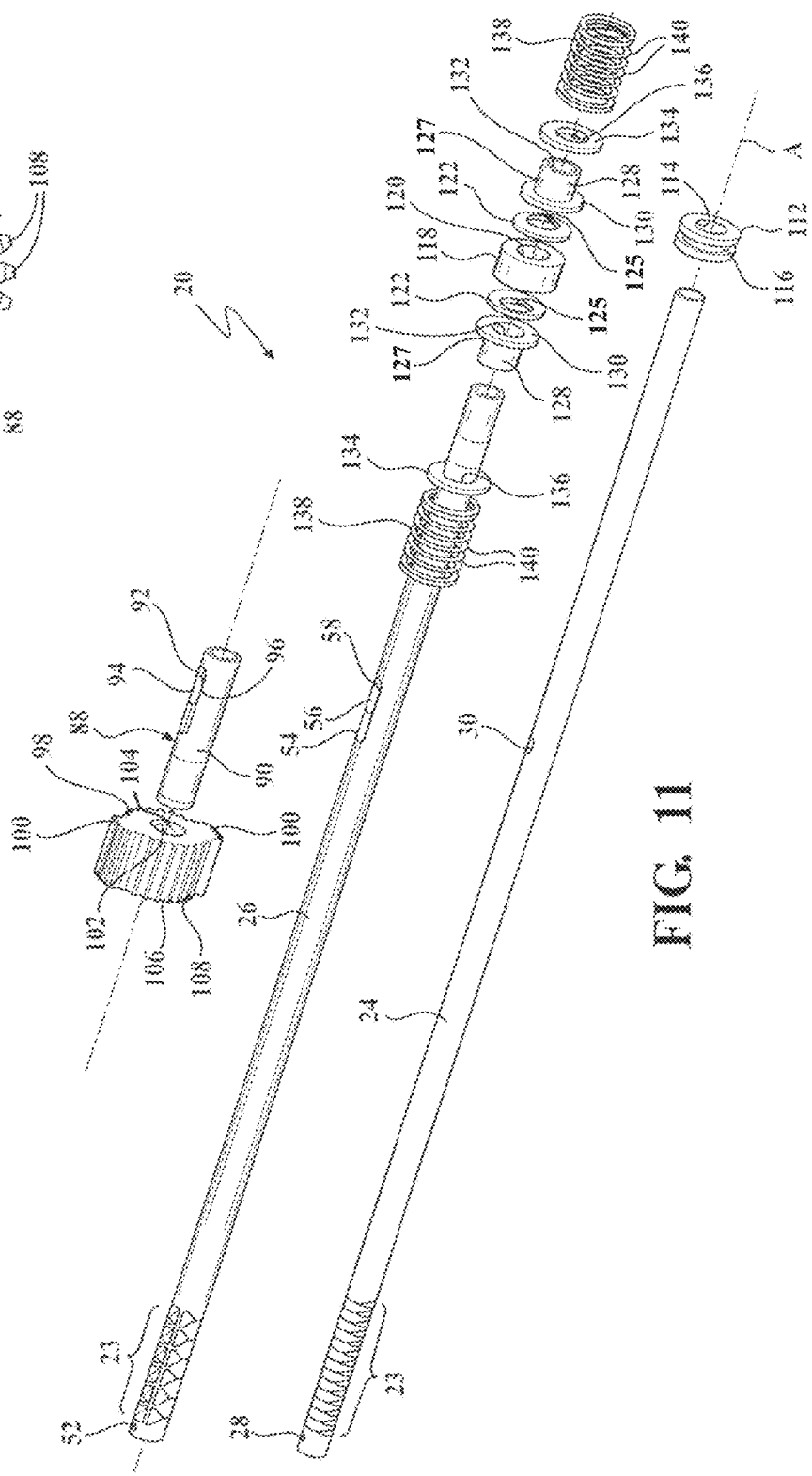
FIG. 11 is an exploded view of the tube assembly of the surgical instrument of FIG. 1.
Figure 12:
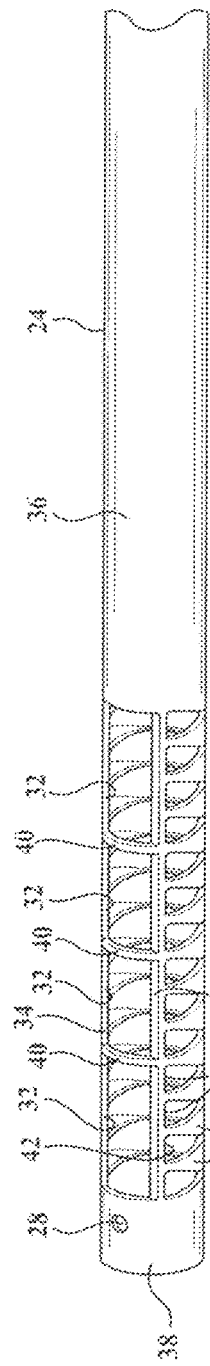
FIG. 12 is a perspective view of an articulating region of an inner tube of the tube assembly of FIG. 11.
Figure 13:
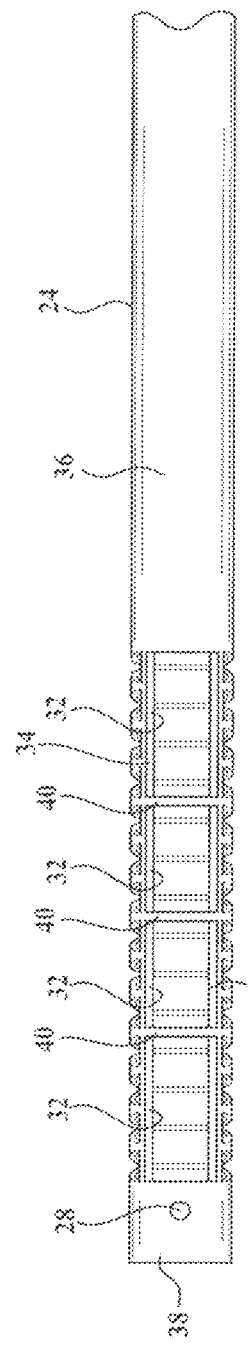
FIG. 13 is a top view of an articulating region of an inner tube of the tube assembly of FIG. 11.
Figure 14:
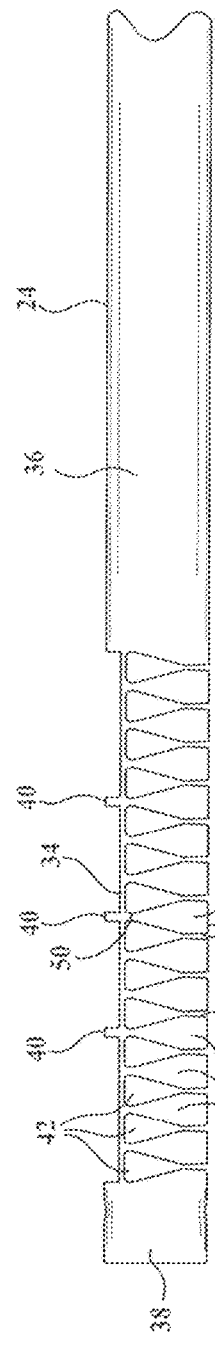
FIG. 14 is a side view of an articulating region of an inner tube of the tube assembly of FIG. 11.
Figure 15:
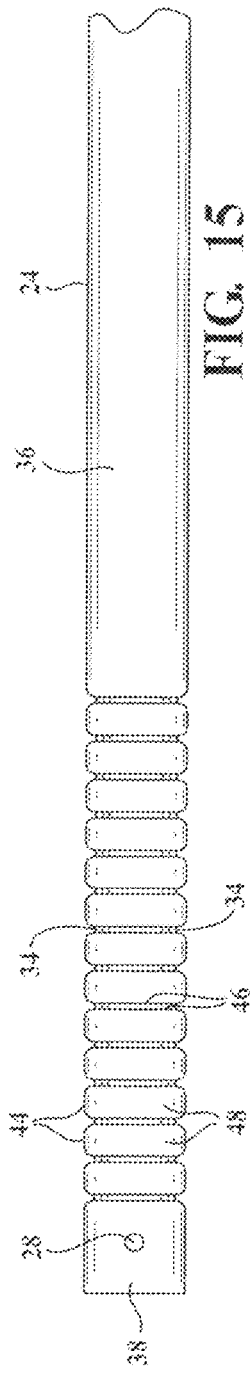
FIG. 15 is a bottom view of an articulating region of an inner tube of the tube assembly of FIG. 11.

Referring to FIG. 11, the articulating tube assembly 20 also includes an inner thrust ring 112 attached to a proximal end of the inner tube 24. The inner thrust ring 112 is generally cylindrical in shape with a generally circular cross-section. The inner thrust ring 112 has an aperture 114 extending axially therethrough to be disposed about the inner tube 24. The aperture 114 is generally circular in shape. The inner thrust ring 112 also has a groove 116 extending radially therein and circumferentially thereabout for a function to be described. The groove 116 has a generally "U" shaped cross-section. It should be appreciated that the inner thrust ring 112 is fixed to the inner tube 24 by a suitable mechanism such as knurling, adhesive bonding, or induction bonding.

The articulating tube assembly 20 also includes an outer thrust ring 118 attached to a proximal end of the outer tube 26. The outer thrust ring 118 is generally cylindrical in shape with a generally circular cross-section. The outer thrust ring 118 has an aperture extending axially therethrough to be disposed about the outer tube 26. The aperture is generally circular in shape. It should be appreciated that the outer thrust ring 118 is fixed to the outer tube 26 by a suitable mechanism such as knurling, adhesive bonding, or induction bonding.

The articulating tube assembly 20 includes one or more spring washers 122 disposed about the outer tube 26 and adjacent each side of the outer thrust ring 118. Each spring washer 122 is generally circular in shape with an aperture 125 extending axially therethrough to be disposed about the outer tube 26. The aperture 125 is generally circular in shape. Each spring washer 122 extends radially and axially. In the illustrated embodiment, each spring washer 122 is of a Bellville type. The articulating tube assembly 20 also includes one or more flanged sleeve 127 disposed about the outer tube 26 and adjacent the washer 122 on each side of the outer thrust ring 118. Each flanged sleeve 126 has a sleeve portion 128 with a generally hollow cylindrical in shape and a generally circular cross-section and a flange portion 130 extending radially from one end of the sleeve portion 128 and having a generally circular shape. Each flanged sleeve 127 includes an aperture 132 extending axially through the sleeve portion 128 and flange portion 130. The aperture 132 has a generally circular cross-section. The articulating tube assembly 20 also includes one or more washers 134 disposed about the outer tube 26 and adjacent each of the flanged sleeves 127. Each washer 134 is generally circular in shape with an aperture 136 extending axially therethrough to be disposed about the outer tube 26. The aperture 136 is generally circular in shape. Each washer 134 extends radially. The articulating tube assembly 20 further includes one or more springs 138 disposed about the outer tube 26 and adjacent each washer 134. Each spring 138 is of a coil type having a plurality of helical shaped coils 140 extending circumferentially and axially.

Figure 20:
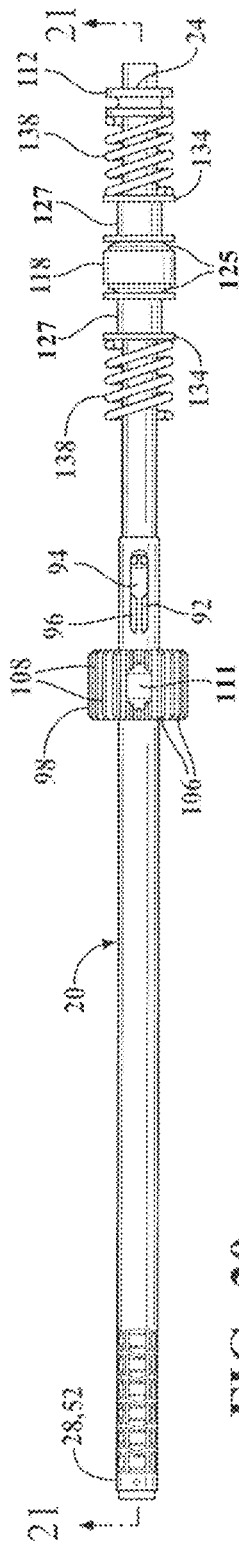
FIG. 20 is a top view of the tube assembly of the surgical instrument of FIG. 11.
Figure 21:
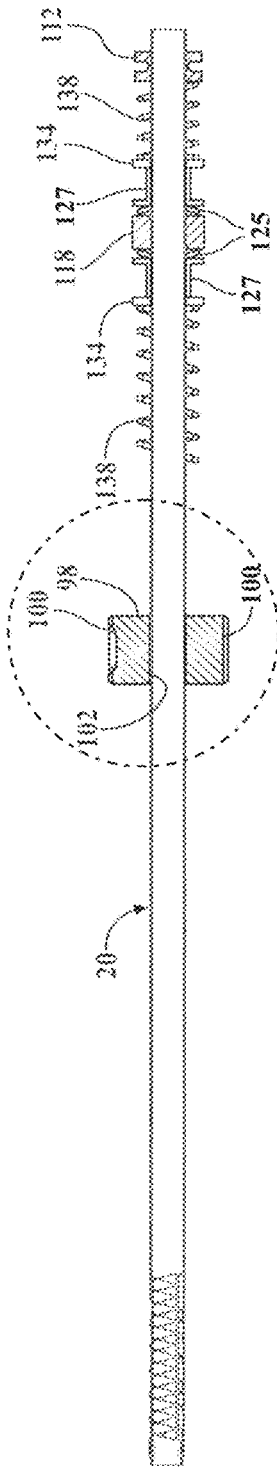
FIG. 21 is a sectional view taken along line 21-21 of FIG. 20.
Figure 22:
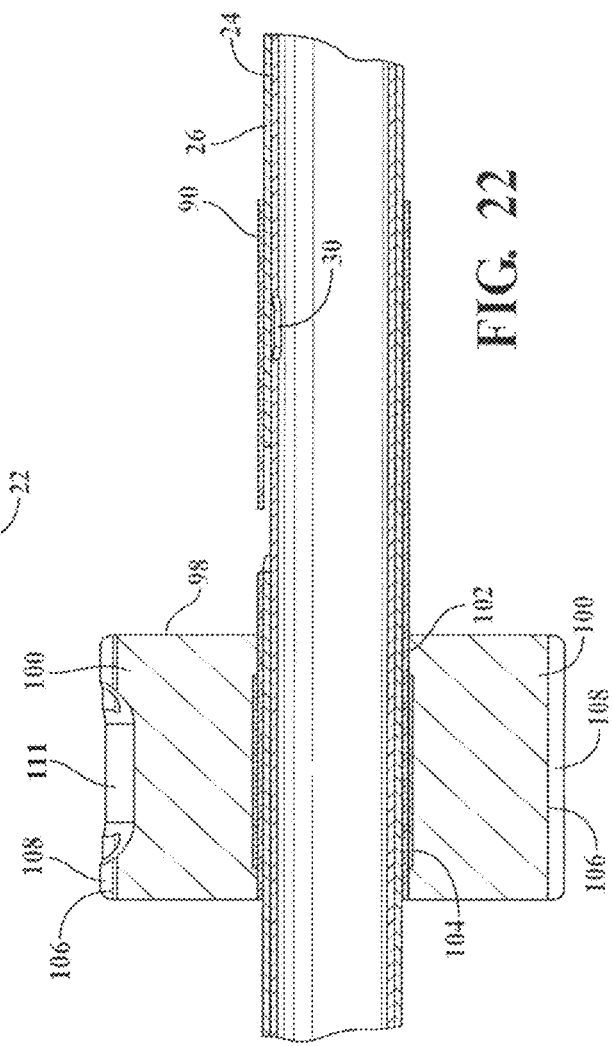
FIG. 22 is an enlarged view of a portion in circle 22 of FIG. 21.
Figure 24:
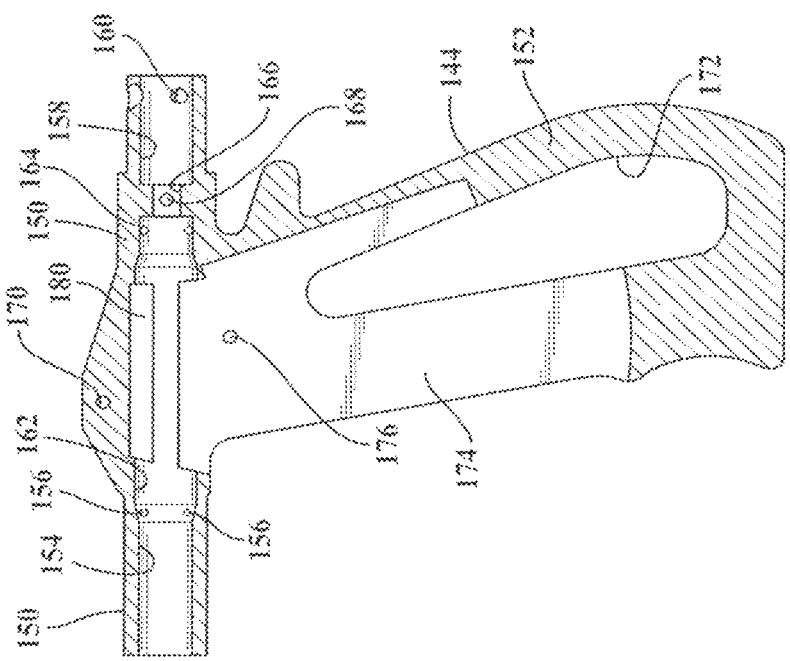
FIG. 24 is a sectional view of the handle of FIG. 23.
Figure 23:
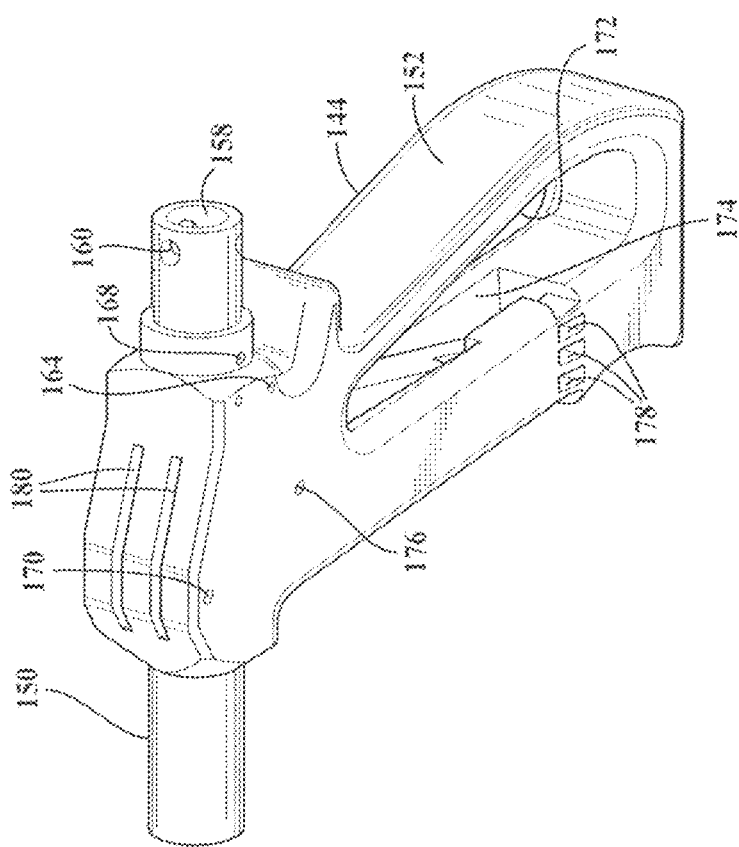
FIG. 23 is a perspective view of a handle of the surgical instrument of FIGS. 1 and 2.
Figure 26:
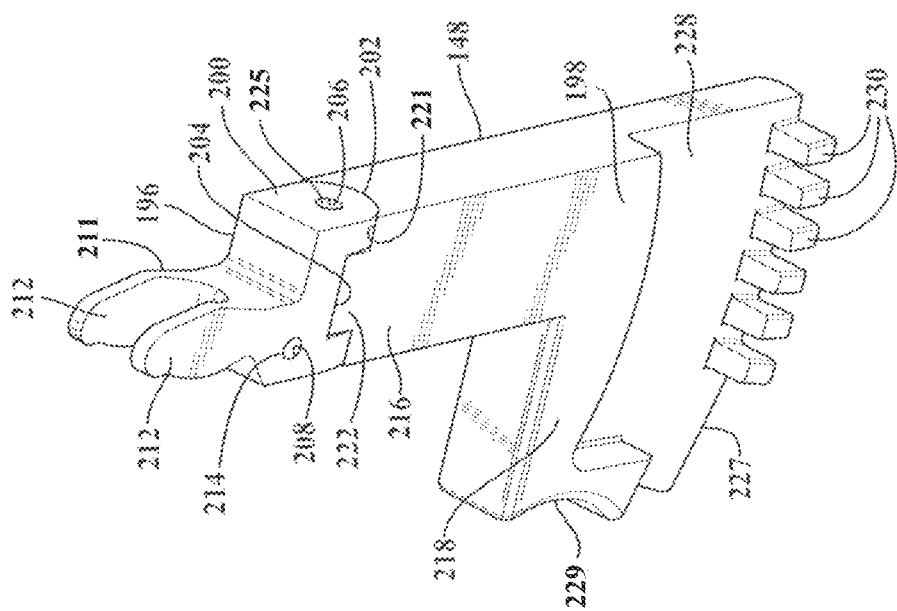
FIG. 26 is a perspective view of a lower trigger for the surgical instrument of FIGS. 1 and 2.
Figure 25:
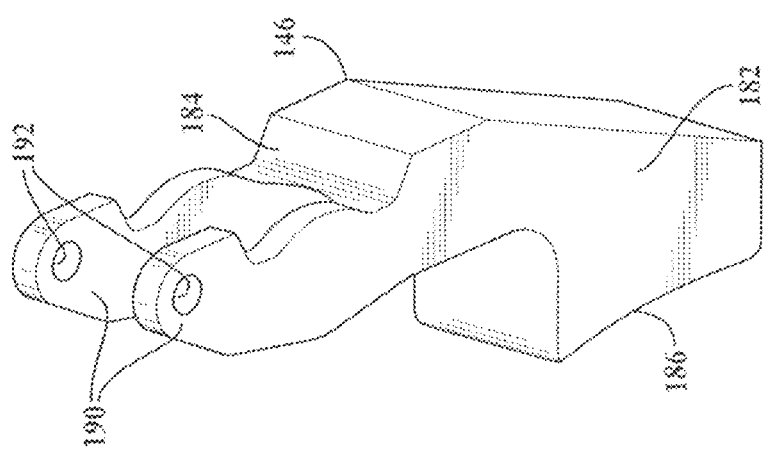
FIG. 25 is a perspective view of an upper trigger for the surgical instrument of FIGS. 1 and 2.

Referring to FIGS. 20 through 22, the assembly of the articulating tube assembly 20 is illustrated. In assembly, the inner tube 24 is inserted into the outer tube 26 and oriented such that the beams 34 of the inner tube 24 are one hundred eighty degrees (180°) opposed to the beams 62 of the outer tube 26. In this embodiment, the apertures 28 and 52 act as an alignment hole through both tubes 24 and 26 such that a fixture pin (not shown) can align and position the tubes 24 and 26. With the pin in place, the distal ends of the tubes 24 and 26 are welded together in one embodiment. In another embodiment, a suitable mechanism such as an adhesive may used to secure the distal ends of the tubes 24 and 26 together. After the distal ends of the tubes 24 and 26 are fixed together, the fixture pin is removed. Once the distal ends of the tubes 24 and 26 are secured to one another, the remainder of the articulating tube assembly 20 is assembled. It should be appreciated that fixing the distal ends of the tubes 24 and 26 together results in the proximal ends of the tubes 24 and 26 being axially and rotationally keyed together to prevent distal relative movement, while still enabling the proximal ends of the tubes 24 and 26 to move axially with respect to each other.

After the distal ends of the tubes 24 and 26 are fixed, a pad 56 of the outer tube 26 is also welded to the proximal end of the inner tube 24. The pad 94 of the angular rotation tube 90 is then welded to the pad 56 of the outer tube 26. The tab 58 of the outer tube 26 is then removed. It should be appreciated that the slot aperture 92 in the angular rotation tube 90 and the aperture 30 in the inner tube 24 allow for this tab 58 to be cut and removed through a suitable mechanism such as a laser (not shown). It should also be appreciated that a second person is not needed to hold the tubes 24, 26, and 90 to perform the assembly. It should further be appreciated that, in another embodiment, a window may be provided to weld the tubes 24, 26, and 90 together. It should yet be appreciated that the pad 94 acts as a leaf spring to allow the pad 56 to be drawn down against the inner tube 24. It should still further be appreciated that a torque applied to angular rotation collar 98 is transferred to the angular rotation tube 90 to which it is attached, and then to the pad 94 of the angular rotation tube 90 because it is constrained within its slot aperture 92. It should yet further be appreciated that, in this way, the tubes 24, 26, and 90 are all rotationally constrained to one another yet the proximal end of the outer tube 26 is free to move axially with respect to the other tubes 24 and 90.

Referring to FIGS. 2 through 5 and 23 through 26, in one embodiment, the actuation assembly 22 is coupled to the articulating tube assembly 20 for moving the inner tube 24 and the outer tube 26 axially relative to each other for articulating the articulating region 23 of the articulating tube assembly 20 between a straight configuration and a curved configuration in only one direction. The actuation assembly 22 includes a handle 144 and one or more triggers 146, 148 coupled to the handle 144 to enable control of the articulating tube assembly 20. The handle 144 includes a tube receiving portion 150 extending axially and a handle portion 152 extending radially downward from the tube receiving portion 150. The tube receiving portion 150 is generally cylindrical shape. The tube receiving portion 150 has a first or forward cavity 154 extending axially rearward therein. The forward cavity 154 is generally cylindrical and circular in cross-sectional shape. The tube receiving portion 150 includes one or more apertures 156 extending radially into the forward cavity 154. The apertures 156 are generally circular in shape and spaced circumferentially. The tube receiving portion 150 also has a second or rearward cavity 158 extending axially forward therein. The rearward cavity 158 is generally cylindrical and circular in cross-sectional shape. The tube receiving portion 150 includes one or more apertures 160 extending radially into the rearward cavity 158. The apertures 160 are generally circular in shape and spaced circumferentially. The apertures 160 are also semi-hemispherical shaped for a function to be described. The tube receiving portion 150 has a central cavity 162 extending axially therein. The central cavity 162 is generally cylindrical and circular in cross-sectional shape. The tube receiving portion 150 includes one or more apertures 164 extending perpendicularly with respect to axis A into the central cavity 162. The apertures 164 are generally circular in shape and spaced symmetrically off-axis. The tube receiving portion 150 also has a passageway 166 extending axially between and communicating with the rearward cavity 158 and the central cavity 162. The passageway 166 has a generally circular cross-section. The tube receiving portion 150 includes an aperture 168 extending radially therethrough. The aperture 168 has a generally circular cross-section. The tube receiving portion 150 further includes an aperture 170 disposed above the central cavity 162 and extending perpendicularly therethrough for a function to be described. It should be appreciated that the passageway 166 is used to support the proximal end of the inner tube 24.

The handle portion 152 extends downwardly and away from the tube receiving portion 150 adjacent the central cavity 162. The handle portion 152 is generally rectangular in shape. The handle portion 152 includes an aperture 172 extending generally perpendicular therethrough. The aperture 172 is generally elongated along the handle portion 152. The handle portion 152 also includes a cavity 174 extending from the forward side toward the rearward side to receive the triggers 146, 148. The cavity 174 is generally rectangular in shape. The cavity 174 communicates with the aperture 172. The handle portion 152 also includes an aperture 176 extending generally perpendicular therethrough and communicating with the cavity 174. The aperture 176 is generally circular in shape. The handle portion 152 may include one or more apertures 178 extending generally perpendicular therethrough and communicating with the cavity 174. The apertures 178 extend through the wall of the handle 144. The apertures 178 are generally rectangular in shape, but may be any suitable shape. The apertures 178 are spaced in a circumferential or arcuate manner for a function to be described. The handle portion 152 may include a pair of slots 180 extending axially along and communicating with the cavity 174. The handle portion 152 and tube receiving portion 150 are made of a rigid material such as plastic. The handle portion 152 and tube receiving portion 150 are integral, unitary, and one-piece.

The triggers 146, 148 include an upper or top trigger 146 and a lower or bottom trigger 148. The upper trigger 146 has a trigger portion 182 extending forward and a flange portion 184 extending upwardly from the trigger portion 182. The trigger portion 182 is generally rectangular in shape, but may be any suitable shape, and includes a trigger surface 186 being generally arcuate in shape to receive a finger of the user. The flange portion 184 includes a pair of opposed flanges 190 extending from the trigger portion 182 and spaced laterally. The flanges 190 include an aperture 192 extending therethrough. The aperture 192 is generally circular in shape. The upper trigger 146 includes a pin 194 extending through the apertures 192 in the flanges 190 and the aperture 170 in the tube receiving portion 150 to pivotally connect the upper trigger 146 to the handle 144. The upper trigger 146 is made of a rigid material such as plastic. The upper trigger 146 is integral, unitary, and one-piece. It should be appreciated that the upper trigger 146 moves the outer tube 26 proximally when actuated causing articulation.

The lower trigger 148 has a connecting portion 196 coupled to the handle portion 152 and a trigger portion 198 coupled to the connecting portion 196. The connecting portion 196 includes a body portion 200 extends axially. The body portion 200 is generally rectangular in shape with a lower surface 202 having a generally arcuate shape. The body portion 200 includes a slot 204 extending radially therein and generally perpendicular thereto. The slot 204 is generally rectangular in shape. The body portion 200 has a first aperture 206 extending axially therethrough and a second aperture 208 extending generally perpendicular therethrough. The apertures 206 and 208 are generally circular in shape. The connecting portion 196 includes a flange portion 211 extending upwardly from the body portion 200. The flange portion 211 includes a pair of opposed flanges 211 extending from the body portion 200 and spaced laterally. The flanges 212 are disposed in the slots 180. The lower trigger 148 includes a pin 214 extending through the aperture 208 in the connecting portion 196 and the aperture 176 in the handle portion 152 to pivotally connect the lower trigger 198 to the handle 144. The pin 214 is generally cylindrical in shape with a generally circular cross-section.

The connecting portion 196 is made of a rigid material such as plastic. The connecting portion 196 is integral, unitary, and one-piece.

The trigger portion 198 has a body portion 216 extending vertically and a finger portion 218 extending forward from the body portion 216. The body portion 216 has an upper surface 221 with a generally arcuate shape. The body portion 216 includes a projection 222 extending upwardly to be disposed in the slot 204 of the connecting portion 196. The trigger portion 198 includes a pin 225 extending through the aperture 206 in the connecting portion 196 and the aperture 176 in the handle portion 152 to pivotally connect the trigger portion 198 to the connecting portion 196. The pin 225 is generally cylindrical in shape with a generally circular cross-section. The finger portion 218 is generally rectangular in shape, but may be any suitable shape, and includes a trigger surface 229 being generally arcuate in shape to receive a finger of the user. The finger portion 218 has a lower surface 227 being generally arcuate in shape. The finger portion 218 may include a recess 228 extending perpendicularly therein. The finger portion 218 may include one or more projections or teeth 230 extending generally perpendicular into the recess 228. The teeth 230 are generally rectangular in shape, but may be any suitable shape. The teeth 230 are spaced in a circumferential or arcuate manner adjacent the lower surface 227 of the finger portion 218 for a function to be described. The trigger portion 198 is made of a rigid material such as plastic. The trigger portion 198 is integral, unitary, and one-piece. It should be appreciated that the lower trigger 148 moves the inner tube 24 distally when actuated pushing the articulating tube assembly 20 to a straight configuration. It should also be appreciated that, another configuration, besides the handle 144 and triggers 146, 148 may be used to push or pull the inner tube 24 and outer tube 26 relative to each other to actuate and articulate the articulating tube assembly 20.

Referring to FIGS. 1 through 5, the assembly of the actuation assembly 22 is illustrated. In assembly, the proximal end of the assembled articulating tube assembly 20 is extended through the forward cavity 154 and into the central cavity such that the inner thrust ring 112 is disposed at the end of the central cavity 162 and the end of the inner tube 24 is disposed in the passageway 166. Pins through apertures 164 and groove 116 secure the inner tube 24 axially, but allows rotation. A split sleeve bushing 232 disposed in the forward cavity 154 extends axially and supports the tube assembly 20. The split sleeve bushing 232 is generally a hollow cylinder having a generally circular cross-sectional shape to allow the articulating tube assembly 20 to extend therethrough. The split sleeve bushing 232 may include a groove 234 to receive pins 236, which retain the bushing 232 and resist distal spring 138 in FIG. 11. The pins 236 are generally cylindrical in shape with a generally circular cross-section. The pins 236 extend through apertures 237 in the tube receiving portion 250 to secure the inner tube axially in the handle 144, but enables rotation.

The upper trigger 146 is disposed in the cavity 174 and the flanges 190 are extended around the articulating tube assembly 20 between the washer 134 and flanged sleeve 127 and upwardly into the slots 180 such that the apertures 192 and 170 align. The pin 194 is then extended through the aperture 170 and apertures 192 to pivotally connect the upper trigger 146 to the actuation assembly 22. It should be appreciated that the articulating tube assembly 20 extends axially through a space between the flanges 190 of the upper trigger 146. It should also be appreciated that the pin 194 allows pivotal movement of the upper trigger 146 forward and rearward and the flanges 190 and slots 180 guide the movement.

Once the connecting portion 196 and trigger portion 198 are assembled together for the lower trigger 148, the lower trigger 148 is disposed in the cavity 174 and the flanges 212 are extended around the articulating tube assembly 20 between the flanged sleeve 127 and washer 134 and upwardly into the slots 180 such that the apertures 208 and 176 align. The pin 214 is then extended through the apertures 208 and aperture 176 to pivotally connect the lower trigger 148 to the actuation assembly 22. It should be appreciated that the articulating tube assembly 20 extends axially through a space between the flanges 212 of the lower trigger 148. It should also be appreciated that the pin 214 allows pivotal movement of the lower trigger 148 forward and rearward and the flanges 190 and slots 180 guide the movement. It should further be appreciated that the pin 225 allows pivotal movement of the trigger portion 198 of the upper trigger 146 perpendicularly from side to side.

As illustrated in FIGS. 1 through 5, the working tool 12 is inserted into the surgical instrument 10. The shaft portion 14 is inserted into the rearward cavity of the actuation assembly 22 and extended axially through the inner tube 24. The insertion portion 16 is also inserted into the rearward cavity 158 of the actuation assembly 22 and extended axially until the flange portion 17 abuts the rear of the actuation assembly 22. When this occurs, a spherically shaped ball 238 a is disposed in one of the apertures 160 engages one of a plurality of detents 238 b in the insertion portion 16 as illustrated in FIG. 5. A collar 239 may be disposed about the proximal end of the tube receiving portion 250. The collar 239 is generally cylindrical with a generally circular cross-section and is pushed against the ball 238 a by a spring 239 c. The collar 239 has an inner ramp 239 a that engages the ball 238 a to prevent rotation of the working tool 12 and lock the working tool 12 in place relative to the tube receiving portion 250 of the actuation assembly 22. It should be appreciated that a plurality of detents 238 b may be provided for multiple positions to vary amount of exposure of the distal end of the working tool 12 out of the distal end of the articulating tube assembly 20. It should also be appreciated that the connecting portion 18 of the working tool 12 may be connected to a power source (not shown).

In operation, when a finger of the user pulls the upper trigger 146 into the handle 144, the lower trigger 148 moves out, and the outer tube 26 is pushed proximally with respect to the inner tube 24, causing the tube assembly 20 to articulate as described below until the bottoming segments 44 of the inner tube 24 bottom on each other. While in this state, the lower trigger 148 can pivot to the side about the pin 225 and engage the bottom trigger teeth 230 into the slots 180 in the handle portion 152 of the handle 144, locking the instrument 10 in this condition. Pushing the lower trigger 148 to the opposite side disengages these teeth 230, unlocking the articulation control. Pushing the lower trigger 148 now into the handle 144 causes the upper trigger 146 to move out and moves the outer tube 26 distally with respect to the inner tube 24, causing the tube assembly 20 to articulate as described below until the bottoming segments 72 of the outer tube 26 bottom on each other.

When a force from the lower trigger 148 is applied to the proximal end of the outer tube 26 pushing it distally relative to the inner tube 24, the beams 62 of the outer tube 26 are put in compression and the beams 34 of the inner tube 24 are put in tension. This loading causes a curve in the articulating region 23 of the articulating tube assembly 20 toward the beams 34 of the inner tube 24, which are in tension. The articulating region 23 of the articulating tube assembly 20 curves until the bottoming segments 72 of the outer tube 26 bottom on each other, closing the small gap between these bottoming segments 72. With a significant load applied in this bottomed condition, the articulating region 23 of the articulating tube assembly 20 is rigid as there is considerable axial loading about the circumference holding the bottoming segments 72 in place. Because there are relatively few and narrow gaps between bottoming segments 72 of the outer tube 26, it should be appreciated that relatively minimal tube curvature occurs. As this force is increased, the articulating tube assembly 20 becomes increasingly rigid in a nearly straight condition.

When an opposite force is applied to the proximal end of the outer tube 26, pulling it proximally relative to the inner tube 24, the beams 62 of the outer tube 26 are placed in tension while the beams 34 of the inner tube 24 are placed in compression. This loading causes a curve in the articulating region 23 of the articulating tube assembly 20 toward the beams 62 of the outer tube 26, which are in tension. The articulating region 23 of the articulating tube assembly 20 curves until the bottoming segments 44 of the inner tube 24 bottom on each other, closing the gap between these bottoming segments 44. With a significant load applied in this bottomed condition, the articulating tube assembly 20 is rigid as there is considerable axial loading about the circumference holding the bottoming segments 44 in place. Because there are relatively more and wider gaps between the bottoming segments 72 of the outer tube 26, it should be appreciated that considerable curvature of the articulating region 23 of the articulating tube assembly 20 occurs. As this force is increased, the articulating region 23 of the articulating tube assembly 20 becomes increasingly rigid in a substantially curved condition. The compliance allowed by the springs 122 enables the bottoming segments 44 and 72 to remain under load and so the tubes 24, 26 are rigid while the trigger teeth 230 are engaged in the apertures 178.

Because this articulating tube assembly 20 now enables the ability to do work around a corner, the users' ability to safely perform this work will now be limited by their ability to see the working tip. In some versions, the surgical instrument 10 may be configured to include a tool view or viewing assembly, generally indicated at 240 in FIGS. 1 and 2, which is an option provided for the user. The viewing assembly 240 may include relatively small visualization and illumination elements at its distal tip that are able to present the user real time video from their perspective at the tip of the viewing assembly 240. In certain circumstances where the working tool 12 must be advanced beyond the view of other visualization tools (e.g. endoscope or surgical microscope), the viewing assembly 240 can be slipped over the articulating tube assembly 20 of the surgical instrument 10. Other configurations are also contemplated such that the viewing assembly 240 may be disposed within the articulating tube assembly 20 or integral with one or more components of the articulating tube assembly 20.

Referring to FIGS. 1 through 5, the viewing assembly 240 includes a main tube 242 extending axially. The main tube 242 is a generally hollow cylinder and has a generally circular cross-sectional shape. The main tube 242 has a diameter greater than a diameter of the outer tube 26 such that the outer tube 26 is disposed within the main tube 242. The main tube 242 extends axially between a proximal end and a distal end. The main tube 242 has an axial length shorter than an axial length of the outer tube 26 such that the outer tube 26 extends past a distal end of the main tube 242 when the outer tube 26 is disposed within the main tube 242. The main tube 242 is made of a metal material such as stainless steel or a non-metallic material such as a composite depending on the application. It should be appreciated that the wall thickness of the main tube 242 is relatively thin such as approximately 0.1 to approximately 0.5 millimeters (mm). It should also be appreciated that the diameter of the main tube 242 has a relatively small diameter so as to work in a small opening of the patient and to prevent the user's view from being obstructed.

The main tube 242 also includes a flexible region 23a along a length thereof. The flexible region 23a is disposed between the proximal end and distal end of the main tube 242. The flexible region 23a may have any suitable configuration to allow it to flex such as apertures 245 extending radially through and circumferentially across a wall of the main tube 242. The apertures 256 are spaced axially along the flexible region 23a of the main tube 242. It should be appreciated that the apertures 256 may be cut in the main tube 242 by a laser or wire EDM (not shown). It should also be appreciated that the main tube 242 is capable of fitting over the articulating tube assembly 20 and the flexible region 23a of the main tube 242 tends to align when seated on the surgical instrument 10 with the articulating region 23 of the articulating tube assembly 20.

Figure 27:
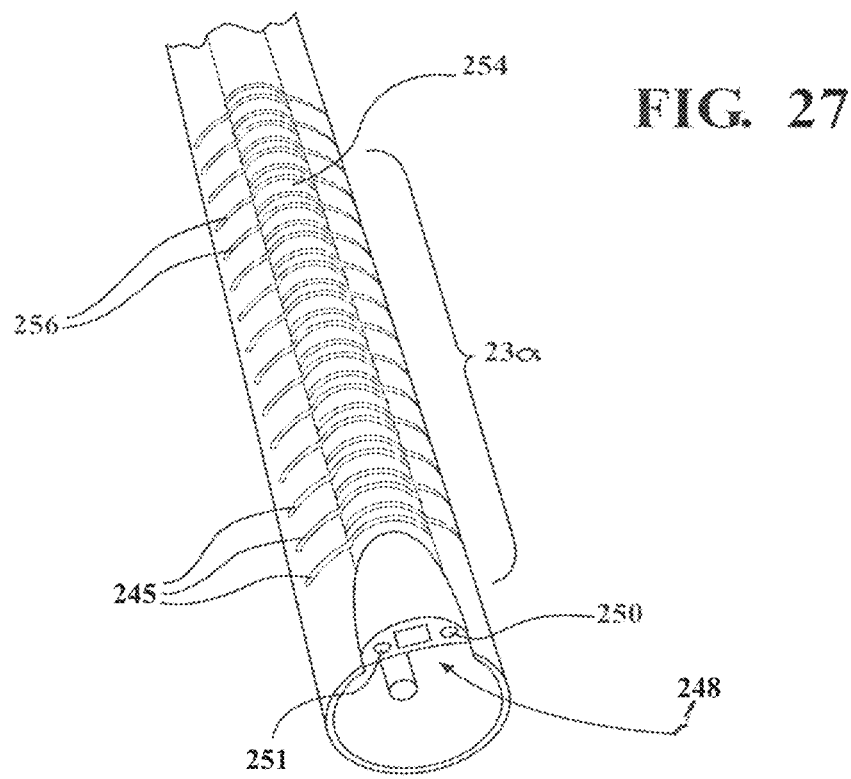
FIG. 27 is a perspective view of a portion of a tool view assembly of the surgical instrument of FIGS. 1 and 2.
Figure 28:
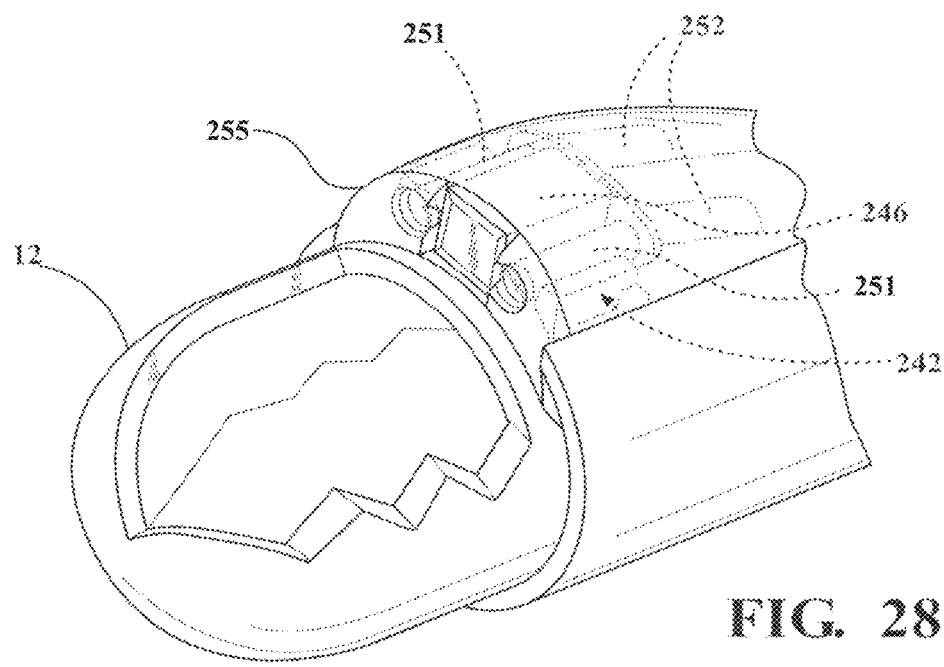
FIG. 28 is a perspective view of an end of a tool view assembly of the surgical instrument of FIGS. 1 and 2.
Figure 33:
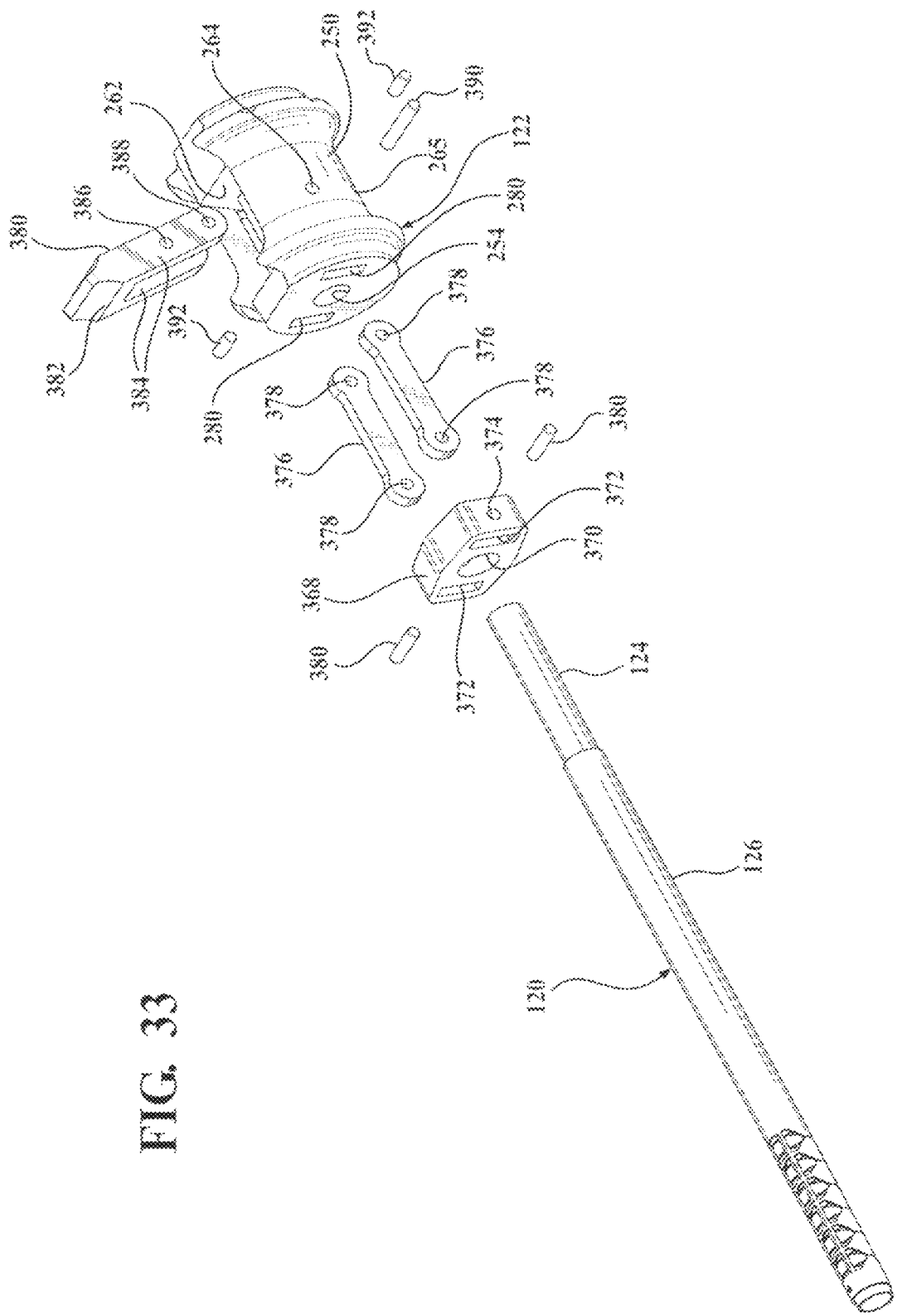
FIG. 33 is an exploded perspective view of an actuation assembly of the surgical instrument of FIGS. 29-32.

Referring to FIGS. 27 and 28, the viewing assembly 240 may include at least one imaging element 246 located at a distal end of the main tube 242. The imaging element 246 is a camera, video camera, or of a camera chip, with wires (not shown) to the camera. The imaging element 246 is connected to the distal end of the main tube 242 by a suitable mechanism such as an adhesive or epoxy. The viewing assembly 240 may include an illumination assembly, generally indicated at 248, for illuminating the surgical site at a distal end of the articulating tube assembly 20. The illumination assembly 248 includes one or more illuminators 250 such as light emitting diodes (LEDs) located at the distal end of the main tube 242. As illustrated, one illuminator 250 is located on one side of the imaging element 246 and another illuminator 250 is located on the other side of the imaging element 246. The illuminators 250 are connected to the distal end of the main tube 242 by a suitable mechanism such as an adhesive or epoxy. The illuminators 250 are also connected by wires 252 to a power source (not shown). It should be appreciated that the illuminators 250 may be configured as plastic optical fibers coupled to a remote light source (not shown).

The viewing assembly 240 may include a shroud 255 attached to the main tube 242 to cover the imaging element 246, illuminators 250, and wires 252. The shroud 255 extends axially along the main tube 242 from the distal end toward the proximal end and over the articulating region 23. The shroud 255 has a generally arcuate configuration to form a passageway for the wires 252 and camera wires (not shown). The shroud 255 may be connected to the main tube 242 by a suitable means such as welding. The shroud 255 is made of a metal material such as stainless steel or a non-metallic material such as a composite depending on the application.

The shroud 255 also includes a flexible region 23a along a length thereof. The flexible region 23a is disposed between the proximal end and distal end of the shroud 255. The flexible region 23a may have any suitable configuration to allow it to flex such as apertures 256 extending radially through and circumferentially across a wall of the shroud 255. The apertures 256 are spaced axially along the flexible region 23a of the shroud 255. It should be appreciated that the apertures 256 may be cut in the shroud 255 by a laser or wire EDM (not shown). It should also be appreciated that the main tube 242 and shroud 255 flex left to right, but not up and down to prevent the wires 252 from being compressed and extended.

The viewing assembly 240 also includes a connector 258 having a distal end connected to a proximal end of the main tube 242. The connector 258 extends axially and has a slot 263 extending radially therethrough to form a generally "U" shape. The connector 258 has a diameter larger than a diameter of the tube receiving portion 150 of the actuation assembly 22. It should be appreciated that the collar 98 is disposed in the slot 263 and the amount of rotation is limited by the protrusions 100 on the collar 98 to prevent flexing at the six o'clock and twelve o'clock positions, but allowing flexing at the three o'clock and nine o'clock positions.

The viewing assembly 240 includes a grasping member 267 disposed at a proximal end of the connector 258. The grasping member 267 is generally circular in shape. The grasping member 267 also includes an aperture 263 extending axially therethrough to allow the grasping member 267 to be disposed over and about the tube receiving portion 150 of the actuation assembly 22. The grasping member 267 has an outer surface with a plurality of grooves 269 and a plurality of gripping members 266 extending axially and spaced circumferentially. The grooves 269 and gripping members 266 are generally arcuate shaped, but may be any suitable shape. It should be appreciated that the grasping member 267 is coupled to the tube receiving portion 150 of the actuation assembly 22 to form a friction fit. It should be appreciated that the viewing assembly 240 may be manually moved axially by a user.

In operation, the viewing assembly 240 allows real time video to be presented to the user on a video monitor (not shown) for a primary view, and in another embodiment, as a small picture-in-picture in the corner of the screen of the video monitor for a secondary view for an endoscope (not shown), or in the corner of their microscope image. In this way, the user maintains the "global view" they currently have with their current visualization tools, while being provided a perspective deep within the surgical site very near the tip of the working tool 12. In one embodiment, the viewing assembly 240 may be advanced or retracted along the length of the articulating tube assembly 20 such that in the fully retracted position, the distal tip of the viewing assembly 240 is proximal of the articulating region 23 of the articulating tube assembly 20, and in more advance positions the distal tip of the viewing assembly 240 is just distal of the articulating region 23 or, in even more advanced positions, the distal tip of the viewing assembly 240 is distal of the tip of the working tool 12.

One advantage of the present invention is that the surgical instrument provides a primary view in one embodiment and a secondary local view in another embodiment for a surgeon. Yet another advantage of the present invention is that the surgical instrument includes imaging elements at a distal tip to provide the secondary local view for the surgeon. Still another advantage of the present invention is that the surgical instrument includes an imaging element capable of being moved along an axis of the instrument. A further advantage of the present invention is that the surgical instrument includes an illumination device to provide illumination at the surgical site.

Referring to FIGS. 29 through 35, another embodiment, according to the present invention, of the surgical instrument 10 is shown. Like parts of the surgical instrument 10 have like reference numerals increased by one hundred (100). In this embodiment, the surgical instrument 110 includes the articulating tube assembly 120 and a new actuation assembly 122 coupled to the articulating tube assembly 120 for moving the inner tube 124 and the outer tube 126 axially relative to each other for articulating the articulating region 123 of the articulating tube assembly 120 between a straight configuration and a curved configuration in only one direction. It should also be appreciated that, at the proximal end of the surgical instrument 110, there are components that enable the surgeon to control the articulation and allow the surgical instrument 110 to attach to and be driven by a drive assembly (not shown).

The actuation assembly 122 includes a handle 244 including a tube receiving portion 250 extending axially. The tube receiving portion 250 is generally cylindrical shape. The tube receiving portion 250 has a first or forward cavity 254 extending axially rearward therein. The forward cavity 254 is generally cylindrical and circular in cross-sectional shape. The tube receiving portion 250 also has a second or rearward cavity 259 extending axially forward therein. The rearward cavity 259 is generally cylindrical and circular in cross-sectional shape. The rearward cavity 259 communicates axially with the forward cavity 254. The tube receiving portion 250 includes one or more apertures 260 extending perpendicularly into the rearward cavity 259. The apertures 260 are generally circular in shape and spaced symmetrically about the axis. The tube receiving portion 250 has a central cavity 262 extending radially and axially therein. The central cavity 262 is generally rectangular in shape. The tube receiving portion 250 includes one or more apertures 264 extending radially into the central cavity 262. The apertures 264 are generally circular in shape and spaced circumferentially. The tube receiving portion 250 further includes an aperture 265 disposed below the central cavity 262 and extending radially therethrough for a function to be described. The tube receiving portion 250 may include a pair of slots 280 extending axially therein and communicating with the central cavity 262. One of the slots 280 is spaced radially from one side of the forward cavity 254 and another slot 280 is spaced radially from an opposed side of the forward cavity 254. The tube receiving portion 250 is made of a rigid material such as plastic. The tube receiving portion 250 is integral, unitary, and one-piece. It should be appreciated that the forward cavity 254 is used to support the proximal end of the inner tube 124.

The actuation assembly 122 also includes a collar 368 connected to a proximal end of the outer tube 126. The collar 368 is generally rectangular in shape. The collar 368 includes an aperture 370 extending axially therethrough. The aperture 370 is generally circular in shape. The collar 368 also includes a plurality of apertures 372 extending axially therethrough. The apertures 372 are generally rectangular in shape. One of the apertures 372 is spaced radially from one side of the aperture 370 and another aperture 372 is spaced radially from an opposed side of the aperture 370. The collar 368 further includes one or more apertures 374 extending radially therethrough and communicating with the apertures 372. The apertures 374 are generally circular in shape. One of the apertures 374 is located on one side of the collar 368 and communicating with the aperture 372 and another aperture 374 is located on another side of the collar 368 and communicating with the aperture 372. It should be appreciated that the aperture 370 has a diameter to receive the outer tube 126 to form a friction fit, adhesive bond, or induction bond therebetween.

The actuation assembly 122 includes one or more links 376 connected to the collar 368. The links 376 extend axially. The links 376 are generally rectangular in shape. The links 376 have an aperture 378 extending through each end thereof. The distal end of the links 376 is disposed in the apertures 372 of the collar 368 until the apertures 378 and 374 are aligned. The actuation assembly 122 includes one or more pins 381 to connect the distal end of the links 376 to the collar 368. The pins 381 are generally cylindrical in shape with a generally circular cross-section. The pins 381 are disposed in the apertures 374 and 378 to connect the links 376 to the collar 368. It should be appreciated that the proximal end of the links 376 are disposed in the slots 280 of the tube receiving portion 250.

The actuation assembly 122 also includes a lever 380 connected to the proximal end of the links 376. The lever 380 has a generally inverted "U" shape. The lever 380 has a top portion 382 and a pair of side portions 384 being spaced and extending from the top portion 382. The side portions 384 include an upper aperture 386 and a lower aperture 388 extending therethrough. The upper aperture 386 is spaced from the lower aperture 388. The side portions 384 are disposed in the central cavity 262 until the apertures 388 and 265 are aligned and the apertures 386 and 264 are aligned. The actuation assembly 122 includes one or more pins 390 and 392 to connect the side portions 384 of the lever 380 to the proximal end of the links 376. The pins 390 and 392 are generally cylindrical in shape with a generally circular cross-section. The pin 390 has a length greater than a length of the pins 392. The pins 390 are disposed in the apertures 388 and 265 to connect the lever 380 to the tube receiving portion 250 of the handle 244 and the pins 392 pass through the apertures 264 and are disposed in the apertures 386 and 378 to connect the lever 380 to the links 376.

Figure 34:
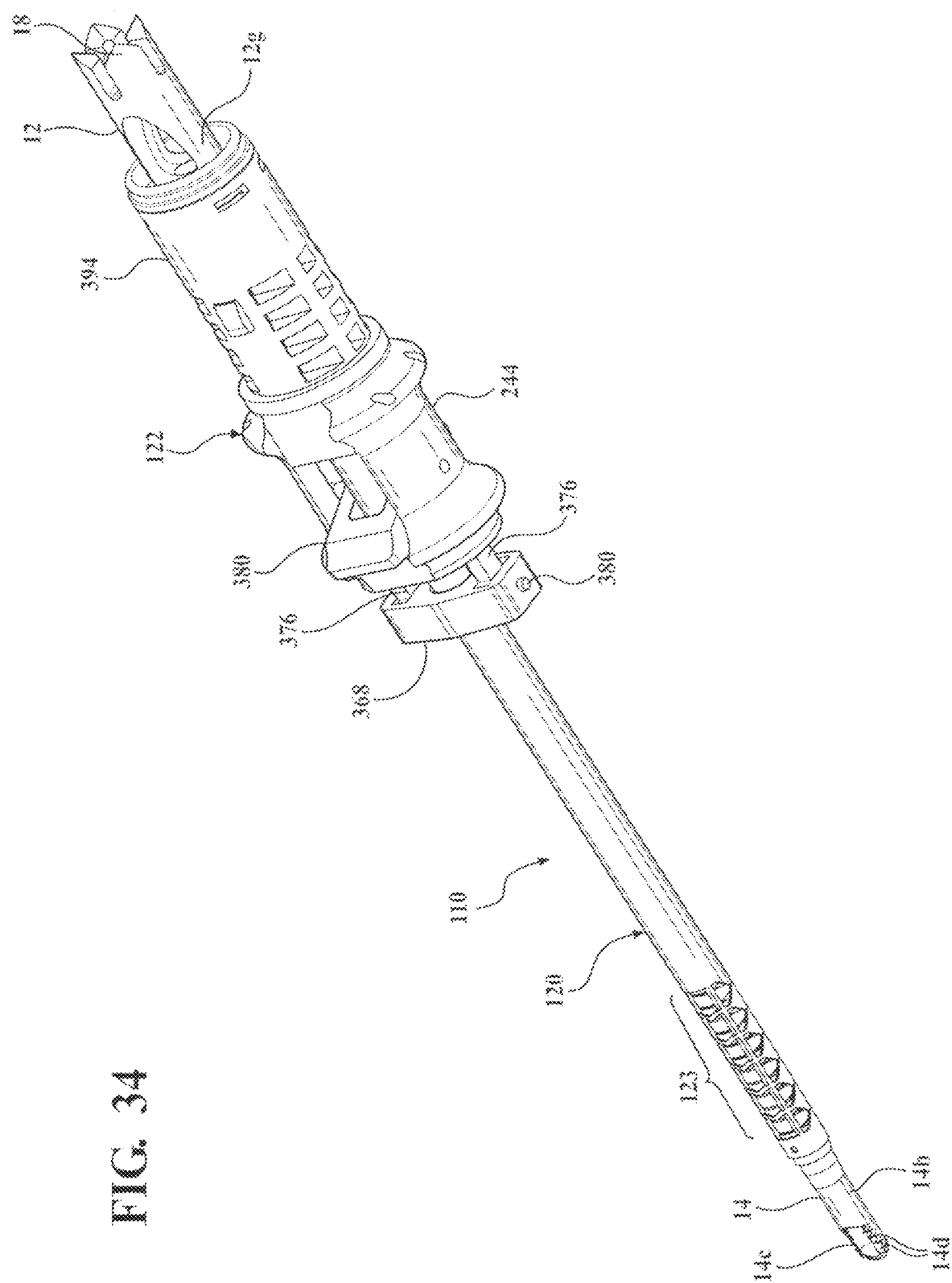
FIG. 34 is a perspective view of the surgical instrument of FIG. 28 illustrated in operational relationship with a working tool.
Figure 35:
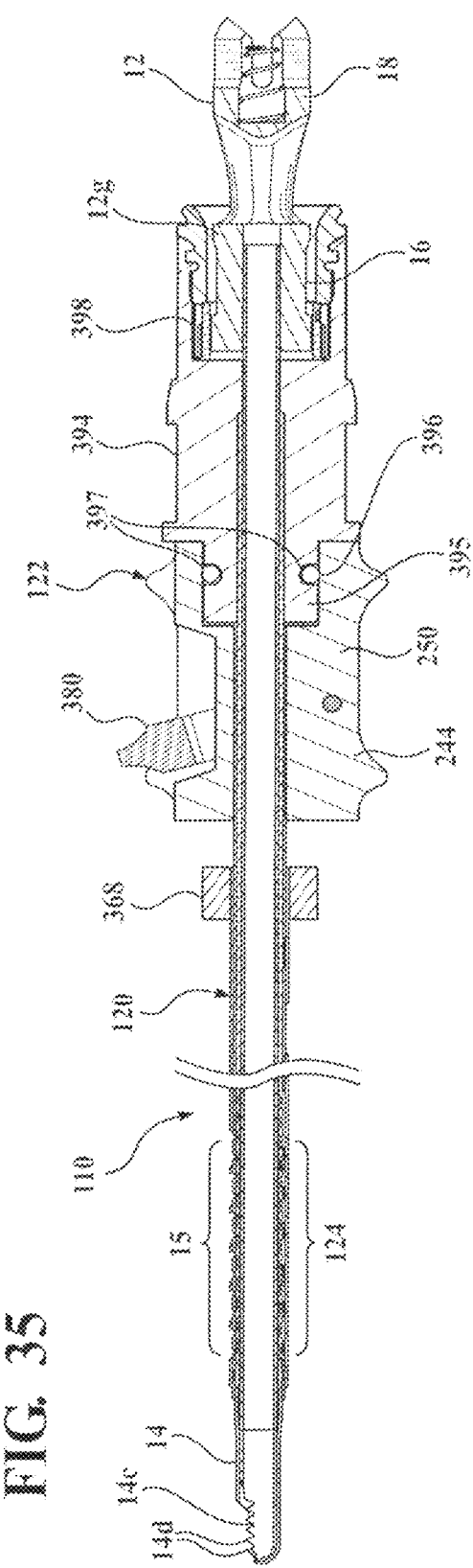
FIG. 35 is a sectional view of the surgical instrument and working tool of FIG. 34.
Figure 37:
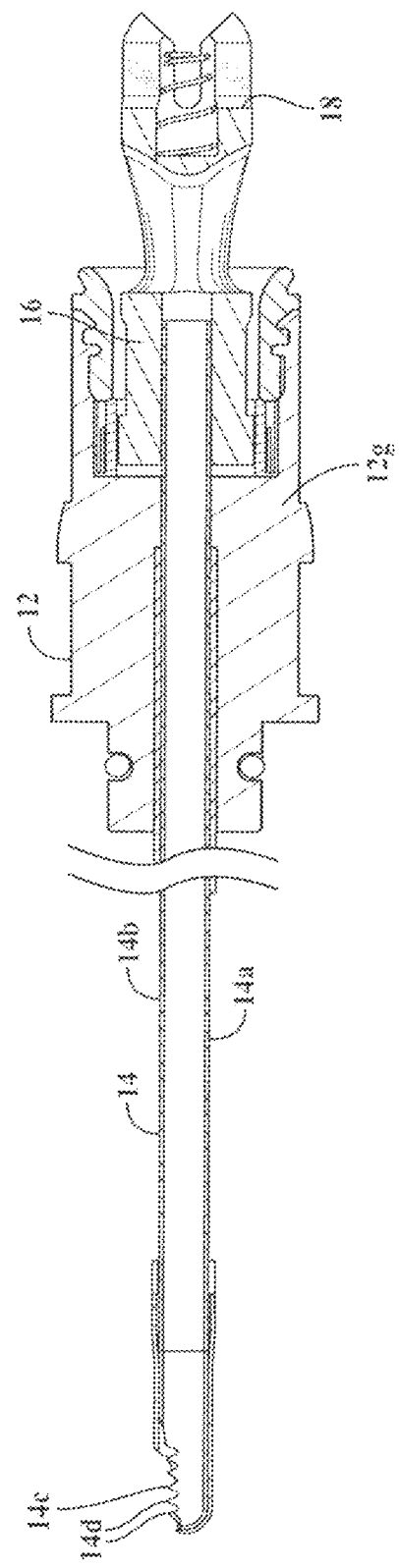
FIG. 37 is a sectional view of the working tool of FIGS. 34 through 36.
Figure 36:
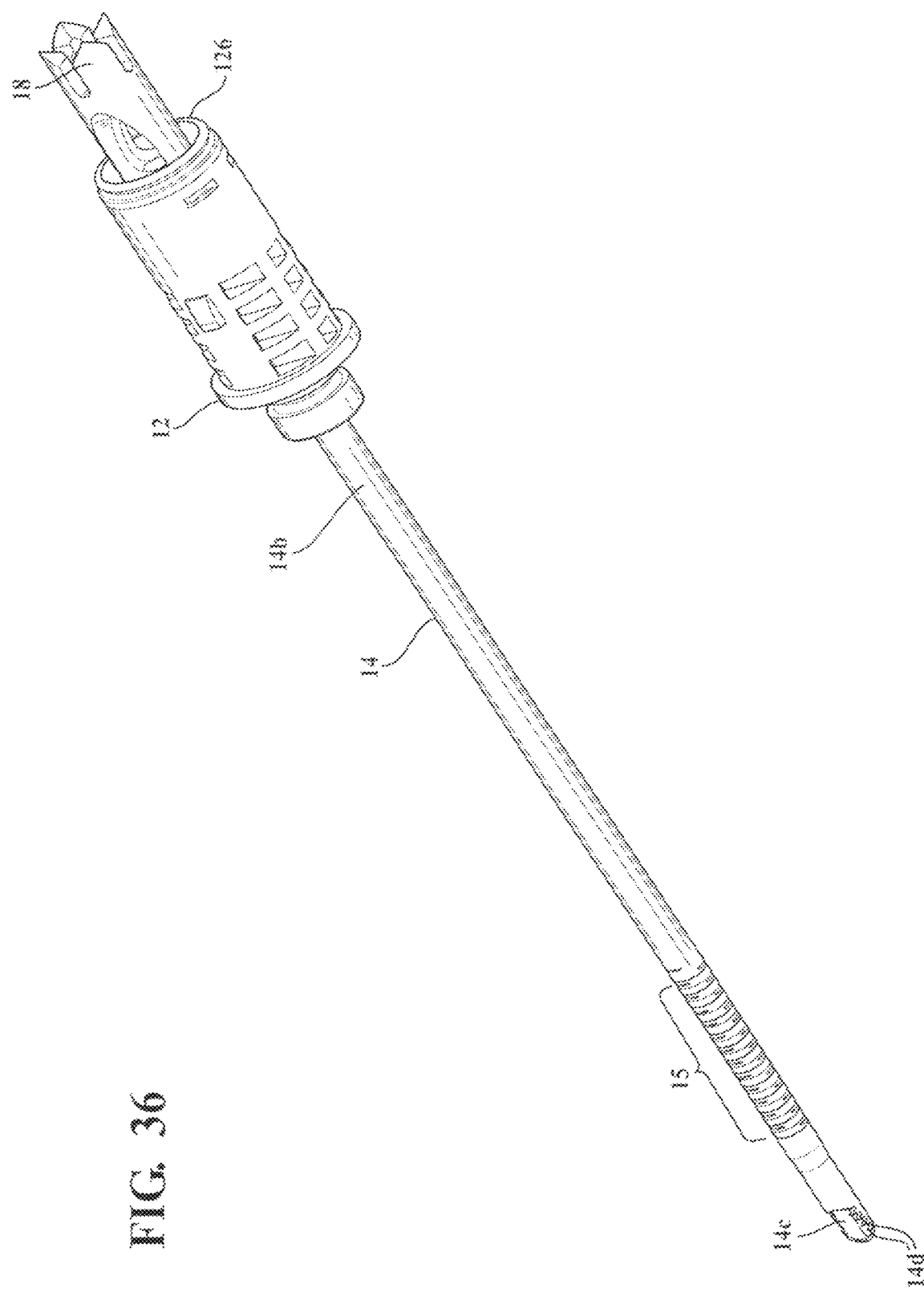
FIG. 36 is a perspective view of the working tool of FIGS. 34 and 35.

Referring to FIGS. 34, 35, and 37, the surgical instrument 110 is illustrated with one of the working tools 12. The surgical instrument 110 is capable of receiving the working tool 12 and releaseably securing the working tool 12 by a friction fit. The working tool 12 is a flexible shaver 12g for use on the patient. In one embodiment, the flexible shaver 12g may include a housing hub 394 disposed in a proximal end of the handle 244 of the actuation assembly 122. The housing hub 394 is generally cylindrical in shape with a generally circular cross-section. The housing hub 394 extends axially from a proximal end to a distal end. The housing hub 394 has a reduced diameter plug portion 395 at the distal end. The plug portion 395 includes a groove 396 to receive pins 397 that extend through the handle 244 to lock the housing hub 394 to the handle 244. The housing hub 394 also includes a cavity 398 extending axially into the proximal end thereof. The cavity 398 is generally cylindrical in shape with a generally circular cross-section. The housing hub 394 is integral, unitary, and one-piece.

The flexible shaver 12g also has a shaft portion 14 and a flexible region 15 along the shaft portion 14 near a distal end. The shaft portion 14 includes an inner tube 14a and an outer tube 14b. The outer tube 14b is fixedly connected to the housing hub 394. The flexible shaver 12g also have a generally cylindrical enlarged insertion portion 16 along the shaft portion 14 near a proximal end and a connecting portion 18 extending axially away from the proximal end of the insertion portion 16 for connection to a power source and suction (not shown). The inner tube 14a extends through the insertion portion 16 and is connected to the connecting portion 18. It should be appreciated that the connecting portion 18 is a cutter driveshaft that oscillates by rotating two to five turns and then changes direction.

The outer tube 14b has an opening 14c at the distal end thereof. In one embodiment, the inner tube 14a has a plurality of teeth 14d at its distal end to form a cutter that rotates relative to the outer tube 14b. It should be appreciated that the opening 14c in the outer tube 14b forms a window where tissue is pulled in and cut by the teeth 14d of the inner cutter.

Figure 38:
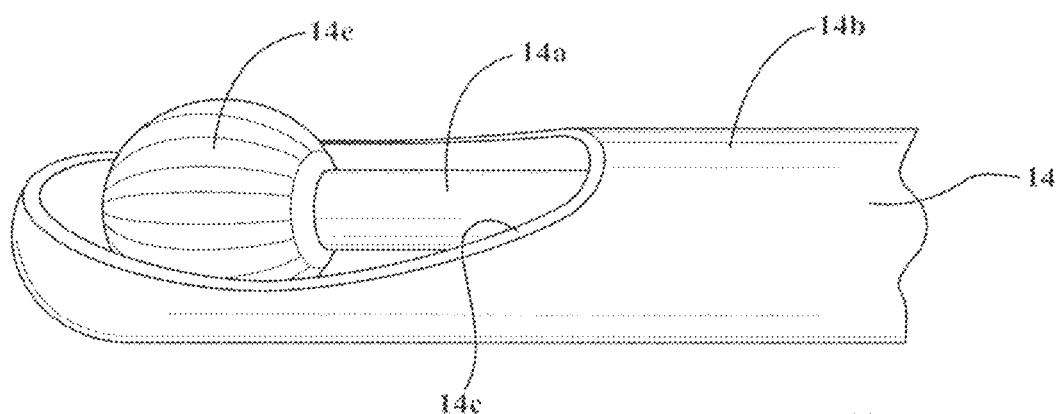
FIG. 38 is an enlarged view of a distal end of the working tool of FIGS. 34 through 36.

Referring to FIG. 38, the inner tube 14a has a bur 14e at its distal end to form a spinning bur. It should be appreciated that the opening 14c in the outer tube 14b allows the cutting by the spinning bur 14e of the inner tube 14a.

Figure 39:
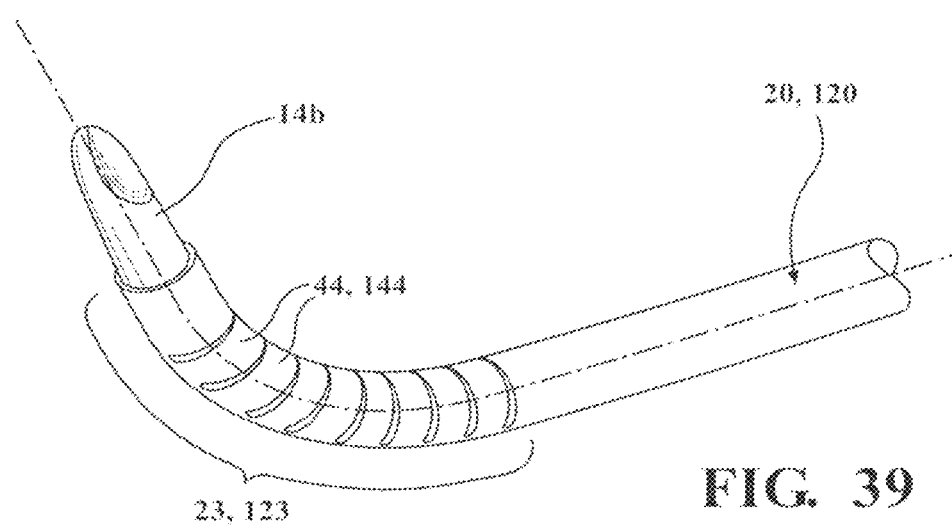
FIG. 39 is a perspective view of the distal end of the working tool of FIGS. 34 through 36.
Figure 40:
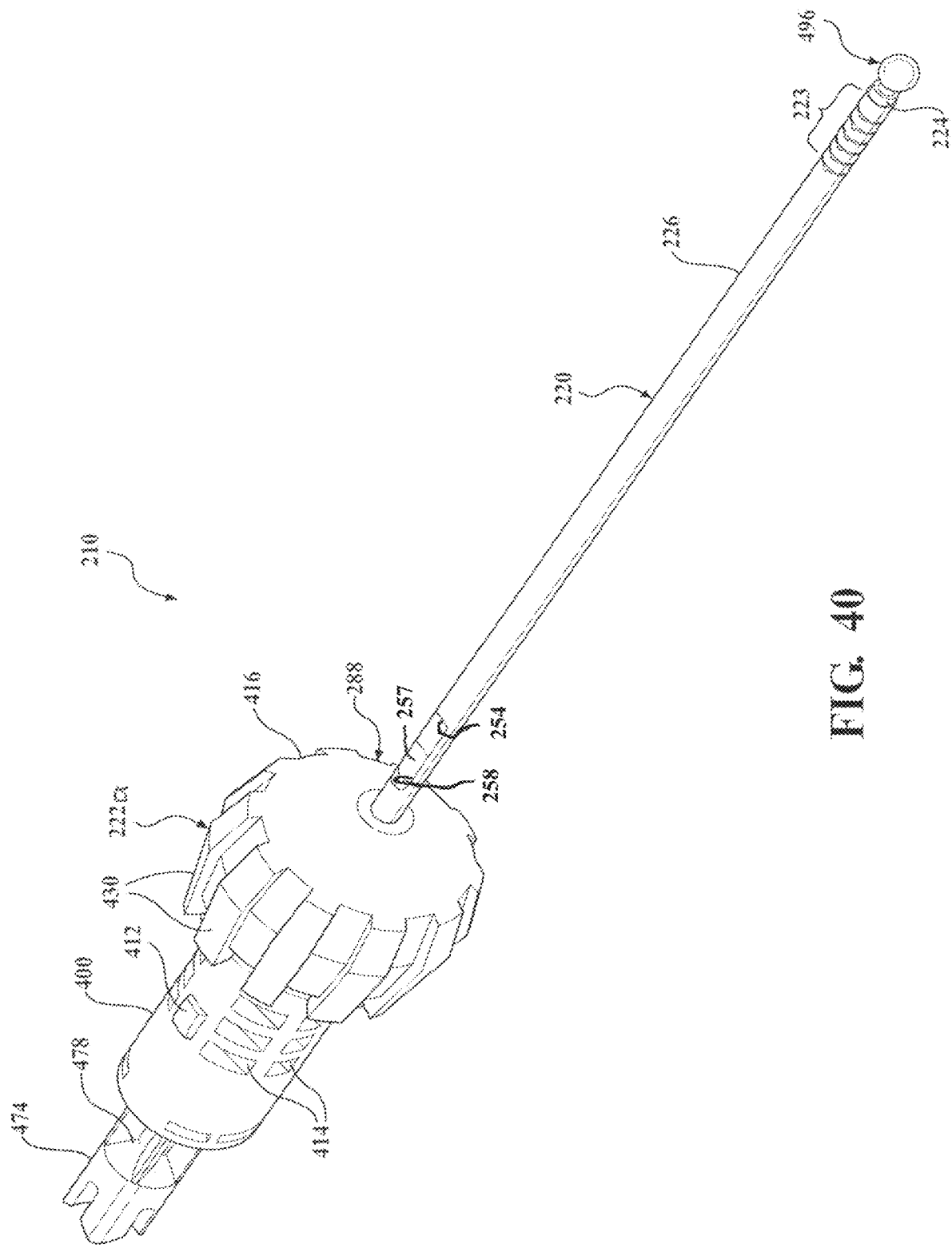
FIG. 40 is a perspective view of yet another embodiment, according to the present invention, of the surgical instrument.
Figure 41:
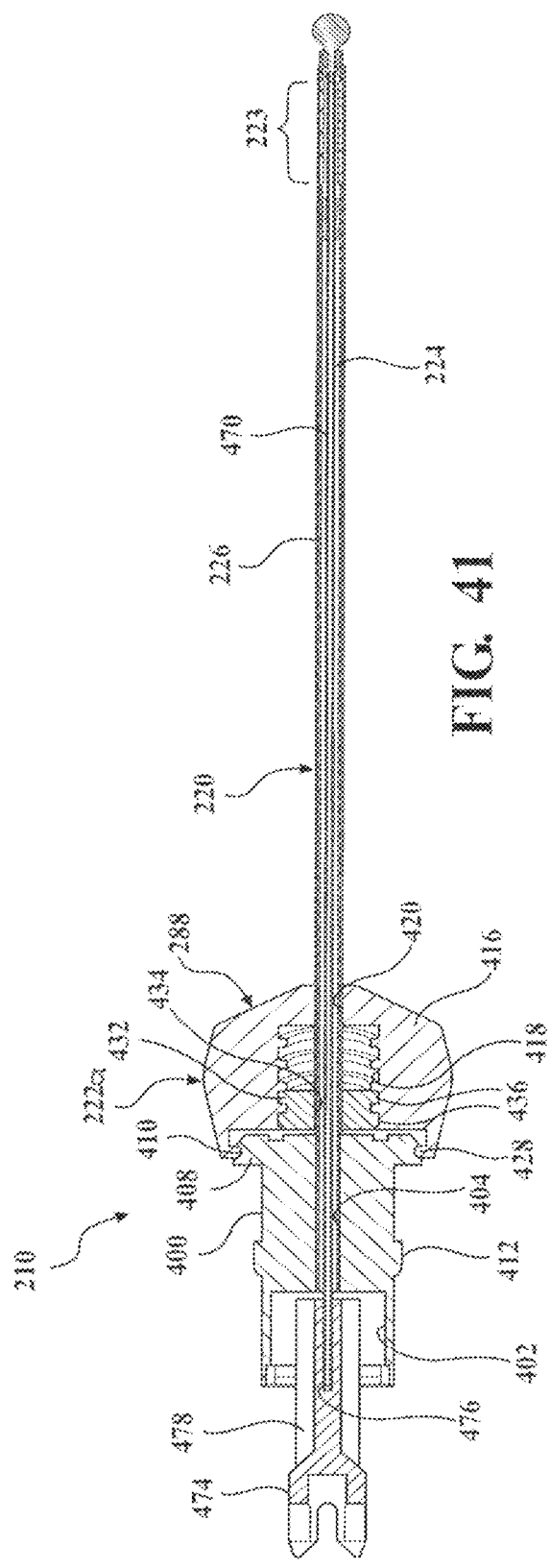
FIG. 41 is a cross-sectional view of the surgical instrument of FIG. 40.
Figure 42:
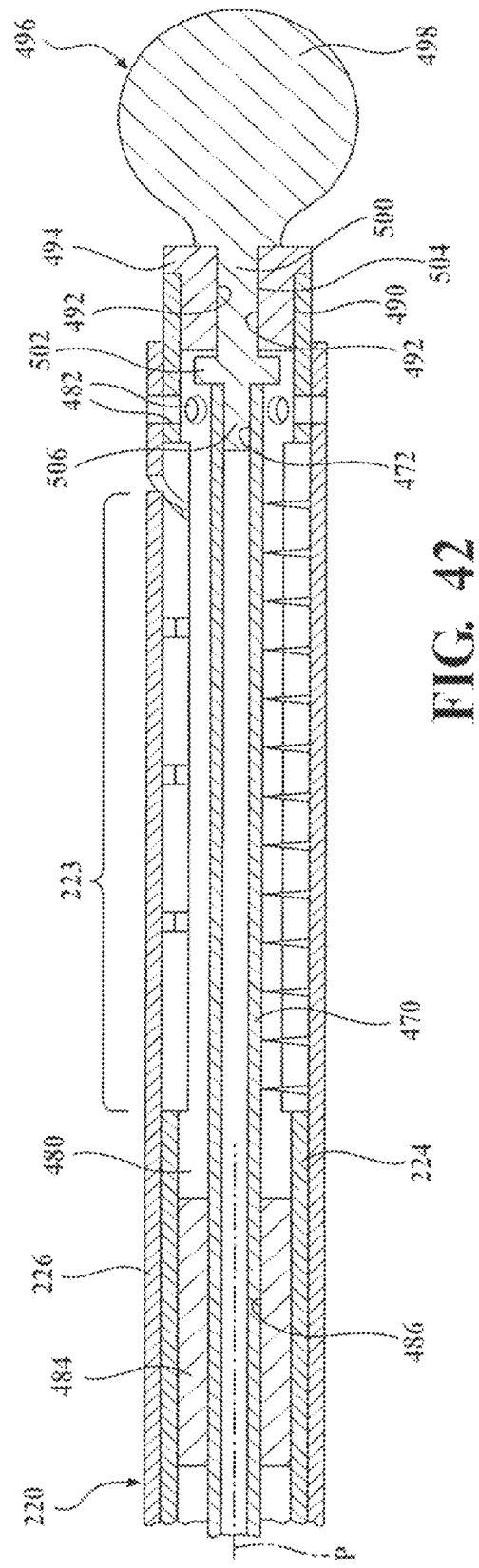
FIG. 42 is an enlarged view of a distal end of the surgical instrument of FIG. 41.
Figure 43:
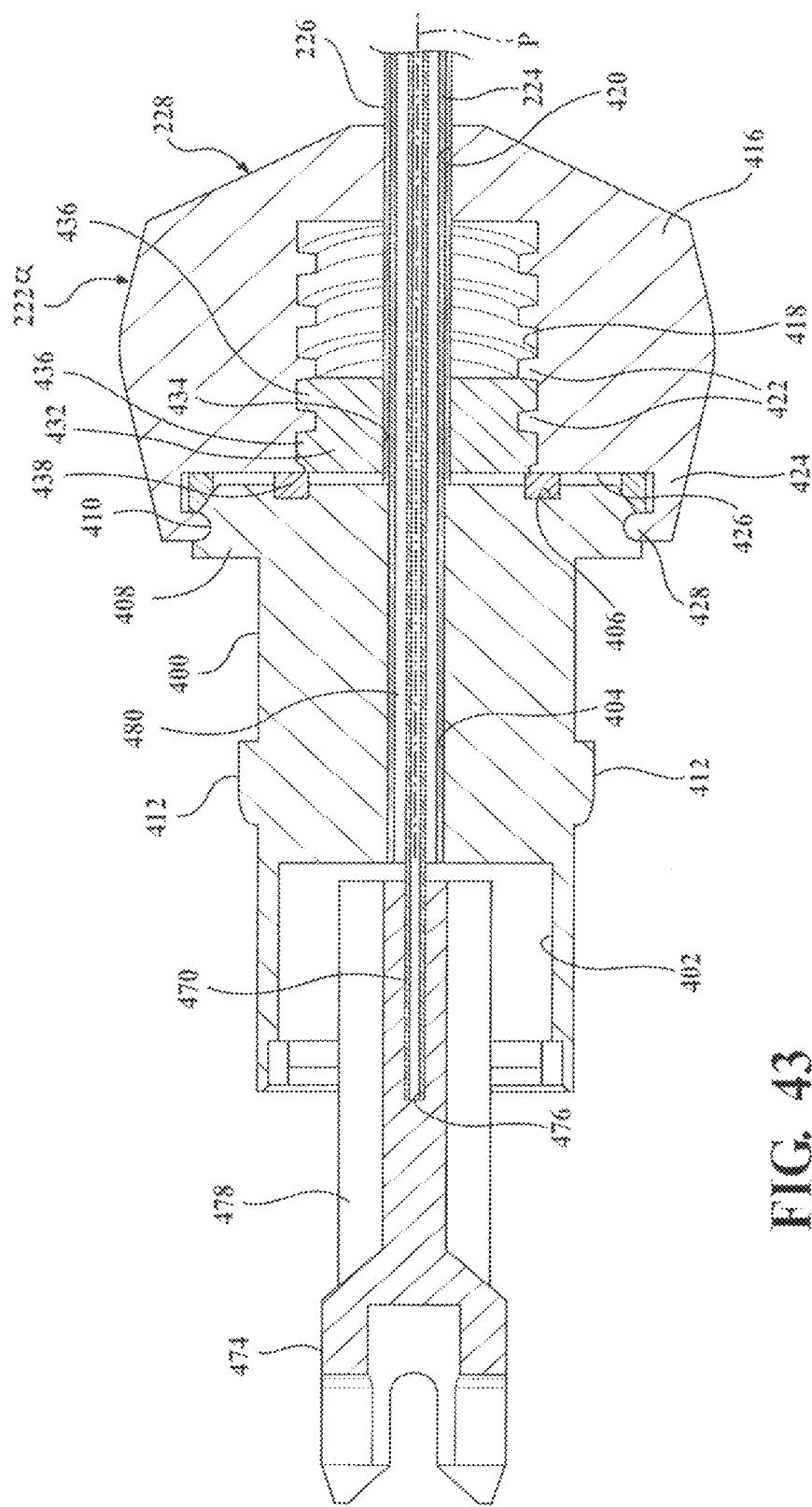
FIG. 43 is an enlarged view of a proximal end of the surgical instrument of FIG. 41.
Figure 44:
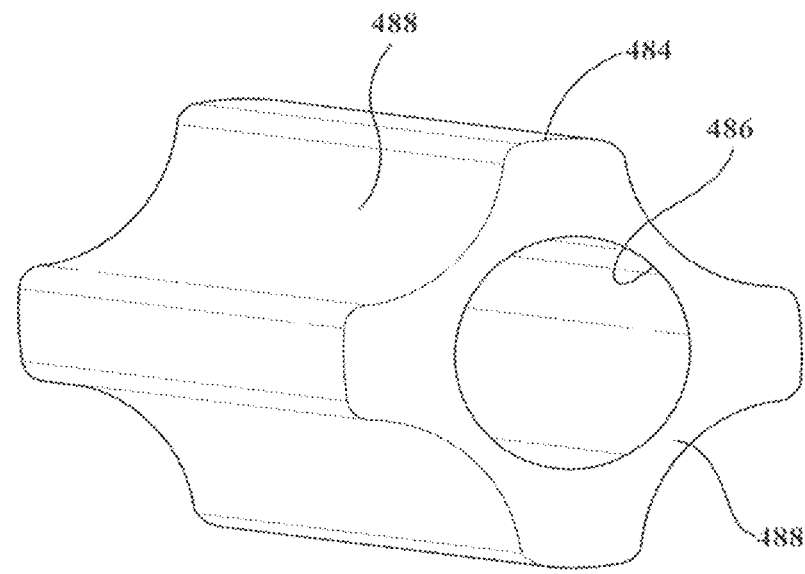
FIG. 44 is a perspective view of a proximal bearing of the surgical instrument of FIG. 41.
Figure 45:
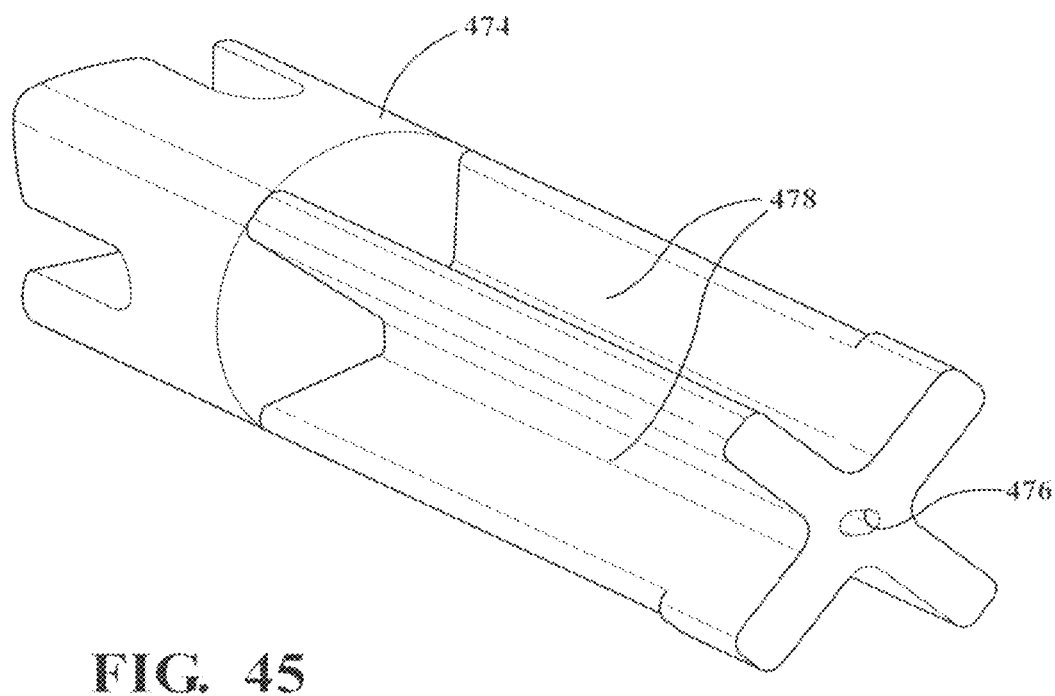
FIG. 45 is a perspective view of a driveshaft of the surgical instrument of FIG. 41.
Figure 46:
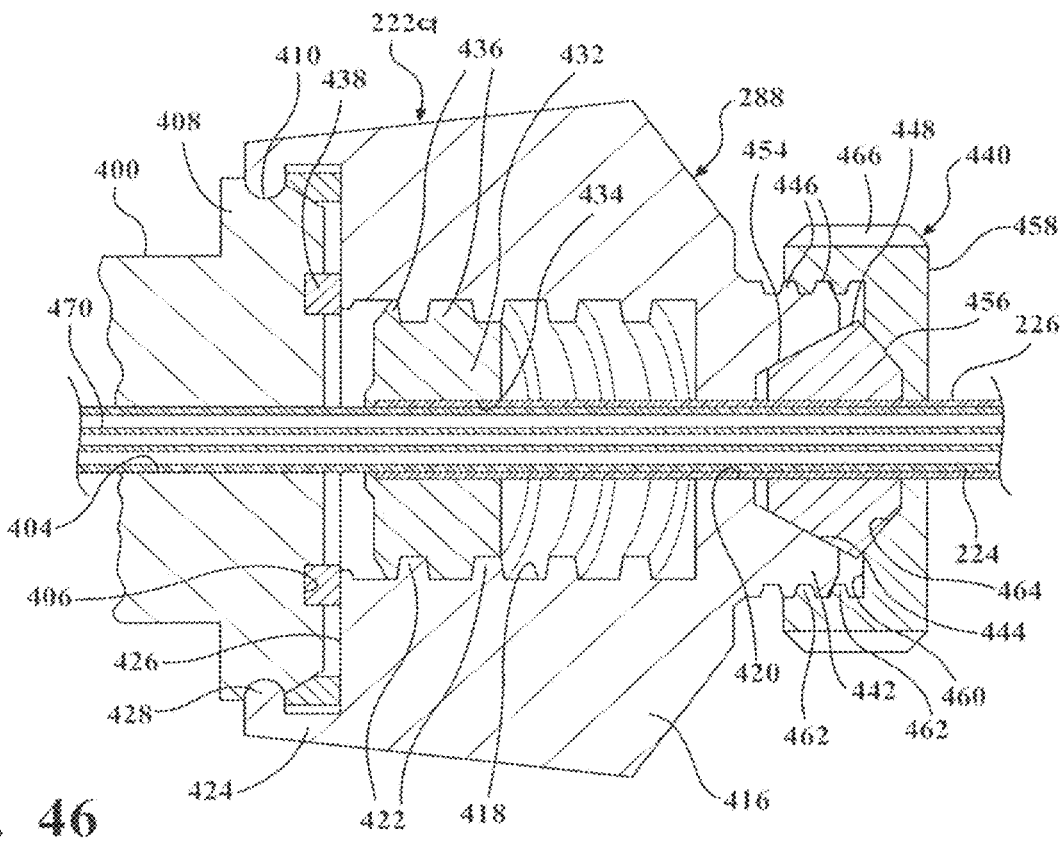
FIG. 46 is still another embodiment, according to the present invention, of the surgical instrument illustrating a locking assembly.
Figure 47:
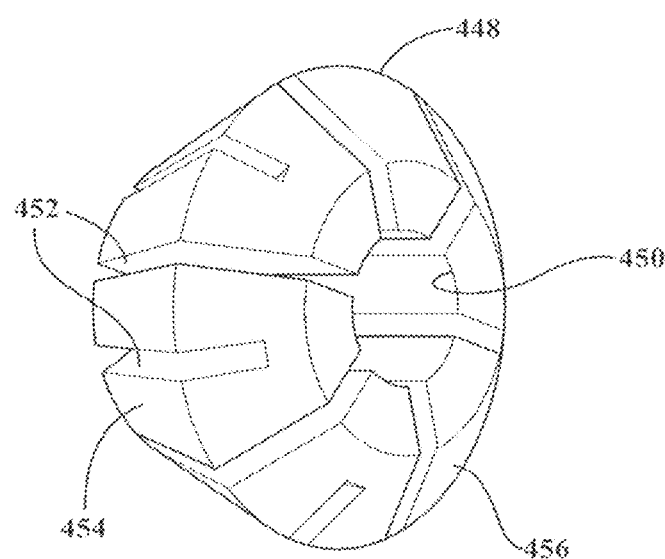
FIG. 47 is a perspective view of a floating collet of the locking assembly for the surgical instrument of FIG. 46.

Referring to FIG. 39, the surgical instrument 10, 110 allows the opening 14c of the outer tube 14b of the working tool 12g to be rotated with respect to the articulating tube assembly 20, 120. It should be appreciated that the flexible region 15 of the working tool 12g allows it to be rotated when the articulating region 23, 123 is bent or curved in only one direction.

One advantage of the present invention is that the surgical instrument 10, 110 has tube articulation to facilitate reduced incision size, improved access and visibility, while enhancing surgical outcome and quicker recovery. Another advantage of the present invention is that the surgical instrument 10, 110 includes a relatively simple, inexpensive, articulating tube assembly 20, 120 constructed of two laser cut tubes which are welded or bonded together at the distal end. Yet another advantage of the present invention is that the surgical instrument 10, 110 includes a relatively inexpensive articulating tube assembly 20, 120 that is capable of locking very rigidly in both straight and curved positions. Still another advantage of the present invention is that the surgical instrument 10, 110 includes tube articulation that provides rigidity in these positions sufficient to resist off axis loading such as that seen with power-tool cutting. A further advantage of the present invention is that the surgical instrument 10,110 includes tube articulation that allows for a large central opening to facilitate tissue extraction. Yet a further advantage of the present invention is that the surgical instrument 10, 110 includes an articulating tube assembly 20,120 that may provide a large central cannula that enables a variety of flexible devices to be inserted and so enables the articulating tube assembly 20, 120 to control their movement. Still a further advantage of the present invention is that the surgical instrument 10, 110 includes an articulating tube assembly 20, 120 capable of becoming rigid to resist off-axis loading. Yet still a further advantage of the present invention is that the surgical instrument 10, 110 includes an articulating tube assembly 20, 120 that has the ability to latch or bottom out in a straight position without snaking, and in a curved position, without snaking.

Referring to FIGS. 40 through 50, yet another embodiment, according to the present invention, of the surgical instrument 10 is shown. Like parts of the surgical instrument 10 have like reference numerals increased by one hundred (100). In one embodiment illustrated in FIGS. 40 through 45, the surgical instrument 210 includes the articulating tube assembly 220 having a proximal end and a distal end. The articulating tube assembly 220 includes the articulating region 223 disposed between the proximal end and the distal end and a proximal axis "P" axially extending from the proximal end to the articulating region 223. The articulating tube assembly 220 includes the inner tube 224 and the outer tube 226 each having the articulating region 223. The inner tube 224 and the outer tube 226 are movable relative to each other proximal to the articulating region 223 and fixed axially relative one another distal to the articulating region 223. It should be appreciated that the articulating tube assembly 220 is similar to the articulating tube assembly 20. It should also be appreciated that, in this embodiment of the surgical instrument 210, the articulating tube assembly 220 is a single integrated instrument that is devoid of a working channel for receiving the working tool 12.

The articulating region 223 is rigid in a first configuration and a second configuration relative to the proximal axis P to resist off-axial loading. In one embodiment, the first configuration may be a straight configuration relative to the proximal axis P and the second configuration may be a curved configuration relative to the proximal axis P. In another embodiment, the first configuration may be a curved configuration and the second configuration may be a curved configuration having a curvature greater than a curvature of the first configuration. FIG. 50 illustrates one example of a curved configuration. The curved configuration extends only in a single plane up to one hundred eighty degrees relative to the proximal axis P. In another embodiment, the curved configuration extends in only a single plane up to one hundred twenty degrees relative to the proximal axis P. In yet another embodiment, the curved configuration extends in only a single plane up to ninety degrees relative to the proximal axis P. The inner tube 224 and outer tube 226 form an outer lumen and the mechanical mechanism for articulation. The inner tube 224 and outer tube 226 are sized so that the tubes 224, 226 slide over one another with a close fit. For example, the outer tube (226) has an outer diameter of approximately two millimeters (2 mm) to approximately twelve millimeters (12 mm). In one embodiment, lasercuts are made in each tube 224, 226 and the tubes 224 and 226 are welded together at the distal end in a position so that the lasercut sections overlap. The sections cut away from the tubes 224 and 226 allow them to bend in one direction, but not the other. In one embodiment, the inner tube 224 extends axially past a distal end of the outer tube 226. When the tubes 224 and 226 are welded, and one tube 224, 226 is pushed or pulled axially relative to the other, the articulating region 223 of the articulating tube assembly 220 is caused to bend to a curved configuration. It should be appreciated that, at the extremes of motion (i.e., straight or fully bent), the tubes 224, 226 do not have mechanical backlash and thus are rigid. It should also be appreciated that, at the proximal end of the surgical instrument 210, there are components that enable the surgeon to control the articulation and allow the surgical instrument 210 to attach to and be driven by a drive assembly (not shown). It should be further appreciated that a lasercut pattern for the inner tube 224 extends beyond the proximal and distal limits of the lasercut pattern for the outer tube 226 to prevent the articulating tube assembly 220 from possible fatiguing.

The inner tube 224 is fixed to a hub 400 to be described. The outer tube 226 includes a slot aperture 254 extending through a wall thereof and disposed between the articulating region 223 and the proximal end. The slot aperture 254 extends axially and is elongated. The outer tube 226 includes a pad 257 disposed in the slot aperture 254 and a tab 261 extending axially between the outer tube 226 and the pad 257 to temporarily connect the pad 257 to the outer tube 226. The pad 257 is generally elongated axially. After the distal ends of the tubes 224 and 226 are fixed, the pad 257 of the outer tube 226 is welded to the inner tube 224. The tab 261 of the outer tube 226 is then removed. It should be appreciated that the pad 257 acts as an anti-rotation mechanism between the inner tube 224 and the outer tube 226.

The surgical instrument 210 also includes an actuation assembly 222a coupled to the articulating tube assembly 220 for moving the inner tube 224 and the outer tube 226 axially relative to each other for articulating the articulating region 223 of the articulating tube assembly 220 between a straight configuration and one or more curved configurations in only a single plane. The actuation assembly 222a includes a rotation assembly 288 disposed about the outer tube 226 to be rotated by a user. The rotation assembly 288 includes a tube receiving portion or hub 400 connected to the inner tube 224. The hub 400 is generally cylindrical and circular in shape, but may be any suitable shape. The hub 400 includes a cavity 402 extending axially inward from a proximal end thereof and an aperture 404 extending axially inward from a distal end thereof to receive the inner tube 224. The inner tube 224 is connected to the hub 400 by a suitable mechanism such as a friction fit, an adhesive, knurling, or thermally staking or thermally bonding to plastic. The hub 400 includes a groove 406 extending axially inward from the distal end of thereof. The groove 406 is generally circular in shape, but may be any suitable shape. The hub 400 includes a flange 408 extending radially from the distal end thereof and having an external groove 410 extending radially inward. The hub 400 may include one or more projections 412 extending axially and radially for coupling to a drive assembly (not shown). The hub 400 is made of a plastic material. The hub 400 is integral, unitary, and one-piece.

The rotation assembly 288 also includes a rotatable articulation control wheel 416 coupled to the outer tube 226 and being continuously adjustable to adjust a degree of curvature of the articulating region 223 of the articulating tube assembly 220 relative to the proximal axis P. The articulation control wheel 416 is generally cylindrical and circular in shape, but may be any suitable shape. In one embodiment illustrated in FIGS. 40-43, the articulation control wheel 416 includes a cavity 418 extending axially inward from a proximal end thereof and an aperture 420 extending axially inward from a distal end thereof into which the outer tube 226 extends. The cavity 418 includes one or more internal threads 422 extending axially and radially therealong. The articulation control wheel 416 includes a flange 424 extending axially from a proximal end thereof to form a recess 426 for receiving a portion of the hub 400. The flange 424 includes a radial projection 428 disposed in the external groove 410 to attach the articulation control wheel 416 to the hub 400 by a radial snap fit. The articulation control wheel 416 may include a plurality of external projections 430 extending radially and axially and spaced circumferentially thereabout to be gripped by a hand of the user. The articulation control wheel 416 is made of a plastic material. The articulation control wheel 416 is integral. It should be appreciated that the articulation control wheel 416 is rotatable by the hand of the user of the surgical instrument 210. It should also be appreciated that the only mechanical connection between the articulation control wheel 416 and the outer tube 226 is via the threads 422 of the articulation control wheel 416 interacting with threads of a lead screw 432 to be described that is bonded to the outer tube 226.

The rotation assembly 288 includes a gear mechanism or lead screw 432 connected to the outer tube 226 and disposed in the cavity 418 of the articulation control wheel 416. The lead screw 432 is generally cylindrical and circular in shape. The lead screw 432 has an aperture 434 extending axially therethrough to receive the outer tube 226. The lead screw 432 is bonded to the proximal end of the outer tube 226. The lead screw 432 has one or more external threads 436 extending radially and axially therealong to matingly engage the internal threads 422 in the cavity 418 of the articulation control wheel 416. The internal threads 422 of the cavity 418 and the external threads 436 of the lead screw 432 contain a matching thread pattern that drives the lead screw 432. The external threads 436 have a pitch of approximately 0.2 inches to approximately 0.6 inches to prevent unintentional translation of the lead screw 432 under load. It should be appreciated that the pitch used on the lead screw 432 ensures that the articulation control wheel 416 does not rotate under load and is dependent on the material and the size of the threads.

The rotation assembly 288 may further includes a wave spring 438 disposed between the hub 400 and the articulation control wheel 416 to keep the hub 400 under load between the straight and curved configurations. The wave spring 438 is generally circular in shape. The wave spring 438 is made of a spring material. The wave spring 438 may be disposed in the groove 406 of the hub 400. It should be appreciated that, by turning the articulation control wheel 416 clockwise and anti-clockwise, the outer tube 226 of the articulating tube assembly 220 is pushed/pulled proximal/distal, causing articulation of the articulating region 223.

In another embodiment illustrated in FIGS. 46 through 50, the articulation assembly 222a may include a locking assembly, generally indicated at 440, cooperating with the rotation assembly 288 to lock the rotation assembly 288 in one or more positions such that the articulating region 223 is locked in one or more curvature configurations and prohibits the articulation control wheel 416 from turning. In the embodiment illustrated, the locking assembly 440 includes a projection 442 extending axially from a distal end of the articulation control wheel 416 and having a cavity 444 extending axially inward. The cavity 444 has a generally frustoconical or tapered shape. The projection 442 includes one or more external threads 446 extending axially and radially and disposed circumferentially thereabout. The projection 442 is integral, unitary, and one-piece with the articulation control wheel 416. It should be appreciated that the cavity 444 communicates with the aperture 420 of the articulation control wheel 416.

The locking assembly 449 also includes a floating collet 448 partially disposed in the cavity 444 of the projection 442 on the articulation control wheel 416. The floating collet 448 is generally cylindrical and circular in shape, but may have any suitable shape. The floating collet 448 has a central aperture 450 extending axially therethrough to receive the articulating tube assembly 220. The floating collet 448 has a plurality of slits or slots 452 extending axially therealong and disposed circumferentially thereabout and spaced from the central aperture 450 to allow the central aperture 450 to be compressed about the outer tube 226 of the articulating tube assembly 220. The floating collet 448 includes a first frustoconical portion 454 at a proximal end thereof and a second frustoconical portion 456 at a distal end thereof. The cavity 444 of the projection 442 of the articulation control wheel 416 and the proximal end of the floating collet 448 have a tapered surface or shape to matingly engage each other. The floating collet 448 is made of a plastic material or a metal material. The floating collet 448 is integral, unitary, and one-piece. It should be appreciated that the locking assembly 440 engages with the outer tube 226 of the articulating tube assembly 220 and prevents the articulating tube assembly 220 from being actuated by the articulation control wheel 416 and lead screw 432. It should also be appreciated that the locking assembly 440 may be engaged when the user has achieved their desired level of articulation and desires to lock the curvature of the articulating region 223 of the articulating tube assembly 220 in place. It should further be appreciated that the locking assembly 440 may only be necessary when the user is applying high levels of force.

The locking assembly 440 further includes a rotatable locking wheel 458 cooperating with the floating collet 448 and the projection 442 on the articulation control wheel 416. The locking wheel 458 is generally cylindrical and circular in shape, but may have any suitable shape. The locking wheel 458 has a cavity 460 extending axially inward from a proximal end thereof and a plurality of internal threads 462 disposed in the cavity 460 and extending radially and axially therealong to mate with the external threads 446 on the projection 442 of the articulation control wheel 416. The locking wheel 458 also has a frustoconical recess 464 extending axially inward from the cavity 460 to receive the second frustoconical portion 456 of the floating collet 448. The frustoconical recess 464 of the locking wheel 458 and the second frustoconical portion 456 of the floating collet 448 have a tapered surface or shape to matingly engage each other to cause a friction lock on the outer tube 226 to prevent the outer tube 226 from moving axially. The locking wheel 458 may include a plurality of external projections 466 extending radially and axially and spaced circumferentially thereabout to be gripped by a hand of the user. The locking wheel 458 is made of a plastic material. The locking wheel 458 is integral, unitary, and one-piece. It should be appreciated that the floating collet 448 is shaped so that its internal diameter reduces as the locking wheel 458 is screwed down onto the projection 442 of the articulation control wheel 416. It should also be appreciated that this causes a friction lock on the outer tube 226 of the articulating tube assembly 220, thereby preventing the outer tube 226 from moving axially and causing unwanted bending or straightening of the articulating region 223 of the articulating tube assembly 220. It should further be appreciated that the locking assembly 440 is optional. It should still be further appreciated that other articulating mechanisms may be used to provide a similar function of preventing the outer tube 226 from moving axially and causing unwanted bending or straightening of the articulating region 223 of the articulating tube assembly 220.

Referring again to FIGS. 40 through 45, the surgical instrument 210 includes a torque member 470 disposed within the inner tube 224 and extending axially. The torque member 470 is generally cylindrical and circular in shape, but may be any suitable shape. The torque member 470 may be a hollow tube or a solid member. The torque member 470 may have a hollow distal end 472. The torque member 470 may have a variable stiffness with a first stiffness in the articulating region 223 and a second stiffness greater than the first stiffness outside the articulating region 223. The torque member 470 is made of a metal material. In one embodiment, the torque member 470 may be formed from wrapping wires helically into a tube shape known as a torque coil. The torque member 470 is integral. It should be appreciated that the rigidity of the torque member 470 in the straight section of the articulating tube assembly 220 reduces vibration during operation of a rotatable end effector 496 to be described. It should also be appreciated that the torque member 470 can transmit torque around the bent or curved articulating region 223 of the articulating tube assembly 220.

The surgical instrument 210 also includes a driveshaft 474 coupled to the torque member 470. The driveshaft 474 is generally cylindrical and circular in shape, but may have any suitable shape. The driveshaft 474 includes a cavity 476 extending axially inward from a distal end thereof for receiving a proximal end of the torque member 470. The torque member 470 is mechanically bonded to the driveshaft 474 by a suitable mechanism such as a friction fit, adhesive, or keyway system (proximal end of the torque member 470 is machined to have a specific shape and is received with a matching shape in the driveshaft 474). The driveshaft 474 also includes a plurality of external cutaways 478 spaced from the cavity 476 and extending axially partially therealong that are adapted to be coupled to a drive assembly (not shown). The driveshaft 474 may be made of a plastic material or a metal material. The driveshaft 474 is integral, unitary, and one-piece. It should be appreciated that torque member 470 passes through the hub 400 and the proximal end is disposed in the cavity 402 and bonded to the driveshaft 474, which interfaces with a drive mechanism of the drive assembly.

The surgical instrument 210 may include a suction path 480 formed between the inner tube 224 and the torque member 470. The suction path 480 extends axially and circumferentially between the inner tube 224 and the torque member 470. The suction path 480 includes at least one or more suction ports 482 extending through the inner tube 224 and the outer tube 226 and disposed axially between the articulating region 223 and a proximal end of a distal bearing to be described to allow removal of cutting debris and fluid therethrough and into the suction path 480. The suction ports 482 are spaced circumferentially about the distal end of the outer tube 226. The distal end of the suction path 480 fluidly communicates with the suction ports 482. The proximal end of the suction path 480 fluidly communicates with the cavity 402 of the hub 400. It should be appreciated that the suction ports 482 may be formed by lasercuts into the distal end of the articulating tube assembly 220 to allow removal of cutting debris and fluid from a joint undergoing arthroscopy.

The surgical instrument 210 also includes a proximal bearing 484 disposed in the suction path 480 proximal the articulating region 223 to support the torque member 470. The proximal bearing 484 is generally cylindrical and circular in shape, but may be any suitable shape. The proximal bearing 484 has a central aperture 486 extending axially therethrough to allow the torque member 470 to extend through the proximal bearing 484. The proximal bearing 484 includes a plurality of external cutaways 488 spaced from the central aperture 486 and extending axially therealong to allow fluid flow along the suction path 480 between the distal end and the proximal end of the suction path 480. The proximal bearing 484 may be made of a plastic, ceramic, metal, or other suitable bearing material. The proximal bearing 484 may be integral, unitary, and one-piece.

It should be appreciated that, in order to prevent a rotatable end effector 496 to be described from vibrating due to the whip of the torque member 470 during rotation, the proximal bearing 484 is fixed just proximal to the articulating region 223 of the articulating tube assembly 220. It should also be appreciated that the suction path 480 is in the lumen formed between the articulating tube assembly 220 and the torque member 470 and, for this reason, specific geometries are necessary on the proximal bearing 484 and the driveshaft 474 to allow unobstructed fluid flow therethrough to the drive assembly.

The surgical instrument 210 includes a distal bearing 490 disposed in the distal end of the inner tube 224 distal of the articulating region 223 to support an end effector to be described. The distal bearing 490 is generally cylindrical and circular in shape, but may have any suitable shape. The distal bearing 490 has a central aperture 492 extending axially therethrough. The distal bearing 490 has a flange 494 extending radially from a distal end thereof to abut the distal end of the inner tube 224. The distal bearing 490 has a clam shell configuration. The distal bearing 490 may be made of a ceramic, metal, or other suitable bearing material. The distal bearing 490 may be integral.

The surgical instrument further includes an end effector disposed distal of the articulating region 223 and coupled to the torque member 470. In one embodiment, the end effector is a rotatable end effector, generally indicated at 496, such as a bur. The rotatable end effector 496 includes a head 498 at a distal end thereof and a shaft 500 extending from the head 498 to a proximal end coupled to the torque member 470. The head 498 is generally spherical in shape, but may be any suitable shape. The head 498 may be fluted or coated with a diamond grit to enable cutting of bone. The shaft 500 is generally cylindrical and circular in shape, but may be any suitable shape. The shaft 500 extends through the central aperture 492 of the distal bearing 490. The rotatable end effector 496 includes a flange 502 extending radially from the shaft 500 and disposed axially between the head 498 and the proximal end of the shaft 500. The rotatable end effector 496 includes a groove 504 extending radially and axially between the flange 502 and the head 498. The distal bearing 490 is disposed in the groove 504 to prevent the rotatable end effector 496 from exiting the distal bearing 490. The rotatable end effector 496 includes a barb 506 at the proximal end of the shaft 500 to be disposed in the hollow distal end 472 of the torque member 470 and the flange 502 abuts the end of the torque member 470. The barb 506 is secured to the torque member 470 by a suitable mechanism such as welding. It should be appreciated that the head 498 is machined with the groove 504, allowing the rotatable end effector 496 to be held by the clamshell distal bearing 490 that fits into the distal end of the inner tube 224 of the articulating tube assembly 220. It should also be appreciated that the rotatable end effector 496 has the barb 506 machined at the proximal end, allowing the hollow distal end 472 of the torque member 470 to be welded onto the rotatable end effector 496. It should be further appreciated that other end effectors are contemplated other than rotatable end effectors such as any rotatable cutting element or tool.

Figure 51:
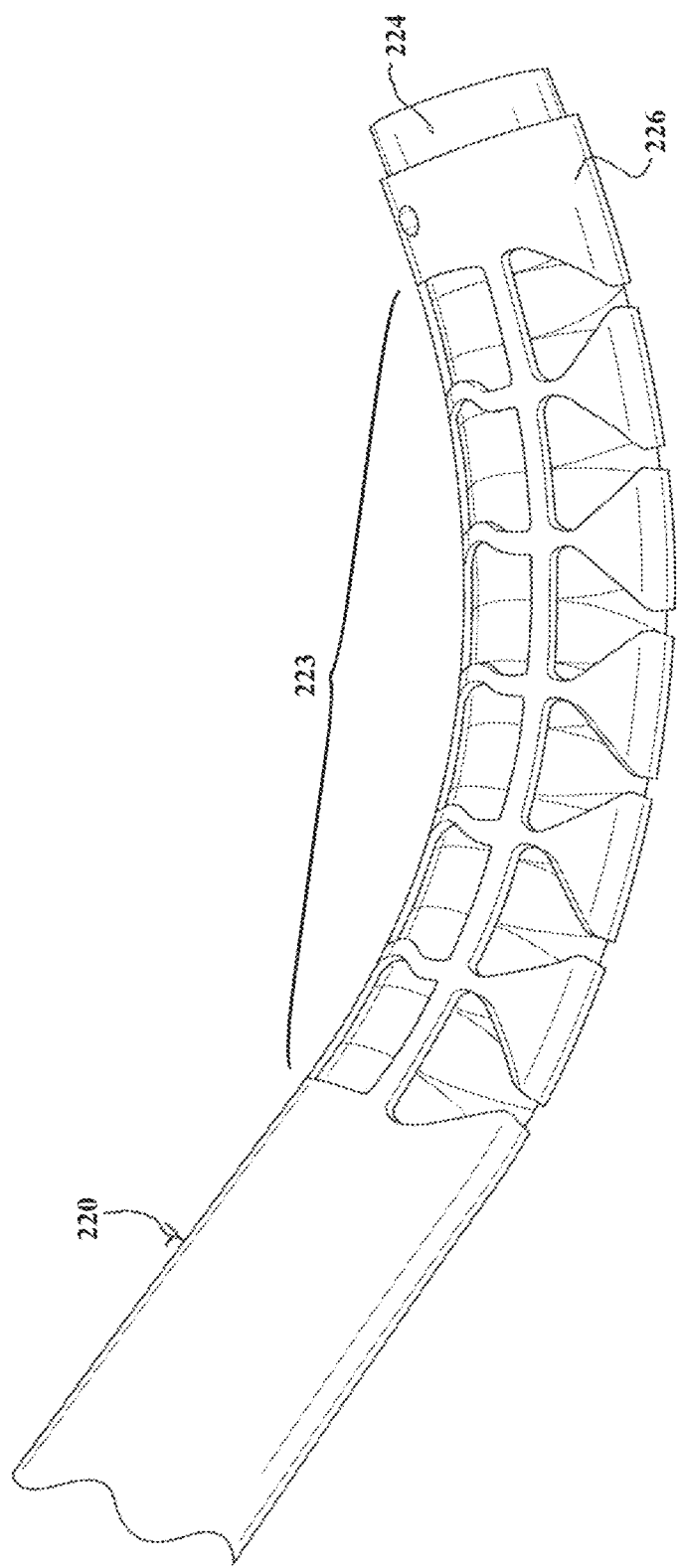
FIG. 51 is an enlarged view of an articulating section of the surgical instrument in a curved configuration.
Figure 52:
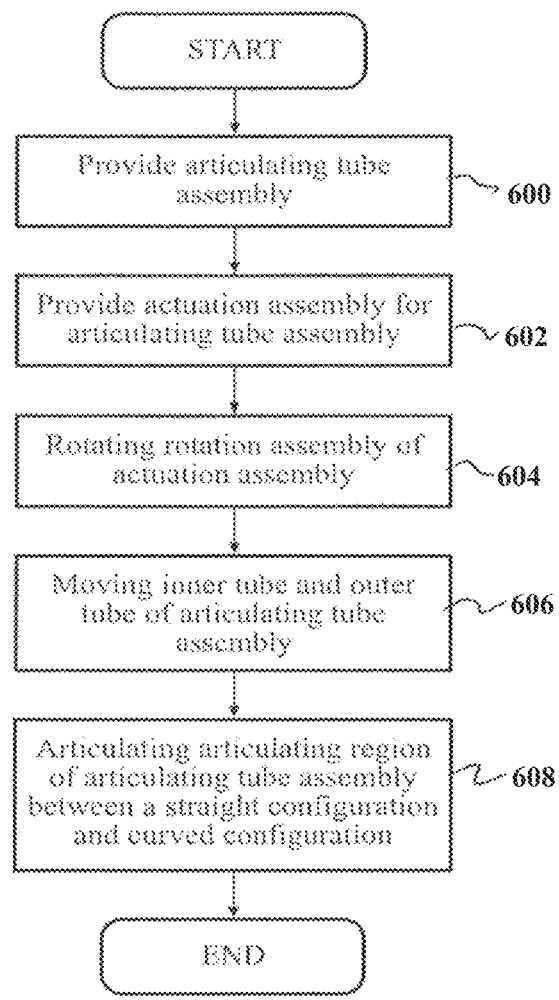
FIG. 52 is a flowchart of a method, according to the present invention, of operating a surgical instrument.

In addition, a method of operating a surgical instrument (10, 110, 210) is disclosed in FIG. 51. The method includes the steps of providing an articulating tube assembly (20, 120, 220) having a proximal end and a distal end, an articulating region (23, 123, 223) disposed between the proximal end and the distal end, and a proximal axis P axially extending from the proximal end to the articulating region (23, 123, 223), the articulating tube assembly (20, 120, 220) including an inner tube (24, 124, 224) and an outer tube (26, 126, 226) each having the articulating region (23, 123, 223), the inner tube (24, 124, 224) and the outer tube (26, 126, 226) being movable relative to each other proximal to the articulating region (23, 123, 223) and fixed axially relative one another distal to the articulating region (23, 123, 223) in block 600. The method also includes the steps of providing an actuation assembly (22, 122, 222a) coupled to the articulating tube assembly (20, 120, 220) in block 602.

The method is used typically for joint arthroscopy to examine and reshape/perform surgery on the inside structure of the joint. The method is commonly used on knee joints. The procedure is performed by inserting the distal end of the articulating tube assembly (20, 120, 220) into the joint through a small incision in a patient. During this procedure, a separate tool is provided for irrigation of the joint. In addition, the inside of the joint is visualized using a separate arthroscopic camera.

The method includes the steps of rotating the rotation assembly (288) of the actuation assembly (222*a*) with one hand of the user in block 604 and moving the inner tube (24, 124, 224) and the outer tube (26, 126, 226) axially relative to each other in block 606. The method includes the step of articulating the articulating region (23, 123, 223) of the articulating tube assembly (20, 120, 220) between a first configuration and a second configuration in only a single plane in block 608. The method includes the steps of rotating the rotation assembly (288) of the actuation assembly (222*a*) by a user to move the inner tube (224) and the outer tube (226) axially relative to each other. The method includes the steps of locking a locking assembly 440 cooperating with the rotation assembly (288) to lock the rotation assembly (288) in one or more positions such that the articulating region (223) is locked in one or more curvature configurations and does not straighten under load.

The method includes the steps of providing a working tool 12 separate from the surgical instrument (10, 110). The working tool 12 may provide irrigation fluid adjacent the distal end of the articulating tube assembly (20, 120) and/or may provide visualization of the joint such as an arthroscopic camera. The method further includes the steps of using the working tool 12 with another or other hand of the user.

Accordingly, the surgical instrument 10, 110, 210 of the present invention incorporates a ridged locking articulation described above that provides the ability to remove the impingement among other clinical needs, and a viewing assembly 240 described above places a tiny visualization imaging element 246 very near the tip of the working tool 12 to give the surgeon the vision required to perform the task. The surgical instrument 10, 110 of the present invention includes an articulation tube assembly 20 that is capable of locking in a rigid position that becomes useful when there are tools 12 capable of being controlled by the articulating tube assembly 20. It should be appreciated that, in another embodiment, the surgical instrument 10, 110 may be used with the working tools 12 or the articulating tube assembly 20, 120 is integrated as part of the working tool 12 and might serve as the shaft portion 14 of the working tool 12 to be a dedicated tool or instrument.

Further, the surgical instrument 210 of the present invention has the ability to articulate from straight to up to one hundred eighty degree bend and an articulating end effector that is rigid with no backlash at extremes of articulation (straight or fully bent), allowing a surgeon to place sufficient force on a head of the end effector to debride bone in a controlled manner. The surgical instrument 210 of the present invention has a locking assembly to provide robust lock at the desired bend position, giving the surgeon assurance that the articulating region 223 will not straighten under load at intermediate bend positions where there will be some mechanical backlash. A method of operating the surgical instrument 210 of the present invention provides positioning of the head immediately distal of the articulating portion while also having suction functionality, which is a necessity in arthroscopy where the joint spaces are very small. The method of operating the surgical instrument 210 of the present invention allows for controlling the articulation that can be actuated using one hand, which is necessary for arthroscopy where the surgeon's other hand is using the arthroscope.

Clause 1: A surgical instrument (10, 110, 210) comprising: an articulating tube assembly (20, 120, 220) having a proximal end and a distal end, an articulating region (23, 123, 223) disposed between the proximal end and the distal end, and a proximal axis axially extending from the proximal end to the articulating region (23, 123, 223), the articulating tube assembly (20, 120, 220) including an inner tube (24, 124, 224) and an outer tube (26, 126, 226) each having the articulating region (23, 123, 223), the inner tube (24, 124, 224) and the outer tube (26, 126, 226) being movable relative to each other proximal to the articulating region (23, 123, 223) and fixed axially relative one another distal to the articulating region (23, 123, 223); and an actuation assembly (22, 122, 222*a*) coupled to the articulating tube assembly (20, 120, 220) for moving the inner tube (24, 124, 224) and the outer tube (26, 126, 226) axially relative to each other for articulating the articulating region (23, 123, 223) of the articulating tube assembly (20, 120, 220) between a first configuration and a second configuration, wherein the articulating region (23, 123, 223) is rigid in the first configuration and the second configuration.

Clause 2: A surgical instrument (10, 110, 210) as set forth in claim 1 wherein the rigidity of the articulating region (23, 123, 223) in the first configuration and the second configuration relative to the proximal axis is defined as resisting off-axis loading and the second configuration has a different curvature from the first configuration relative to the proximal axis.

Clause 3: A surgical instrument (10, 110, 210) as set forth in claim 1 or 2 wherein the first configuration and the second configuration extends in only a single plane up to one hundred twenty degrees relative to the proximal axis.

Clause 4: A surgical instrument (10, 110, 210) as set forth in any one of claim 1-3 wherein the articulating tube assembly (20, 120, 220) includes a rotation assembly (88, 188, 288) disposed about the outer tube (26, 126, 226) to be rotated by a user.

Clause 5: A surgical instrument (10) as set forth in any one of claims 1-4 including a viewing assembly (240) coupled to the articulating tube assembly (20) for allowing an operator to view the distal end of the articulating tube assembly (20).

Clause 6: A surgical instrument (10) as set forth in claim 5 wherein the view assembly (240) includes a main tube (242) and an imaging device (246) coupled to the main tube (242) and being capable of being moved along and rotated about the proximal axis of the articulating tube assembly (20).

Clause 7: A surgical instrument (10) as set forth in any one of claims 1-5 including an illumination assembly (248) coupled to the articulating tube assembly (20) for providing illumination to the distal end of the articulating tube assembly (20).

Clause 8: A surgical instrument (10) as set forth in claim 7 wherein the illumination assembly (248) includes a main tube (242) and an illumination device (250) coupled to the main tube (242) and being capable of being moved along and rotated about the proximal axis of the articulating tube assembly (20).

Clause 9: A surgical instrument (10, 110) as set forth in any one of claim 1-5 wherein the articulating region (23, 123) includes one or more articulating segments (72, 172) in the outer tube (26, 126).

Clause 10: A surgical instrument (10, 110) as set forth in claim 9 wherein the one or more articulating segments (72, 172) each include a protrusion (78, 178) extending axially in one direction and a recess (80, 180) extending axially in an opposed direction, the protrusion (78, 178) of one segment (72, 172) being disposed in the recess (80, 180) of an adjacent segment (72, 172).

Clause 11: A surgical instrument (10, 110) as set forth in claim 9 or 10 wherein the outer tube (26, 126) includes a plurality of apertures (60, 160) spaced axially and forming a plurality of beams (62, 162) extending axially and a plurality of tie straps (668, 168) extending circumferentially to the beams (62, 162).

Clause 12: A surgical instrument (10, 110) as set forth in claim 11 wherein articulating region (23, 123) includes one or more articulating segments (44, 144) in the inner tube (24, 124).

Clause 13: A surgical instrument (10, 110) as set forth in claim 12 wherein the inner tube (24, 124) includes a plurality of apertures (42, 142) spaced axially and forming a plurality of beams (34, 134) extending axially and a plurality of tie straps (40, 140) extending circumferentially to the beams (42, 142).

Clause 14: A surgical instrument (10, 110) as set forth in claim 13 wherein the beams (34, 134) of the inner tube (24, 124) and the beams (62,162) of the outer tube (26, 126) are approximately 180 degrees opposed from one another.

Clause 15: A surgical instrument (10, 110) as set forth in any one of claim 12 or 13 wherein the outer tube (26, 126) includes a plurality of faces configured to seat and secure the articulating region (23, 123) in a straight configuration.

Clause 16: A surgical instrument (10, 110) as set forth in any one of claims 1-5 wherein the actuation assembly (22, 122) includes a tube receiving portion (150, 250) to receive the articulating tube assembly (20, 120).

Clause 17: A surgical instrument (10) as set forth in claim 16 wherein the actuation assembly (22) includes at least one trigger (146, 148) for articulating the articulating tube assembly (20).

Clause 18: A surgical instrument (110) as set forth in claim 16 wherein the actuation assembly (122) includes at least one lever (380) for articulating the articulating tube assembly (120).

Clause 19: A surgical instrument (10) as set forth in claim 4 wherein the rotation assembly (88) includes a rotatable member to allow the user to rotate the articulating tube assembly (20).

Clause 20: A surgical instrument (10, 110) as set forth in any one of claims 1-5 wherein the articulating tube assembly (20, 120) is hollow to form a working channel adapted to receive a surgical tool (12).

Clause 21: A surgical instrument (10, 110) as set forth in any one of claim 1-5 wherein the articulating tube assembly (20, 120) is a single integrated instrument devoid of a passage adapted to receive fluid flow for irrigation.

Clause 22: A surgical instrument (210) as set forth in claim 4 wherein the rotation assembly (288) comprises a rotatable articulation control wheel (416) coupled to the outer tube (226) and being continuously adjustable to adjust a degree of curvature of the articulating region (223) relative to the proximal axis.

Clause 23: A surgical instrument (210) as set forth in claim 22 wherein the articulation control wheel (416) includes a first cavity (444) extending axially inward from a distal end thereof and a second cavity (418) extending inward from a proximal end thereof.

Clause 24: A surgical instrument (210) as set forth in claim 23 wherein the second cavity (418) includes one or more internal threads (422).

Clause 25: A surgical instrument (210) as set forth in claim 24 including a lead screw (432) connected to the outer tube (226) and having one or more external threads (436) disposed in the second cavity (418) of the articulation control wheel (416) to matingly engage the internal threads (422).

Clause 26: A surgical instrument (210) as set forth in claim 25 wherein the external threads (436) have a pitch of approximately 0.2 inches to approximately 0.6 inches to prevent translation of the lead screw (432) under load.

Clause 27: A surgical instrument (210) as set forth in claim 25 or 26 including a hub (400) connected to the inner tube (224) and having an external groove (410) at a distal end thereof.

Clause 28: A surgical instrument (210) as set forth in claim 27 wherein the articulation control wheel (416) includes a radial projection (428) disposed in the external groove (410) to attach the articulation control wheel (416) to the hub (400) by a radial snap fit.

Clause 29: A surgical instrument (210) as set forth in claim 27 or 28 including a wave spring (438) disposed between the hub (400) and the articulation control wheel (416) to keep the lead screw (432) under load and to prevent translation of the lead screw (432) during use.

Clause 30: A surgical instrument (210) as set forth in any one of claims 23-29 including a locking assembly (440) cooperating with the rotation assembly (288) to lock the rotation assembly (288) in one or more positions such that the articulating region (223) is locked in one or more curvature configurations and prohibits rotation of the rotation assembly (288).

Clause 31: A surgical instrument (210) as set forth in claim 30 wherein the locking assembly (440) includes a floating collet (448) disposed in the first cavity (444) of the articulation control wheel (416) and having a central aperture (450) to allow the articulating tube assembly (220) to extend axially therethrough.

Clause 32: A surgical instrument (210) as set forth in claim 31 wherein the floating collet (448) has a plurality of slits (452) disposed circumferentially thereabout and spaced from the central aperture (450) to allow the central aperture (450) to be compressed about the outer tube (226).

Clause 33: A surgical instrument (210) as set forth in claim 32 wherein the first cavity (444) of the articulation control wheel (416) and a proximal end of the floating collet (448) having a tapered shape to matingly engage each other.

Clause 34: A surgical instrument (210) as set forth in claim 33 wherein the articulation control wheel (416) includes one or more external threads (446) at a distal end thereof.

Clause 35: A surgical instrument (210) as set forth in claim 34 wherein the locking assembly (440) includes a locking wheel (458) having a cavity (460) extending axially inward from a proximal end thereof and a plurality of internal threads (462) disposed in the cavity (460) to mate with the external threads (446) of the articulation control wheel (416).

Clause 36: A surgical instrument (210) as set forth in claim 35 wherein the locking wheel (458) and a distal end of the floating collet (448) have a tapered shape to matingly engage each other to cause a friction lock on the outer tube (226) to prevent the outer tube (226) from moving axially.

Clause 37: A surgical instrument (210) as set forth in any one of claims 22-36 including a torque member (470) disposed within the inner tube (224) and extending axially.

Clause 38: A surgical instrument (210) as set forth in claim 37 wherein the torque member (470) has a variable stiffness with a first stiffness in the articulating region (223) and a second stiffness greater than the first stiffness outside the articulating region (223).

Clause 39: A surgical instrument (210) as set forth in claim 37 or 38 including a suction path (480) formed between the inner tube (224) and the torque member (470).

Clause 40: A surgical instrument (210) as set forth in claim 39 including a proximal bearing (484) disposed in the suction path (480) proximal the articulating region (223) and having a central aperture (486) extending therethrough to allow the torque member (470) to extend through the proximal bearing (484).

Clause 41: A surgical instrument (210) as set forth in claim 40 wherein the proximal bearing (484) includes a plurality of external cutaways (488) spaced from the central aperture (484) and extending axially therethrough to allow fluid flow along the suction path (480) between the proximal end to the distal end.

Clause 42: A surgical instrument (210) as set forth in claim 40 or 41 including a distal bearing (490) disposed in the distal end of the inner tube (224) distal of the articulating region (223) and having a central aperture (492) extending axially therethrough.

Clause 43: A surgical instrument (210) as set forth in claim 42 including at least one suction port (482) extending through the inner tube (224) and the outer tube (226) and disposed between the articulating region (223) and a proximal end of the distal bearing (490) to allow removal of cutting debris and fluid therethrough and into the suction path (480).

Clause 44: A surgical instrument (210) as set forth in claim 42 or 43 including a rotatable end effector (496) disposed distal of the articulating region (223) and coupled to the torque member (470).

Clause 45: A surgical instrument (210) as set forth in claim 44 wherein the rotatable end effector (496) includes a head (498) at a distal end thereof and a shaft (500) extending from the head (498) through the central aperture (492) of the distal bearing (490) to a proximal end coupled to the torque member (470).

Clause 46: A surgical instrument (210) as set forth in claim 45 wherein the rotatable end effector (496) includes a flange (502) extending radially from the shaft (500) and disposed axially between the head (498) and the proximal end of the shaft (500) and a groove (504) extending radially into the shaft (500) axially between the flange (502) and the head (498).

Clause 47: A surgical instrument (210) as set forth in claim 46 wherein the distal bearing (490) has a clam shell configuration disposed in the groove (504) to prevent the rotatable end effector (496) from exiting the distal bearing (490).

Clause 48: A surgical instrument (210) as set forth in claim 46 or 47 wherein the torque member (470) has a hollow distal end (472) and the rotatable end effector (496) includes a barb (506) at the proximal end of the shaft (500) to be disposed in the hollow distal end (472) of the torque member (470).

Clause 49: A surgical instrument (210) as set forth in any one of claim 37-48 including a driveshaft (474) coupled to the torque member (470).

Clause 50: A surgical instrument (210) as set forth in claim 49 wherein the driveshaft (474) includes a cavity (476) for receiving a proximal end of the torque member (470) and a plurality of external cutaways (478) spaced from the cavity (476) and extending axially therethrough adapted to be coupled to a drive assembly.

Clause 51: A surgical instrument (210) as set forth in any one of claims 22-50 wherein the outer tube (226) has an outer diameter of approximately two millimeters (2 mm) to approximately twelve millimeters (12 mm).

Clause 52: A surgical instrument (210) as set forth in any one of claims 22-51 wherein the articulating tube assembly (220) is a single integrated instrument devoid of a working channel for receiving a surgical tool (12).

Clause 53: A surgical instrument (10, 110) comprising: an articulating tube assembly (20, 120) having a proximal end and a distal end, an articulating region (23, 123) disposed between the proximal end and the distal end, and a proximal axis axially extending from the proximal end to the articulating region (23, 123), the articulating tube assembly (20, 120) including an inner tube (24, 124) and an outer tube (26, 126) each having the articulating region (23, 123), the inner tube (24, 124) and the outer tube (26, 126) being movable relative to each other proximal to the articulating region (23, 123) and fixed axially relative one another distal to the articulating region (23, 123); an actuation assembly (22, 122) coupled to the articulating tube assembly (20, 120) for moving the inner tube (24, 124) and the outer tube (26, 126) axially relative to each other for articulating the articulating region (23, 123) of the articulating tube assembly (20, 120) between a first configuration and a second configuration in only a single plane; a viewing assembly (240) coupled to the articulating tube assembly (20, 120) for allowing an operator to view the distal end of the articulating tube assembly (20, 120); an illumination assembly (248) coupled to the articulating tube assembly (20, 120) for providing illumination to the distal end of the articulating tube assembly (20, 120).

Clause 54: A surgical instrument (210) comprising: an articulating tube assembly (220) having a proximal end and a distal end, an articulating region (223) disposed between the proximal end and the distal end, and a proximal axis axially extending from the proximal end to the articulating region (223), the articulating tube assembly (220) including an inner tube (224) and an outer tube (226) each having the articulating region (223), the inner tube (224) and the outer tube (226) being movable relative to each other proximal to the articulating region (223) and fixed axially relative one another distal to the articulating region (223); an actuation assembly (222a) coupled to the articulating tube assembly (220) for moving the inner tube (224) and the outer tube (226) axially relative to each other for articulating the articulating region (223) of the articulating tube assembly (220) between a first configuration and a second configuration; a torque member (470) disposed within the inner tube (224); a rotatable end effector (496) disposed distal of the articulating region (223) coupled to the torque member (470); and a driveshaft (474) coupled to the torque member (470) and adapted to be coupled to a drive assembly to drive the torque member (470) and the rotatable end effector (496).

Clause 55: A surgical instrument (210) as set forth in claim 54 wherein the actuation assembly (222a) comprises a rotation assembly (288) disposed about the outer tube (226) to be rotated by a user to move the inner tube (224) and the outer tube (226) axially relative to each other.

Clause 56: A surgical instrument (210) as set forth in claim 55 including a locking assembly (440) cooperating with the rotation assembly (288) to lock the rotation assembly (288) in one or more positions such that the articulating region (223) is locked in one or more curvature configurations and prohibits rotation of the rotation assembly (288).

Clause 57: A surgical instrument (210) as set forth in any one of claims 54-56 wherein the articulating region (223) is rigid in a straight configuration and in a curved configuration in only one a single plane up to one hundred eighty degrees relative to the proximal axis.

Clause 58: A surgical instrument (210) as set forth in any one of claims 54-57 including a suction path (480) formed between the inner tube (224) and the torque member (470).

Clause 59: A surgical instrument (210) as set forth in claim 58 including a proximal bearing (484) disposed in the suction path (480) proximal the articulating region (223) and having a central aperture (486) extending axially therethrough to allow the torque member (470) to extend through the proximal bearing (484).

Clause 60: A surgical instrument (210) as set forth in claim 59 wherein the proximal bearing (484) includes a plurality of external cutaways (488) spaced from the central aperture (486) and extending axially therethrough to allow fluid flow along the suction path (480) between the proximal end to the distal end.

Clause 61: A surgical instrument (210) as set forth in claim 59 or 60 including a distal bearing (490) disposed in the distal end of the outer tube (226) distal of the articulating region (223) and having a central aperture (492) extending axially therethrough.

Clause 62: A surgical instrument (210) as set forth in claim 61 including at least one suction port (482) extending through the inner tube (224) and the outer tube (226) and disposed between the articulating region (223) and a proximal end of the distal bearing (490) to allow removal of cutting debris and fluid therethrough and into the suction path (480).

Clause 63: A surgical instrument (210) as set forth in claim 61 or 62 wherein the end effector (496) includes a head (498) at a distal end thereof, a shaft extending from the head, a flange (502) extending radially from the shaft (500) and disposed axially between the head (498) and the proximal end of the shaft (500), and a groove (504) extending radially into the shaft (500) axially between the flange (502) and the head (498).

Clause 64: A surgical instrument (210) as set forth in claim 63 wherein the distal bearing (490) has a clam shell configuration disposed in the groove (504) to prevent the end effector (496) from exiting the distal bearing (490).

Clause 65: A surgical instrument (210) as set forth in claim 63 or 64 wherein the torque member (470) has a hollow distal end (472) and the rotatable end effector (496) includes a barb (506) at the proximal end of the shaft (500) to be disposed in the hollow distal end (472) of the torque member (470).

Clause 66: A method of operating a surgical instrument (10, 110, 210), the method comprising the steps of: providing an articulating tube assembly (20, 120, 220) having a proximal end and a distal end, an articulating region (23, 123, 223) disposed between the proximal end and the distal end, and a proximal axis axially extending from the proximal end to the articulating region (23, 123, 223), the articulating tube assembly (20, 120, 220) including an inner tube (24, 124, 224) and an outer tube (26, 126, 226) each having the articulating region (23, 123, 223), the inner tube (24, 124, 224) and the outer tube (26, 126, 226) being movable relative to each other proximal to the articulating region (23, 123, 223) and fixed axially relative one another distal to the articulating region (23, 123, 223); providing an actuation assembly (22, 122, 222a) coupled to the articulating tube assembly (20, 120, 220); and rotating a rotation assembly (288) of the actuation assembly (222a) with one hand of a user and moving the inner tube (24, 124, 224) and the outer tube (26, 126, 226) axially relative to each other for articulating the articulating region (23, 123, 223) of the articulating tube assembly (20, 120, 220) between a first configuration and a second configuration in only a single plane.

Clause 67: A method as set forth in claim 66 including the step of locking a locking assembly (440) cooperating with the rotation assembly (288) to lock the rotation assembly (288) in one or more positions such that the articulating region (223) is locked in one or more curvature configurations.

Clause 68: A method as set forth in claim 66 or 67 including the step of rotating a rotatable end effector (496) extending out a distal end of the inner tube (224).

Clause 69: A method as set forth in any one of claims 66-68 including the step of providing a tool (12) separate from the surgical instrument (10, 110) for providing irrigation fluid adjacent the distal end of the articulating tube assembly (20, 120).

Clause 70: A method as set forth in any one of claims 66-69 including the step of using the tool (12) with another hand of the user.

The present invention has been described in an illustrative manner. It is to be understood that the terminology, which has been used, is intended to be in the nature of words of description rather than of limitation. Many modifications and variations of the present invention are possible in light of the above teachings. Therefore, the present invention may be practiced other than as specifically described.

What is claimed is:

1. A surgical instrument comprising:
a handle;
an articulating tube assembly comprising an outer tube coupled to said handle, and an inner tube coaxially disposed within said outer tube, wherein each of said outer tube and said inner tube comprises an articulating region, wherein said outer tube and said inner tube are axially fixed to one another distal to said articulating regions and axially movable relative to one another proximal to said articulating regions;
an actuation assembly coupled to said outer tube or said inner tube, wherein said actuation assembly is configured to receive input of a user to force said outer tube or said inner tube to move relative to the other, wherein axial fixation of said outer tube and said inner tube distal to said articulating regions is configured to provide for articulation of said articulating tube assembly to a curved configuration; and
a working tool comprising a shaft configured to rotate within said inner tube, and an end effector coupled to said shaft, wherein said shaft comprises a flexible region arranged within said articulating regions such that said end effector is configured to be rotated with said articulating tube assembly in said curved configuration.

2. The surgical instrument of claim 1, wherein said inner tube defines central cannula, wherein said end effector of said working tool is configured to be removably directed through said central cannula.

3. The surgical instrument of claim 1, wherein said actuation assembly is configured to force said outer tube or said inner tube to move relative to the other in one of a first direction in which said articulating region of said inner tube provides rigidity to articulating tube assembly in said curved configuration, and a second direction in which said articulating region of said outer tube provides rigidity to said articulating tube assembly in a straight configuration.

4. The surgical instrument of claim 3, wherein each of said articulating regions comprise segments each including beams, tie straps extending circumferentially to said beams, and bottoming segments with adjacent bottoming segments defining a gap configured to close with said articulating tube assembly in one of said curved configuration and said straight configuration.

5. The surgical instrument of claim 1, wherein said shaft is a tool inner tube, said working tool further comprising a tool outer tube within which said tool inner tube is rotatably disposed, wherein each of said tool inner tube and said tool outer tube comprises a cutting window that cooperate to define said end effector.

6. The surgical instrument of claim 1, wherein said shaft is a torque coil configured to transmit torque along a curve with said articulating tube assembly in said curved configuration, said surgical instrument further comprising a proximal bearing supporting said torque coil, and a distal bearing supporting said end effector.

7. The surgical instrument of claim 6, wherein said proximal bearing defines a central aperture through which said torque coil extends, wherein said proximal bearing is positioned adjacent a proximal end of said articulating region so as to prevent whipping of said torque coil during high-speed rotation.

8. The surgical instrument of claim 6, wherein said proximal bearing comprises external cutaways configured to permit passage of fluid in a suction path between said proximal bearing and an inner surface of said inner tube.

9. A surgical instrument comprising:
a handle;
an articulating tube assembly comprising an outer tube coupled to said handle, and an inner tube coaxially disposed within said outer tube, wherein each of said outer tube and said inner tube comprises an articulating region;
an actuation assembly coupled to said outer tube or said inner tube, wherein said actuation assembly is configured to receive input of a user to force movement of said outer tube or said inner tube relative to the other, wherein axial fixation of said outer tube and said inner tube distal to said articulating regions is configured to provide for articulation of said articulating tube assembly to a curved configuration; and
a working tool comprising a flange portion and an insertion portion, a shaft coupled to said insertion portion and comprising a flexible region, and an end effector coupled to said shaft, wherein said flange portion and said insertion portion is configured to be removably coupled to said handle to removably position said flexible region of said working tool within said articulating regions of said articulating tube assembly.

10. The surgical instrument of claim 9, wherein said inner tube defines central cannula, wherein said end effector of said working tool is configured to be removably directed through said central cannula.

11. The surgical instrument of claim 9, wherein said handle and said flange portion comprise complimentary coupling features to releasably secure said working tool to said articulating tube assembly.

12. The surgical instrument of claim 9, wherein each of said articulating regions comprise segments each including beams, tie straps extending circumferentially to said beams, and bottoming segments with adjacent bottoming segments defining a gap configured to close and provide rigidity to said articulating tube assembly.

13. The surgical instrument of claim 9, wherein said working tool comprises a connecting portion coupled to said shaft and configured to be coupled to a power source for rotating said shaft within said inner tube.

14. The surgical instrument of claim 9, wherein said shaft is a torque coil configured to transmit torque along a curve with said articulating tube assembly in said curved configuration, wherein said end effector is a bur head fixedly secured to said torque coil.

15. A surgical instrument comprising:
a handle;
an articulating tube assembly comprising, an outer tube coupled to said handle, and an inner tube coaxially disposed within said outer tube and defining a central cannula, wherein each of said outer tube and said inner tube comprises an articulating region, wherein said outer tube and said inner tube are axially fixed to one another distal to said articulating regions and axially movable relative to one another proximal to said articulating regions;
an actuation assembly coupled to said outer tube or said inner tube, wherein said actuation assembly is configured to receive input of a user to force movement of said outer tube or said inner tube relative to the other, wherein axial fixation of said outer tube and said inner tube distal to said articulating regions is configured to provide for articulation of said articulating tube assembly to a curved configuration; and
a working tool comprising an end effector configured to removably directed through said central cannula of said inner tube, and a shaft coupled to said end effector and comprising a flexible region configured to be arranged within said articulating regions.

16. The surgical instrument of claim 15, wherein said working tool is a first working tool, said surgical instrument further comprising a second working tool having an another end effector configured to be removably directed through said central cannula such that said first and second working tools are interchangeable with said articulating tube assembly.

17. The surgical instrument of claim 15, wherein said working tool is one of powered tissue device, a manual instrument, an internal imaging device, and a suction device.

18. The surgical instrument of claim 17, wherein said working tool further comprises a flange portion and an insertion portion coupled to said shaft, wherein said flange portion and said insertion portion configured to be removably coupled to said handle to removably position said flexible region of said working tool within said articulating regions of said articulating tube assembly.

19. The surgical instrument of claim 15, wherein said actuation assembly further comprises a control wheel defining internal threads, and a lead screw fixedly coupled to said outer tube and comprising external threads coupled to said internal threads, wherein said control wheel is configured to receive a rotatable input so as to move said lead screw and said outer tube relative to said inner tube.

20. The surgical instrument of claim 19, further comprising a locking assembly coupled to said control wheel and configured to prevent rotation of said control wheel and maintain said articulating region is locked in one or more curvature configurations.

* * * * *